(12) United States Patent
Kool

(10) Patent No.: US 7,135,312 B2
(45) Date of Patent: Nov. 14, 2006

(54) CIRCULAR DNA VECTORS FOR SYNTHESIS OF RNA AND DNA

(75) Inventor: Eric T Kool, Stanford, CA (US)

(73) Assignee: University of Rochester, Rochester, NY (US)

( * ) Notice: Subject to any disclaimer, the term of this patent is extended or adjusted under 35 U.S.C. 154(b) by 605 days.

(21) Appl. No.: 09/997,931

(22) Filed: Nov. 30, 2001

(65) Prior Publication Data

US 2003/0087241 A1 May 8, 2003

Related U.S. Application Data

(63) Continuation-in-part of application No. 09/569,344, filed on May 11, 2000, now Pat. No. 6,368,802, which is a continuation of application No. 08/805,631, filed on Feb. 26, 1997, now Pat. No. 6,096,880, which is a continuation-in-part of application No. 08/393,439, filed on Feb. 23, 1995, now Pat. No. 5,714,320, which is a continuation-in-part of application No. 08/047,860, filed on Apr. 15, 1993, now abandoned.

(51) Int. Cl.
*C12P 19/34* (2006.01)
*C12Q 1/68* (2006.01)
*C12N 15/09* (2006.01)

(52) U.S. Cl. .............. 435/91.31; 435/6; 435/320.1; 435/91.1

(58) Field of Classification Search ............. 435/6, 435/320.1, 91.1, 91.3; 514/44
See application file for complete search history.

(56) References Cited

U.S. PATENT DOCUMENTS

| | | | |
|---|---|---|---|
| 4,795,700 A | 1/1989 | Dervan et al. | |
| 4,837,312 A | 6/1989 | Dervan et al. | |
| 4,987,071 A | 1/1991 | Cech et al. | |
| 5,093,246 A | 3/1992 | Cech et al. | |
| 5,246,921 A | 9/1993 | Reddy et al. | |
| 5,258,506 A | 11/1993 | Urdea et al. | |
| 5,354,668 A | 10/1994 | Auerbach | |
| 5,354,855 A | 10/1994 | Cech et al. | |
| 5,426,180 A | 6/1995 | Kool | |
| 5,470,724 A | 11/1995 | Ahern | |
| 5,498,531 A | 3/1996 | Jarrell | |
| 5,500,357 A | 3/1996 | Taira et al. | |
| 5,648,245 A | 7/1997 | Fire et al. | |
| 5,714,320 A | 2/1998 | Kool | |
| 6,077,668 A | 6/2000 | Kool | |
| 6,096,880 A | 8/2000 | Kool | |
| 6,368,802 B1 | 4/2002 | Kool | |

FOREIGN PATENT DOCUMENTS

| | | |
|---|---|---|
| JP | 4-262799 | 9/1992 |
| JP | 4-304900 | 10/1992 |
| JP | 5-146299 | 6/1993 |
| WO | WO 92/01813 | 2/1992 |
| WO | WO 92/17484 | 10/1992 |
| WO | WO 94/03630 | 2/1994 |
| WO | WO 96/00795 | 1/1996 |
| WO | WO 96/33207 | 10/1996 |
| WO | WO 97/19193 | 5/1997 |
| WO | WO 97/20948 | 6/1997 |
| WO | WO 97/43298 | 11/1997 |
| WO | WO 98/04746 | 2/1998 |
| WO | WO 98/38300 | 9/1998 |
| WO | WO 99/09216 | 2/1999 |

OTHER PUBLICATIONS

"Affinity Chromatography: Practical and Theoretical Aspects," Mohr, Ed., Dekker Publishing: New York, Title page, Copyright page, and Contents pages (pp. v-viii) (1985).
Agrawal, "Antisense Oligonucleotides: Towards Clinical Trials," *TIBTECH*, 14:376-387 (1996).
Aguilar et al., "Hairpin, Dumbbell, and Single-Stranded Phosphodiester Oligonucleotides Exhibit Identical Uptake in T. Lymphocyte Cell Lines," *Antisense & Nucleic Acid Drug Development*, 6:157-163 (1996).
Aiyar et al., "A Mismatch Bubble in Double-stranded DNA Suffices to Direct Precise Transcription Initiation by *Escherichia coli* RNA Polymerase," *J. Biol. Chem.*, 269:13179-13184 (1994).
Albrecht et al., "Cationic lipide mediated transfer of c-abl and bcr antisense oligonucleotides to immature normal myeloid cells: Uptake, biological effects and modulation of gene expression," *Ann. Hematol.*, 72:73-79 (1996).
Ali et al., "Enzymatic synthesis of DNA probes complementary to a human variable number tandem repeat locus," *Anal. Biochem.*, 179(2):280-283 (Jun. 1, 1989).

(Continued)

*Primary Examiner*—Sean McGarry
(74) *Attorney, Agent, or Firm*—Mueting, Raasch & Gebhardt, P.A.

(57) ABSTRACT

The present invention provides methods for synthesis and therapeutic use of DNA and RNA oligonucleotides and analogs. RNA oligonucleotides are synthesized using a small, circular DNA template which lacks an RNA polymerase promoter sequence. The RNA synthesis is performed by combining a circular single-stranded oligonucleotide template with an effective RNA polymerase and at least two types of ribonucleotide triphosphate to form an RNA oligonucleotide multimer comprising multiple copies of the desired RNA oligonucleotide sequence. Preferably, the RNA oligonucleotide multimer is cleaved to produce RNA oligonucleotides having well-defined ends. Preferred RNA oligonucleotide multimers contain ribozymes capable of both cis (autolytic) and trans cleavage.

18 Claims, 21 Drawing Sheets

OTHER PUBLICATIONS

Ashley et al., "Chemical Synthesis of Oligodeoxynucleotide Dumbbells," *Biochemistry*, 30:2927-2933 (1991).

Beaucage et al., "Deoxynucleoside Phosphoramidites—A New Class of Key Intermediates for Deoxypolynucleotide Synthesis," *Tetrahedron Lett.*, 22(20):1859-1862 (1981).

Beaucage et al., "The Functionalization of Oligonucleotides Via Phosphoramidite Derivatives," *Tetrahedron*, 49(10):1925-1963 (1993).

Blanco et al., "Highly Efficient DNA Synthesis by the Phage ø29 DNA Polymerase," *J. Biol. Chem.*, 264(15):8935-8940 (1989).

Bledsoe et al., "Molecular homology and DNA hybridization," *J. Mol. Evol.*, 30(5):425-433 (May 1990).

Bock et al., "Selection of single-stranded DNA molecules that bind and inhibit human thrombin," *Nature*, 355:564-566 (1992).

Branch, "A Good Antisense is Hard to Find," *TIBS*, 23:45-50 (1998).

Capaccioli et al., "Cationic Lipids Improve Antisense Oligonucleotide Uptake and Prevent Degradation in Cultured Cells and in Human Serum," *Biochemical and Biophysical Research Communications*, 197(2):818-825 (1993).

Chin et al., "Catalytic Hydrolysis of Amides at Neutral pH," *J. Chem. Soc., Chem. Commun.*, 1326-1328 (1990).

Chowrira et al., "In Vitro and In Vivo Comparison of Hammerhead, Hairpin, and Hepatitis Delta Virus Self-Processing Ribozyme Cassettes," *Journal of Biological Chemistry*, 269:25856-25864 (1994).

Compton, "Nucleic acid sequence based amplification," *Nature*, 350:91-92 (1991).

Cwirla et al., "Peptides on phage: A vast library of peptides for identifying ligands," *PNAS, USA*, 87:6378-6382 (1990).

Daube et al., "Functional Transcription Elongation Complexes from Synthetic RNA-DNA Bubble Duplexes," *Science*, 258:1320-1324 (1992).

Daubendiek et al., "Generation of Catalytic RNAs by Rolling Transcription of Synthetic DNA Nanocircles," *Nature Biotech.*, 15:273-277 (Mar. 1997).

Daubendiek, "Rolling-Circle RNA Synthesis: Circular Oligonucleotides as Efficient Substrates for T7 RNA Polymerase," No. 112625x of *Chem. Abstr.*, 123: 1175 (1995).

Daubendiek et al., "Rolling-Circle RNA Synthesis: Circular Oligonucleotides as Efficient Substrates for T7 RNA Polymerase," *J. Am. Chem. Soc.*, 117:7818-7819 (1995).

Daubendiek et al., "Rolling Circle Transcription: The Use of Small Circular DNAs as Templates for RNA Synthesis," Ph.D. Dissertation, University of Rochester, Rochester, New York, *UMI Dissertation Services*, A Bell & Howell Company, Ann Arbor, Michigan, Title Page, Table of Contents, pp. 1-184 (1998).

Diegelman et al., "Generation of Circular RNAs and Trans -Cleaving Catalytic RNAs by Rolling Transcription of Circular DNA Oligonucleotides Encoding Hairpin Ribozymes," *Nucleic Acids Research*, 26:3235-3241 (1998).

D'Souza et al., "Strong Binding of Single-stranded DNA by Stem-Loop Oligonucleotides," *J. Biomolecular Structure and Dynamics*, 10(1):141-152 (1992).

Dzianott et al., "Derivation of an infectious viral RNA by autolytic cleavage of *in vitro* transcribed viral cDNAs," *PNAS USA*, 86:4823-4827 (1989).

Egholm et al, "PNA hybridizes to complementary oligonucleotides obeying the Watson-Crick hydrogen-bonding rules," *Nature*, 365(6446):566-568 (Oct. 7, 1993).

Eisenberg et al., The Single-Stranded DNA Phages, Eds., Denhardt, Cold Spring Harbor Press, Cold Spring Harbor, Title page, Copyright page, Contents pages, pp. 298-299 (1978).

Eisenberg et al., "Enzymatic replication of viral and complementary strands of duplex DNA of phage øXI74 proceeds by separate mechanisms," *PNAS USA*, 73(9):3151-3155 (1976).

Ellington et al., "In vitro selection of RNA molecules that bind specific ligands," *Nature*, 346:818-822 (1990).

Ellington et al., "Selection in vitro of single-stranded DNA molecules that fold into specific ligand-binding structures," *Nature*, 355:850-852 (1992).

Elroy-Stein et al., "Cytoplasmic expression system based on constitutive synthesis of bacteriophage T7 RNA polymerase in mammalian cells," *Proc. Natl. Acad. Sci. USA*, 87:6743-6747 (Sep. 1990).

Famulok et al., "Stereospecific Recognition of Tryptophan Agarose by in vitro Selected RNA," *J. Am. Chem. Soc.*, 114:3990-3991 (1992).

Fire et al., "Rolling replication of short DNA circles," *PNAS USA*, 92:4641-4645 (1995).

Flory et al., "Nuclease-Resistant Ribozymes Decrease Stromelysin mRNA Levels in Rabbit Synovium Following Exogenous Delivery to the Knee Joint," *Proc. Natl. Acad. Sci. USA*, 93:754-758 (1996).

Forster et al., "Structural and Ionic Requirements for Self-cleavage of Virusoid RNAs and trans Self-cleavage of Viroid RNA," Cold Spring Harbor Symposia on Quantitative Biology, vol. OLII, 249-259 (1987).

Grosshans et al., "A hammerhead ribozyme allows synthesis of a new form of the *Tetrahymena* ribozyme homogenous in length with a 3' end blocked for transesterification," *Nucleic Acids Research*, 19(14):3875-3880 (1991).

Gura, "Antisense Has Growing Pains," *Science*, 270:575-577 (1995).

Guy-Caffey et al., "Novel Polyaminolipids Enhance the Cellular Uptake of Oligonucleotides," *J. Biol. Chem.*, 270(52):31391-31396 (1995).

Harshey et al., "A mechanism of DNA transposition," *PNAS USA*, 78:1090-1094 (1981).

Haseloff et al., "Simple RNA Enzymes with New and Highly Specific Endoribonuclease Activities," *Nature*, 334:585-591 (1988).

Hoffman et al., "Enzymatic Synthesis of Milligram Quantitites of Ribozymes in Small Volumes," *BioTechniques*, 17:372-375 (1994).

Horn et al., "The Synthesis of Branched Oligonucleotides as Signal Amplification Multimers for Use in Nucleic Acid Assays," *Nucleosides & Nucleotides*, 8(5&6):875-877 (1989).

Hutchins et al., "Self-cleavage of plus and minus RNA transcripts of avocado sunblotch viroid," *Nucleic Acids Research*, 14(9):3627-3641 (1986).

James, "Towards gene-inhibition therapy: a review of progress and prospects in the field of antiviral antisense nucleic acids and ribozymes," *Antiviral Chemistry & Chemotherapy*, 2(4):191-214 (1991).

Kanaya et al., "Template-Directed Polymerization of Oligoadenylates Using Cyanogen Bromide," *Biochemistry*, 25:7423-7430 (1986).

Kashani-Sabat et al., "Reversal of the Malignant Phenotype by an Anti-ras Ribozyme," *Antisense Research and Development*, 2:3-15 (1992).

Kawai et al., "A simple method of detecting amplified DNA with immobilized probes on microtiter wells," *Anal. Biochem.*, 209(1):63-69 (Feb. 15, 1993).

Kazakov et al., "A Trinucleotide Can Promote Metal Ion-Dependent Specific Cleavage of RNA," *Pro. Natl. Acad. Sci. USA*, 89:7939-7943 (1992).

Kim et al., "Dimethyl Phosphate Hydrolysis at Neutral pH," *J. Am. Chem. Soc.*, 114:9792-9795 (1992).

Kitajima et al., "Alblation of Transplanted HTLV-I Tax-Transformed Tumors in Mice by Antisense Inhibition of NF-κB," *Science*, 258:1792-1795 (1992).

Koizumi et al., "Ribozymes Designed to Inhibit Transformation of NIH3T3 Cells by the Activated c-Ha-ras Gene," *Gene*, 117:179-184 (1992).

Koo et al., "Determination of the Extent of DNA Bending by an Adenine-Thymine Tract," *Biochemistry*, 29:4227-4234 (1990).

Kool et al., "Abstract of National Institute of General Medical Sciences Grant No. 5R01-GM46625-06," titled "Binding of HIV 1 Sequences by Cyclic Oligonucleotides," (funded in Fiscal Year 1997).

Kool, "Circular Oligonucleotides: New Concepts in Oligonucleotide Design," *Annu. Rev. Biophys. Biomol. Struct.*, 25:1-28 (1996).

Kool, "Circular Oligonucleotides as Potential Modulators of Gene Expression," Report No. ARO 315.8-LS-YIP, U.S. Army Research Office, pp. 124-149 (May 1996).

Kool, "Molecular Recognition by Circular Oligonucleotides: Increasing the Selectivity of DNA Binding," *J. Am. Chem. Soc.*, 113:6265-6266 (1991).

Kool, "New Multilabel Fluorescent Groups for Increased Sensitivity of DNA Detection," Report No. ARO 31507.10-LS-YIP, U.S. Army Research Office, pp. 1-7 (Oct. 1996).

Kool, "Topologically Modified Biopolymers—Properties of Synthetic Circular DNAs and RNAs," *Trends in Polymer Science*, 3:396-402 (1995).

Kool, "Topologically Modified Biopolymers: Properties of Synthetic Circular DNAs and RNAs," Report No. ARO 31507.8-LS-YIP, U.S. Army Research Office, pp. 336-402 (May 1996).

Kornberg, DNA Replication, W.H. Freeman.& Co., San Francisco, 569 (1980).

Krupp, "Unusual Promoter-Independent Transcription Reactions with Bacteriophage RNA Polymerases," *Nucleic Acids Research*, 17(8):3023-3036 (1989).

Ledwith et al., "Preparation of synthetic tandem-repetitive probes for DNA fingerprinting," *Biotechniques*, 9(2):149-152 (Aug. 9, 1990).

Lee et al., "A Molecular Titration Assay to Measure Transcript Prevalence Levels," in *Methods in Enzymology*, Eds., Berger et al., Academic Press, Inc., Orlando, FL, vol. 152, Title page, pp. 633-649 (1987).

Liu et al., "Rolling Circle DNA Synthesis: Small Circular Oligonucleotides as Efficient Templates for DNA Polymers," *J. Am. Chem. Soc.*, 118:1587-1594 (1996).

Long et al., "Self-cleaving catalytic RNA," *FASEB*, 7:25-30 (1993).

May et al., "DNA fingerprinting by specific priming of concatenated oligonucleotides," *Nucleic Acids Res.*, 19(16), 4557 (Aug. 25, 1991).

Milligan et al., "Oligoribonucleotide synthesis of T7 RNA polymerase and synthetic DNA templates," *Nucleic Acids Res.*, 15(21):8783-8798 (1987).

Miyamoto et al., "Total Synthesis of (+)-Validoxylamine G," *J. Chem. Soc., Chem. Commun.*, 999-1000 (1990).

Møllegaard et al., "Peptide nucleic acid-DNA strand displacement loops as artificial transcription promoters," *PNAS USA*, 91:3892-3895 (1994).

Myers et al., "Reverse Transcription and DNA Amplification by a *Thermus thermophilus* DNA Polymerase," *Biochemistry*, 30(31):7661-7666 (Aug. 1991).

"New England BioLabs Catalog," oX174, (1994).

Nielsen et al., "Peptide Nucleic Acid (PNA). A DNA Mimic with a Peptide Backbone," *Bioconjugate Chem.*, 1994, 5(1):3-7.

Nilsson et al., "Padlock probes: circularizing oligonucleotides for localized DNA detection," *Science*, 265(5181):2085-2088 (1994).

Noonberg et al., "Characteristics of Oligonucleotide Uptake in Human Keratinocyte Cultures," *Journal of Investigative Dermatology*, 101:727-731 (1993).

Oligodeoxynucleotides: Antisense Inhibitors of Gene Expression, Cohen, Ed.; CRC Press: Boca Raton, Fla, 1989; Title page, Copyright page, and Contents pages, pp. v-viii (1989).

Ohkawa et al., "Importance of independence in ribozyme reactions: Kinetic behavior of trimmed and of simply connected multiple ribozymes with potential activity against human immunodeficiency virus," *PNAS USA*, 90:11302-11306 (1993).

Olivera et al., "Enzymic Joining of Polynucleotides: IV. Formation of a Circular Deoxyandeylate-Deoxythymidylate Copolymer," *J. Mol. Biol.*, 36:275-285 (1968).

Pei et al., "A Combinatorial Approach Toward DNA Recognition," *Science*, 253:1408-1411 (1991).

Piccirilli et al., "Enzymatic Incorporation of a New Base Pair into DNA and RNA Extends the Genetic Alphabet," *Nature*, 343:33-37 (1990).

Podhadjska et al., "Conversion of the FokI Endonucease to a Universal Restriction Enzyme: Cleavage of Phage M13mp7 DNA at Predetermined Sites," *Gene*, 40:175-182 (1985).

Prakash et al., "Molecular Recognition by Circular Oligonucleotides. Strong Binding of Single-stranded DNA and RNA," *J. Chem. Soc., Chem. Commun.*, 17:1161-1163 (1991).

Prakash et al., "Structural Effects in the Recognition of DNA by Circular Oligonucleotides," *J. Am. Chem. Soc.*, 114:3523-3527 (1992).

Ratajczak et al., "*In vivo* treatment of human leukemia in a scid mouse model with c-myb antisense oligodeoxynucleotides," *PNAS*, 89:11823-11827 (1992).

Roberts et al., "Specificity and stringency in DNA triplex formation," *Proc. Natl. Acad. Sci. USA*, 88(21):9397-9401 (Nov. 1, 1991).

Robertson et al., "Selection *in vitro* of an RNA enzyme that specifically cleaves single-stranded DNA," *Nature*, 344:467-468 (1990).

Robertson et al., "The Viroid Replication Process," Semancik, Ed.; CRC Press, Inc., Boca Raton. Fla; Viroids and Viroid-Like Pathogens, Chapt. 2, pp. 50-68 (1987).

Rubin et al., "Convergent DNA synthesis: a non-enzymatic dimerization approach to circular oligodeoxynucleotides," *Nucleic Acids Research*, 23(17):3547-3553 (1995).

Ruffner et al., "Studies on the hammerhead RNA self-cleaving domain," *Gene*, 82, 31-41 (1989).

Rumney et al., "DNA Recognition by Hybrid Oligoether-Oligodeoxynucleotide Macrocylces," *Agnew. Chem. Intl. Ed. Engl.*, 31(12):1617-1619 (1992).

Saiki et al., "Primer-Directed Enzymatic Amplification of DNA with a Thermostable DNA Polymerase," *Science*, 239:487-491 (1988).

Sambrook et al., Molecular Cloning: A Laboratory Guide, 2$^{nd}$ ed.; Cold Spring Harbor, NY; Title page, Copyright page, contents pages (pp. V-xxxii), and Chapter 13, pp. 13.2-13.104 (1989).

Sarver et al., "Ribozymes as Potential Anti-HIV-1 Therapeutic Agents," *Science*, 247:1222-1225 (1990).

Scaringe et al., "Chemical Synthesis of Biologically Active Oligoribonucleotides Using β-cyanoethyl Protected Ribonucleoside Phosphoramidites," *Nucleic Acids Res.*, 18(18):5433-5441 (1990).

Schubbert et al., "Ingested foreign (phage M13) DNA survives transiently in the gastrointestinal tract and enters the bloodstream of mice," *Mol. Gen. Genet.*, 242:495-504 (1994).

Schweitzer et al., "Immunoassays with rolling circle DNA amplifications: A versatile platform for ultrasensitive antigen detection," *Proc. Natl. Acad. Sci. USA*, 97(18):10113-10119 (Aug. 29, 2000).

Seyhan et al., "Intracellular RNA cleavage by the hairpin ribozyme," *Nucleic Acids Research*, 26(15):3494-3504 (1998).

Short Protocols in Molecular Biology, Chapter 14, 3$^{rd}$ Edition, Wiley & Sons (1995).

Sigmund et al., "Effects of *Escherichia coli* Nus A Protein on Transcription Termination in Vitro Are Not Increased or Decreased by DNA Sequences Sufficient for Antitermination in Vivo," *Biochemistry*, 27(15):5628-5635 (1988).

Simon et al., "Convenient Syntheses of Cytidine 5'-Triphosphate, Guanosine 5'-Triphosphate, and Uridine 5'-Triphosphate and Their use in the Preparation of UDP-gulcose, UDP-glucuronic Acid, and GCP-mannose," *J. Org. Chem.* 55(6):1834-1841 (1990).

Sioud, "Ribozyme Modulation of Lipopolysaccharide-Induced Tumor Necrosis Factor-∝ Production by Peritoneal Cells *in vitro* and *in vivo,*" *Eurl. J. Immunol.*, 26:1026-1031 (1996).

Stull et al., "Antigene, Ribozyme, and Aptamer Nucleic Acids Drugs: Progress and Prospects," *Pharmaceutical Research*, 12:465-483 (1995).

Symons, "Avocado sunblotch viriod: primary sequence and proposed secondary structure," *Nucleic Acids Research*, 9(23):6527-6537 (1981).

Symons, "Small Catalytic RNAs," *Annu. Rev. Biochem.*, 61:641-671 (1992).

Szybalski et al., "Universal Restriction Endonucleases: Designing Novel Cleavage Specificities by Combining Adaptor Oligodeoxynucleotide and Enzyme Moieties," *Gene*, 40:169-173 (1985).

Taira et al., "Construction of a Novel Artificial-Ribozyme-Releasing Plasmid," *Protein Engineering*, 3(8):733-737 (1990).

Taira et al., "Construction of a novel RNA-transcript-trimming plasmid which can be used both *in vitro* in place of run-off and (G)-free transcription and *in vivo* as multi-sequences transcription vectors," *Nucleic Acids Research*, 19919):5125-5130 (1991).

Tessier et al., "Ligation of Single-stranded oligodeoxyribonucleotides by T4 RNA Ligase," *Anal. Biochem.*, 158:171-178 (1986).

Tomizawa et al., "Factor-Independent Termination of Transcription in a Stretch of Deoxyandenosine Residues in the Template DNA," *Cell*, 51:623-630 (1987).

Turek et al., "RNA Pseudoknots that Inhibit Human Immunodeficency Virus Type 1 Reverse Transcriptase," *PNAS*, 89:6988-6992 (1992).

Turek et al., "Systematic Evolution of ligands by exponential enrichment: RNA ligands to Bacteriophage T4 DNA Polymerase," *Science*, 249:505-510 (1990).

Uhlen, "Magnetic separation of DNA," *Nature*, 340(6236):733-734 (Aug. 31, 1989).

Uhlenbeck, "A Small catalytic oligoribonucleotide," *Nature*, 328:596-600 (1987).

Uhlmann et al., "Antisence oligonucleotides: a new therapeutic principle," *Chem. Rev.*, 90(4):543-584 (1990).

Ulanovsky, "Curved DNA: Design, synthesis, and circularization," *PNAS USA*, 83:862-866 (1986).

Vaishnav et al., "The Biochemistry of AIDS," *Ann. Rev. Biochem.*, 60:577-630 (1991).

Walker et al., "Isothermal *in vitro* amplification of DNA by a restriction enzyme/DNA polymerase system," *PNAS USA*, 89:392-396 (1992).

Wang et al., "Circular RNA Oligonucleotides. Sysnthesis, nucleic acid binding properties, and a comparison with circular DNAs," *Nucleic Acids Research*, 22(12):2326-2333 (1994).

Watson, Molecular Biology of the Gene, W.A. Benjamin, Inc., 238-241 (1976).

Zhou DM, Schultz PG, "Development of synthetic viroids," Abstr PAP—AM Chem. Soc 222: 194-Biol Part 1 Aug. 2001.

Venkatesan et al., "Preparation and properties of a poly A resin and its use in the isolation of naturally occurring poly U sequences," *Nucleic Acids Research*, Aug. 1976;3(8):1925-1936.

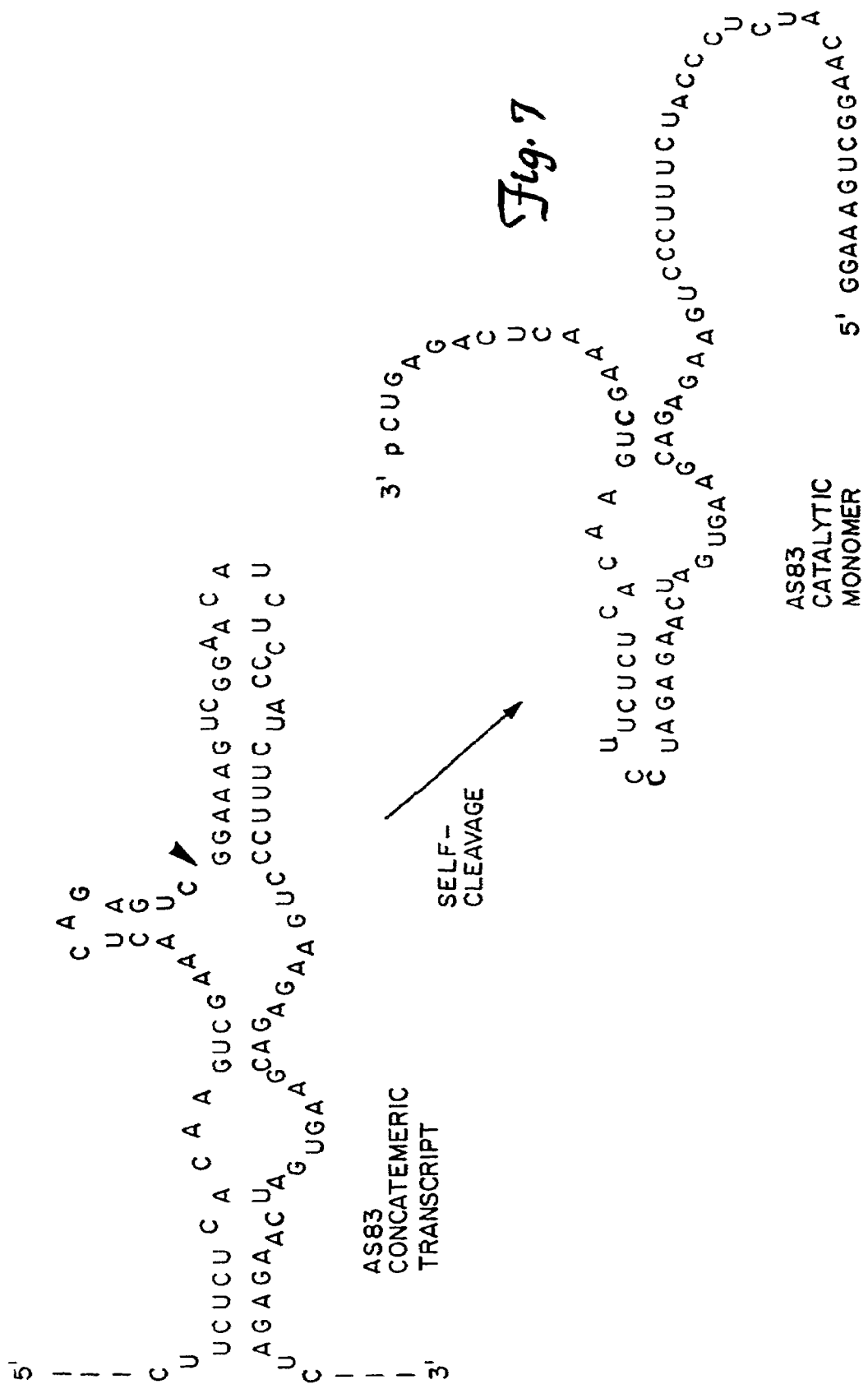

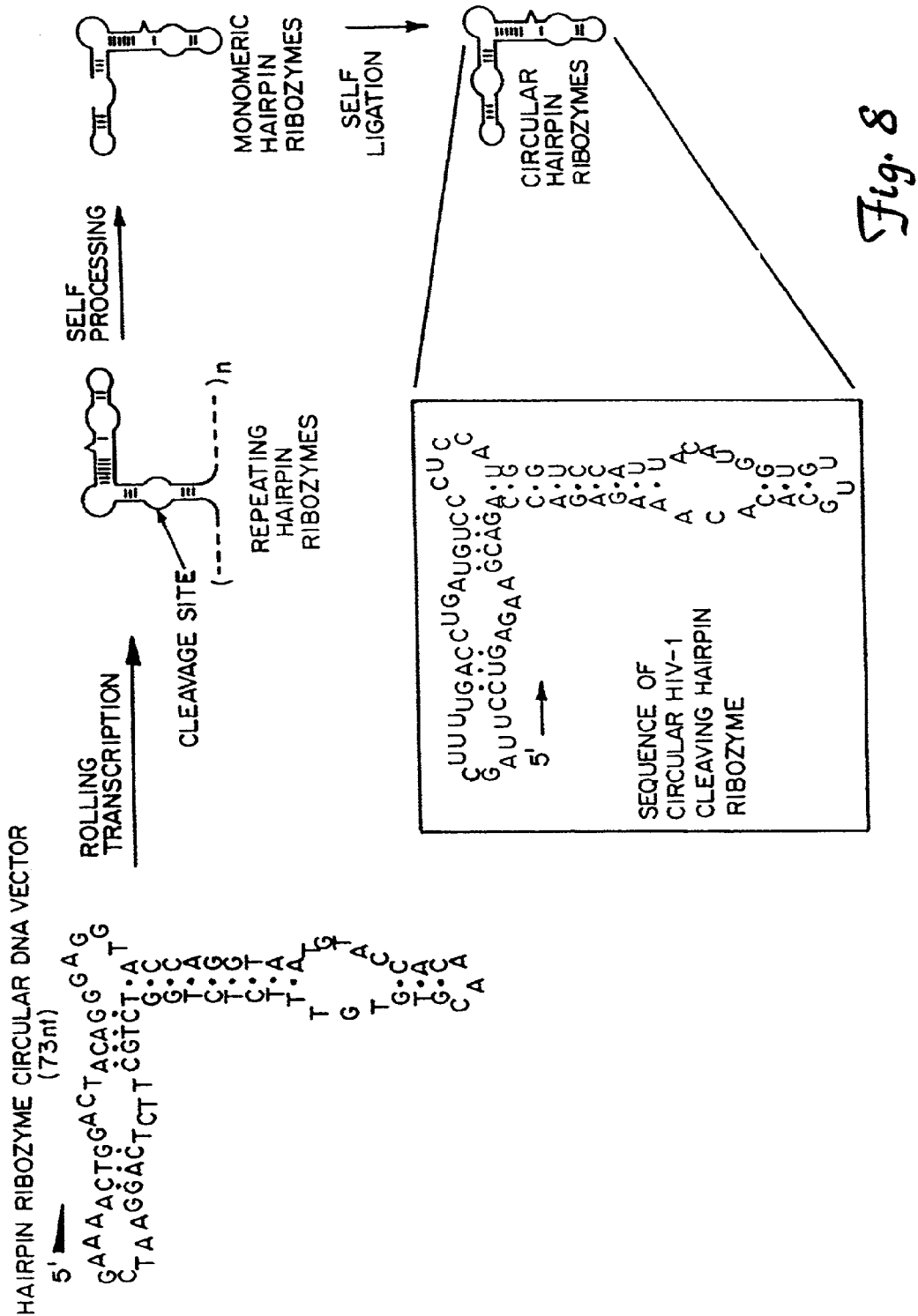

```
                GACTGAGGAGTTCGTCTG---------N40---------TCTTTCA GTTTCGTCCTCACGGACTCATCAGAATGGCAACACATT
                5'                                                                                    3'
```

|         |    |                                        |     |
|---------|----|----------------------------------------|-----|
| motif I | 1  | GCAACGAATCAGACTCTTTCGGTGACATTGCCCAGTTTAT | E1  |
|         | 3  | GCAACGAATCAGACTCTTTCGGTGACATTGCCCAGTTTAT |     |
|         | 5  | GCAACGAATCAGACTCTTTCGGTGACATTGCCCAGTTTAT |     |
|         | 7  | GCAACGAATCAGACTCTTTCGGTGACATTGCCCAGTTTAT |     |

|          |    |                                          |     |
|----------|----|------------------------------------------|-----|
| motif II | 8  | GCCACGATCTGAATAGTCGTTCATCCT[T]AGCGGTAGCGAA |     |
|          | 24 | G[T]CACGATCTGAATAGTCGTTCATCCTCAGCGGTAGCGAA |     |
|          | 38 | GCCACGATCTGAATAGTCGTTCATCCTCAGCGGTAGCGAA | E38 |

|           |    |       |       |       |        |         |               |     |
|-----------|----|-------|-------|-------|--------|---------|---------------|-----|
| motif III | 11 | GCTT  | AAG   | GATTAA| TTGC   | ATGTTA  | TTCTTTA GGAGCCTCGA |     |
|           | 15 | GTA   | AAG   | TATG  | TTGC   | TACGAC  | TTCTTTA TTTACCACGATGC | E15 | other  
2  GAGCAGTGGTCAACTGACGGCTTCGAAATGATATGCAGCG  
6  TATGACGATAGGATTAGACGTGTGGGGGTATTTTCACTAC  
17 GTCTCACTCGGAGGAGGAGTCTGACAAGATGGGATGCTGC  
19 GGTATTGCAGACTATTTAGCCTCTGAGAGCCAGAACGGTC  
21 GAGTGGTAAGTACTGGGAGCCACTCACGACAACGAACAA  
25 GTGCTATTCGTGGCTATACTGTTAATGTGTCGCACCATTC  
28 GGCCCCGTTTAGGTACAATCACATGTACTAGCGTTGTGGT  
31 GTAGGGTTAATATCCTTCTCGTATGACCGTGGAAGACGTC  
34 GGATGCGTAGCGTAAAGCGTTCGTATCTCGAGGTAAGCTT  
37 GAGCCATGGAGCATACTAGTTGAACTCTAGCTTCTAGTCC

Figure 11

A
active marA (103nt)
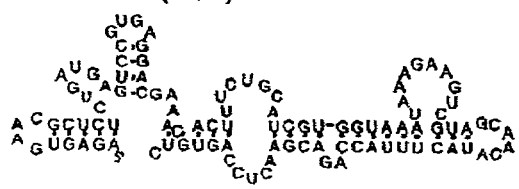
inactive marA (103nt)
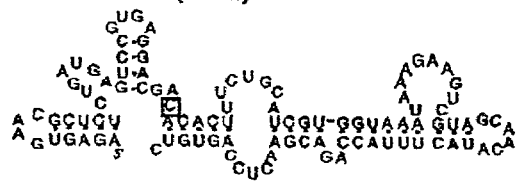
short marA (63nt)
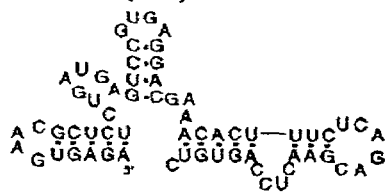
B
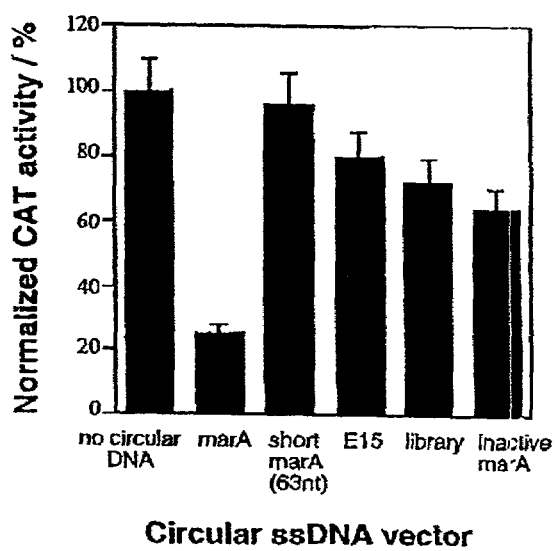
Figure 17

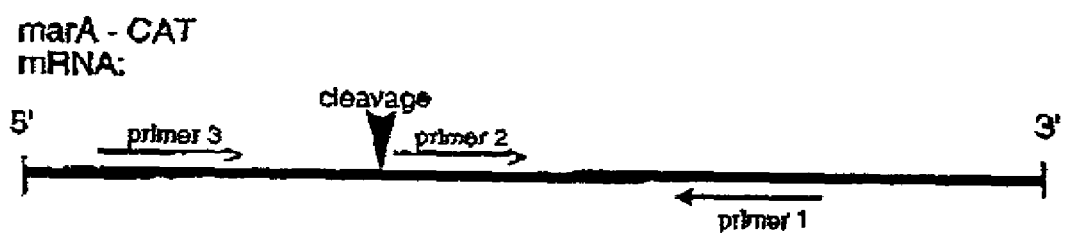
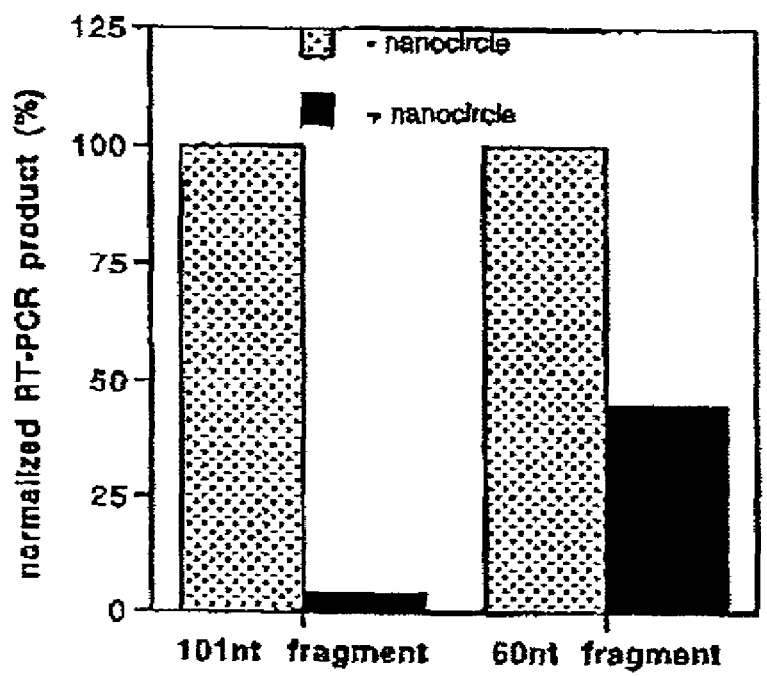
Figure 18

73 nt circular DNA

CIRCULAR DNA VECTORS FOR SYNTHESIS OF RNA AND DNA

This is a continuation-in-part application of U.S. patent application Ser. No. 09/569,344, filed May 11, 2000 now U.S. Pat. No. 6,368,802, which is a continuation application of U.S. patent application Ser. No. 08/805,631, filed Feb. 26, 1997, and issued as U.S. Pat. No. 6,096,880 on Aug. 1, 2000, which is a continuation-in-part application of U.S. patent application Ser. No. 08/393,439, filed Feb. 23, 1995, and issued as U.S. Pat. No. 5,714,320, which is a continuation-in-part application of U.S. patent application Ser. No. 08/047,860, filed Apr. 15, 1993, now abandoned, all of which are incorporated herein by reference.

STATEMENT OF GOVERNMENT RIGHTS

The present invention was made with Government support under Grant Nos. RO1-GM46625 and DAMD17-98-1-8239 awarded by the National Institutes of Health and by the Department of Defense—U.S. Army Breast Cancer Research Program, respectively. The Government has certain rights in the invention.

FIELD OF THE INVENTION

The present invention provides methods for synthesis and therapeutic use of DNA and RNA oligonucleotides and analogs.

BACKGROUND OF THE INVENTION

In recent years the availability of automated DNA synthesizers has revolutionized the fields of molecular biology and biochemistry. As a result, linear DNA oligonucleotides of specific sequences are available commercially from several companies. These can be used for a variety of applications. For example, DNA oligonucleotides can be used as primers for cDNA synthesis, as primers for the polymerase chain reaction (PCR), as templates for RNA transcription, as linkers for plasmid construction, and as hybridization probes for research and diagnostics.

DNA and RNA oligonucleotides, i.e., oligomers, also can act as sequence-specific inhibitors of gene expression through binding of a complementary, or "antisense," base sequence. See, for example, E. Uhlmann et al., *Chem. Rev.*, 90, 543 (1990), and *Oligodeoxynucleotides: Antisense Inhibitors of Gene Expression*; J. S. Cohen, Ed.; CRC Press: Boca Raton, Fla., 1989. These antisense oligomers have been shown to bind to messenger RNA at specific sites and inhibit the translation of the RNA into protein, splicing of mRNA or reverse transcription of viral RNA and other processing of mRNA or viral RNA. In addition, "anti-gene" oligomers have been developed that bind to duplex DNA and inhibit transcription.

Strong inhibitory activity has been demonstrated in vitro and in vivo using these antisense and anti-gene oligomers against viruses such as HIV-1, Herpes Simplex Virus, and influenza virus, among others, as well as against several types of cancer. Thus, antisense and anti-gene oligonucleotides could be used as antiviral and anticancer agents and therapeutic agents against almost any disease mediated by gene expression. In addition, in some cases improved activity has been reported for analogs of DNA, including DNA and RNA phosphorothioates and 2'-O-methyl-ribonucleotides. All potential therapeutic applications, however, would require large amounts (tens or hundreds of grams) of specific oligomers for animal and clinical trials, and even more for eventual use as a pharmaceutical. See, for example, I. Kitajima et al., *Science*, 258, 1792 (1992), and M. Z. Ratajczak et al., *PNAS*, 89, 11823 (1992).

Ribozymes are naturally occurring RNA sequences that possess the property of self-catalyzed (autolytic) cleavage. Known ribozymes include, for example, hairpin and hammerhead motifs. The catalytic "hammerhead" domain of a ribozyme typically contains 11–13 conserved nucleotides at the juncture of three helices precisely positioned with respect to the cleavage site. A hammerhead containing less than 60 contiguous nucleotides was found to be sufficient for rapid autolytic cleavage in the absence of any protein (D. E. Ruffner et al., *Gene*, 82, 31–41 (1989)).

Autolytic cleavage by ribozymes is an intramolecular event and is referred to as occurring "in cis". However, the essential constituents for a biologically active RNA hammerhead structure can be present on separate molecules. For example, one strand may serve as a catalyst and the other as a substrate. Ribozymes acting in trans can, for example, interfere with the production of a protein by cleaving the target mRNA transcript encoding the protein. Reddy et al. disclosed ribozyme cleavage of a target RNA in trans using a synthetic RNA molecule containing a hammerhead (catalytic region) flanked by sequences designed to hybridize to the target RNA substrate on either side of the potential cleavage site. (U.S. Pat. No. 5,246,921, issued Sep. 21, 1993). The novel ribozyme was capable of selectively cleaving the bcr-abl mRNA of a cell containing the Philadelphia Chromosome, thereby blocking synthesis of the BCR-ABL protein associated with some forms of leukemia.

One major drawback in the use of oligonucleotides as diagnostic tools or therapeutic agents is the high cost of oligonucleotide synthesis by machine using the standard solid-phase synthetic methods. Reasons for this include the high costs of the synthetically modified monomers, e.g., phosphoramidite monomers, and the fact that up to a tenfold excess of monomer is used at each step of the synthesis, with the excess being discarded. Costs of DNA oligonucleotides have been estimated at $2–5 per base for one micromole (about 3 mg of a 10 mer) on the wholesale level. On this basis, 1 gram of a 20-base oligomer would cost on the order of $20,000. Thus, significant in vivo testing of antisense oligomers will be quite expensive until ways are found to lower the cost.

Enzymatic methods have the potential for lowering the cost of oligonucleotide synthesis. Enzymatic methods use DNA or RNA nucleotide triphosphates (dNTPs or NTPs) derived from natural sources as the building blocks. These are readily available, and are less expensive to produce than phosphoramidite monomers. Generally, this is because the synthesis of the nucleotide triphosphates from base monophosphates requires as little as one step. See, for example, E. S. Simon et al., *J. Org. Chem.*, 55, 1834 (1990). Nucleotide triphosphates (NTPs) can also be prepared enzymatically. In addition, the polymerase enzymes used in these methods are efficient catalysts, and are also readily available.

There are two major methods now in use for enzymatic amplification of DNA: cloning and the polymerase chain reaction (PCR). See, for example, J. Sambrook et al., *Molecular Cloning*; 2nd ed.; Cold Spring Harbor Press, 1989, and R. K. Saiki et al., *Science*, 239, 487 (1988). Cloning requires the insertion of a double-stranded version of the desired sequence into a plasmid followed by transformation of a bacterium, growth, plasmid re-isolation, and excising the desired DNA by restriction endonucleases. This method is not feasible for large-scale preparation because most of the material produced (the vector) is in the form of unusable DNA sequences. PCR is a newer technique that uses a thermostable polymerase to copy duplex sequences using primers complementary to the DNA. Subsequent heating and cooling cycles allow efficient amplification of the original sequence. For short oligomers, such as those used in anti-sense applications (e.g., less than about 50 nucleotides), PCR is inefficient and not cost-effective because it requires a primer for every new strand being synthesized.

Recently, a method was developed for the enzymatic synthesis of DNA oligomers using a noncleavable linear hairpin-shaped template/primer in a PCR-like enzymatic synthesis. See G. T. Walker et al., *PNAS*, 89, 392 (1992). Although this method may be more cost-effective than PCR, the polymerase must still dissociate from the template to enable amplification. Furthermore, the end groups of the DNA produced are ragged and not well defined.

Other methods of DNA replication are discussed in Harshey et al., *Proc. Nat'l. Acad. Sci., USA*, 78, 1090 (1985); and Watson, *Molecular Biology of the Gene* (3rd Edition). Harshey et al., discuss the theoretical method of "roll-in" replication of double-stranded, large, circular DNA. The "roll-in" process involves small, double-stranded circle cleavage and incorporation into a genome. It is primarily a process for inserting double-stranded plasmids into a double-stranded genome. Although one could conceivably use an entire genome to replicate an oligonucleotide, the resulting product would be thousands of nucleotides longer than desired. Thus, the "roll-in" process would be a very inefficient means to produce target oligonucleotide sequences. Watson briefly mentions the replication of single-stranded circles, but the author focuses the reference on the replication of double-stranded circles.

Prior to the present invention, it was thought by those skilled in the art that processive rolling-circle synthesis would not proceed without additional proteins which unwind the duplex ahead of the polymerase. See, e.g. Eisenberg et al., *PNAS USA*, 73:3151 (1976); *The Single-Stranded DNA Phages*, D. T. Denhardt et al., eds., Cold Spring Harbor Press; Cold Spring Harbor (1978); and DNA Replication, W. H. Freeman, San Francisco, 1980. In Eisenberg et al., the in vitro replication of φX174 DNA using purified proteins is disclosed. Among the least necessary proteins are DNA unwinding protein (also known as SSB, single-strand binding protein), cisA protein, and rep protein. These DNA unwinding proteins (which require ATP) are necessary for this replicative synthesis; otherwise the polymerase stalls. *The Single-Stranded DNA Phages* includes a discussion of the mechanism of replication of a single-stranded phage and furthermore shows a scheme for this replication in FIG. 8 therein. One of the beginning stages of replication involves the elongation of a single-stranded (−) template annealed to a full-length linear (+) strand. Any further elongation necessarily requires unwinding of the helix ahead of the polymerase. DBP (Double-strand binding protein) was thought to be necessary to coat the displaced strand in order for there to be successful DNA synthesis during elongation.

The polymerase from phage φ29 is known to amplify DNA strands as large as 70 kb in length. Even though this polymerase exhibits such a high degree of processivity, the use of the polymerase from phage φ29 still results in the wasteful (in both time and monetary resources) production of unwanted nucleotides. In order to replicate an oligonucleotide prior to the present invention, those of skill in the art would have encoded the oligonucleotide as only a small portion of the entire replicated region. Moreover, utilizing a plasmid or phage method to replicate an oligonucleotide would require the investigator to first separate the strands and then purify the oligonucleotide from thousands of other base pairs.

RNA oligomers are currently synthesized by two principal methods: DNA synthesizer and enzymatic runoff transcription. Methods have been recently published for the use of a synthesizer to construct RNA oligomers using a modification of the phosphoramidite approach. See, for example, S. A. Scaringe et al., *Nucleic Acids Res.*, 18, 5433 (1990). Chemical synthesis of RNAs has the advantage of allowing the incorporation of nonnatural nucleosides, but the yield decreases significantly as the length of the RNA product increases; stepwise yields of only 97.5% per round of synthesis are typical. Moreover, because of the need for additional protecting groups, RNA phosphoramidite monomers are considerably more expensive than are the DNA phosphoramidite monomers, making RNA synthesis by this method extremely costly. An alternative, the enzymatic runoff transcription method, utilizes a single or double-stranded DNA template. Runoff transcription requires a phage polymerase promoter, thus a DNA strand ~20 nucleotides longer than the RNA desired must be synthesized. There are also strong sequence preferences for the RNA 5' end (J. F. Milligan et al., *Nucleic Acids Res.*, 15, 8783–8798 (1987)). In runoff transcription the RNA copy begins to form on the template after the phage polymerase promoter and runs until the end of the template is reached. This method has the disadvantages of producing RNA oligomers with ragged, ill-defined end groups and giving relatively slow amplification. Both chemical synthesis and runoff transcription produce a number of undesired products shorter or longer than the desired RNA, lowering effective yields and requiring careful purification.

Double-stranded DNA plasmid vectors can be constructed to encode ribozymes as well as their self-cleavage sites, leading to self-processing after transcription (A. M Dzianott et al., *Proc. Natl. Acad. Sci. USA*, 86, 4823–4827 (1989); C. A. Grosshans et al., *Nucleic Acids Res.*, 19, 3875–3880 (1991); K. Taira et al., *Nucleic Acids Res.*, 19, 5125–5130 (1991)). However, plasmid vectors contain thousands of nucleotides extraneous to those required for the actual desired transcript, making them highly inefficient templates for ribozyme synthesis; shorter sequences generally possess greater activity. Their large size also poses problems for delivery into cells in cases where transcription is to be performed intracellularly. Also, plasmid vectors require promoters to initiate transcription.

Thus, there is a need for a low-cost, fast, and efficient method for the production of DNA and RNA oligomers having well-defined ends on a large scale. In view of their great therapeutic potential, new methods for in vitro and in vivo synthesis of ribozymes are particularly needed. In addition, there is a need to produce DNA and RNA analogs, such as, for example, DNA phosphorothioates, RNA phosphorothioates, and 2'-O-methyl ribonucleotides, with well-defined ends on a large scale and in an efficient manner. Furthermore, there is a need for a method that uses readily available enzymes and a readily prepared template to generate large amounts of a complementary sequence.

SUMMARY OF THE INVENTION

The present invention provides methods for the synthesis of oligonucleotides, preferably RNA oligonucleotides, using small, single-stranded circular oligonucleotide templates.

The methods are directed to efficient, low-cost, and large-scale synthesis of DNA and RNA oligomers and their analogs for use, for example, as probes and diagnostic and/or therapeutic agents.

A preferred method of the present invention is directed to the synthesis of RNA oligonucleotides, preferably biologically active RNA oligonucleotides. Synthesis involves combining an effective amount of a single-stranded circular oligonucleotide template with an effective amount of at least two types of ribonucleotide triphosphate and an effective amount of a RNA polymerase enzyme to form an RNA oligonucleotide multimer containing multiple copies of an RNA oligonucleotide complementary to the circular oligonucleotide template. It is also notable that the use of oligonucleotide primer is not necessary, and the circular template thus preferably lacks a primer-binding site.

This method is preferably carried out using a circular template that lacks an RNA polymerase promoter sequence. Preferably, the RNA oligonucleotide multimer is cleaved to produce the desired RNA oligonucleotide. Cleavage can be autolytic, as where the oligonucleotide multimer contains multiple copies of a self-cleaving ribozyme, or can be effected chemically or by an exogenous agent. In a particularly preferred embodiment, the ribozymes can act in trans as well as in cis. The resulting linear RNA oligonucleotides, i.e., oligomers, and their analogs, have well-defined ends. After formation of the linear oligonucleotides, the oligonucleotide can be circularized to form circular oligonucleotide products. The oligomers formed by the method of the present invention are capable of full sequencing and identification such that the ends are readily identifiable.

Synthesis of DNA oligonucleotides according to the method of the invention requires the addition of an oligonucleotide primer to initiate synthesis. The circular template must thus contain sequences at least partially complementary to the primer in order to prime the template.

The synthetic methods of the invention can be performed in vitro or inside a cell. If the method is performed inside a cell, it may be performed either ex vivo or in vivo. Any cell type can be used, e.g., bacterial, plant or animal. The method of the invention may be performed in situ as where a single-stranded circular oligonucleotide template comprising at least one copy of a nucleotide sequence complementary to the sequence of a desired oligonucleotide is taken up by the cell and processed intracellularly to yield an oligonucleotide multimer comprising multiple copies of the desired oligonucleotide, which may optionally be cleaved into monomer form. Therapeutic oligonucleotides may be produced intracellularly using the method of the invention.

Preferably, the oligonucleotide synthesized according to the method of the invention is biologically active. The oligonucleotide multimer product preferably contains a ribozyme sequence and its associated cleavage sequence, such that it can self-process to monomeric length. In a particularly preferred embodiment, the synthetic method produces a biologically active RNA that cleaves a disease-associated RNA, DNA, or protein. The invention thus provides also for oligonucleotide products synthesized or prepared according to the methods of the invention.

The single-stranded circular template is complementary to the nucleotide sequence of the desired oligonucleotide product. The circular template can contain one or more copies of the complementary sequence. Preferably, a circular template has about 15–1500 nucleotides, and more preferably about 24–500 nucleotides and most preferably about 30–150 nucleotides. The desired nucleotide product sequence can be a sense, an antisense or any other nucleotide sequence including a random sequence. The oligonucleotide circular template itself may be constructed of DNA or RNA or analogs thereof. Preferably, the circular template is constructed of DNA. The oligonucleotide primer binds to a portion of the circular template and is preferably single-stranded having about 4–50 nucleotides, and more preferably about 6–12 nucleotides.

The polymerase enzyme can be any that effects the synthesis of the multimer. For the synthesis of RNA oligomers the polymerase enzyme is preferably selected from the group consisting of T7 RNA Polymerase, T4 RNA Polymerase, SP6 RNA Polymerase, RNA Polymerase II, RNA Polymerase III, T3 RNA Polymerase and E. coli RNA Polymerase. Closely homologous mutants of the enzymes above, i.e., mutants with greater than about 80% homology, can also be included. It is not necessary to include an RNA Polymerase promoter sequence on the circular oligonucleotide template.

For the synthesis of DNA oligomers the polymerase enzyme is preferably selected from the group consisting of DNA Polymerase I, Klenow fragment of DNA Polymerase I, T4 DNA Polymerase, T7 DNA Polymerase, Taq Polymerase, AMV Reverse Transcriptase. More preferably, the polymerase enzyme is a Klenow fragment of DNA Polymerase I.

As used herein, "an effective amount" refers to an amount of the component effective to produce multimers longer than the circular template, preferably about 4–4000 times the length of the circular template. Preferably, the primer is provided in an amount of about 0.1–100 moles per mole of circular template, and the nucleotide triphosphates are provided in an amount of about $50-10^7$ and more preferably $200-2\times10^6$ moles per mole of circular template. As used herein, "oligonucleotide" and "oligomer" are used interchangeably to refer to a sequence-defined and length-defined nucleic acid or analog thereof, whereas a "multimer" is a repeated nucleic acid linear polymer containing end to end copies of an oligomer. The terms DNA and RNA should be understood to include not only naturally occurring nucleic acids, but also sequences containing nucleotide analogs or modified nucleotides, such as those that have been chemically or enzymatically modified.

The present invention also includes methods for modifying sequences containing the structure or function of a target molecule in a cell wherein a single-stranded circular oligonucleotide template is introduced into cells. The circular oligonucleotide serves as a template for the synthesis of an oligonucleotide that binds or otherwise affects a target molecule, preferably a protein or nucleic acid molecule. The oligonucleotide preferably contains a ribozyme.

The invention also provides a kit containing RNA standards to aid in molecular weight determinations. The RNA molecules provided as molecular weight standards are synthesized from a single-stranded circular oligonucleotide template encoding a self-cleaving RNA according to the method of the invention, and differ in size by defined increments within a useful molecular weight range. Alternatively, the kit contains a single-stranded circular oligonucleotide template encoding a self-cleaving RNA that is selected to produce the desired set of RNA molecules when transcribed.

BRIEF DESCRIPTION OF THE DRAWINGS

FIG. 7. Concatemeric RNA transcript produced from transcription of AS83 nanocircle (SEQ ID NO:51) folds to form a string of hammerhead-motif RNAs (SEQ ID) NO:58), which then self-cleave at the indicated site to ultimately yield oligoribonucleotide monomers 83 nucleotides in length (SEQ ID NO:59).

FIG. 8. Scheme for rolling transcription of synthetic nanocircle vector (SEQ ID NO:60) encoding a hairpin ribozyme and its own substrate; concatemers cleave autolytically and self-ligate to form circular monomers (SEQ ID NO:61) capable of trans cleavage.

FIG. 11. Sequences of the selected clones of single-stranded DNA nanocircle library containing 40 nt motifs labeled E1 (SEQ ID NO:104), E15 (SEQ ID NOs:108 and 109) and E38 (SEQ ID NO:105) and other random 40 nt sequences (SEQ ID NOs:111–120) obtained following in vitro selection. Boxes indicate regions of high sequence similarity. Boxes surrounding single sequences within motif II indicate a sequence difference as compared to the other members of the motif.

FIG. 17. (A) Sequences and predicted secondary structures of the monomer ribozymes: active (SEQ ID NO:125) and inactive marA (SEQ ID NO:126), and short marA (SEQ ID NO:127). The inactivating A→C mutation in inactive marA ribozyme is boxed. (B) Effect of 10 μM of various nanocircle vectors on the inhibition of CAT activity. The plotted data were averaged from three independent experiments.

FIG. 18. (A) Schematic showing RT-PCR with one downstream primer and two different upstream primers on either side of cleavage point. (B) Diagram showing the amount of full-length RNA produced in the presence of marA103 NCV (speckled columns) and in the absence of marA103 NCV (solid columns).

DETAILED DESCRIPTION OF THE INVENTION

Figure 1:
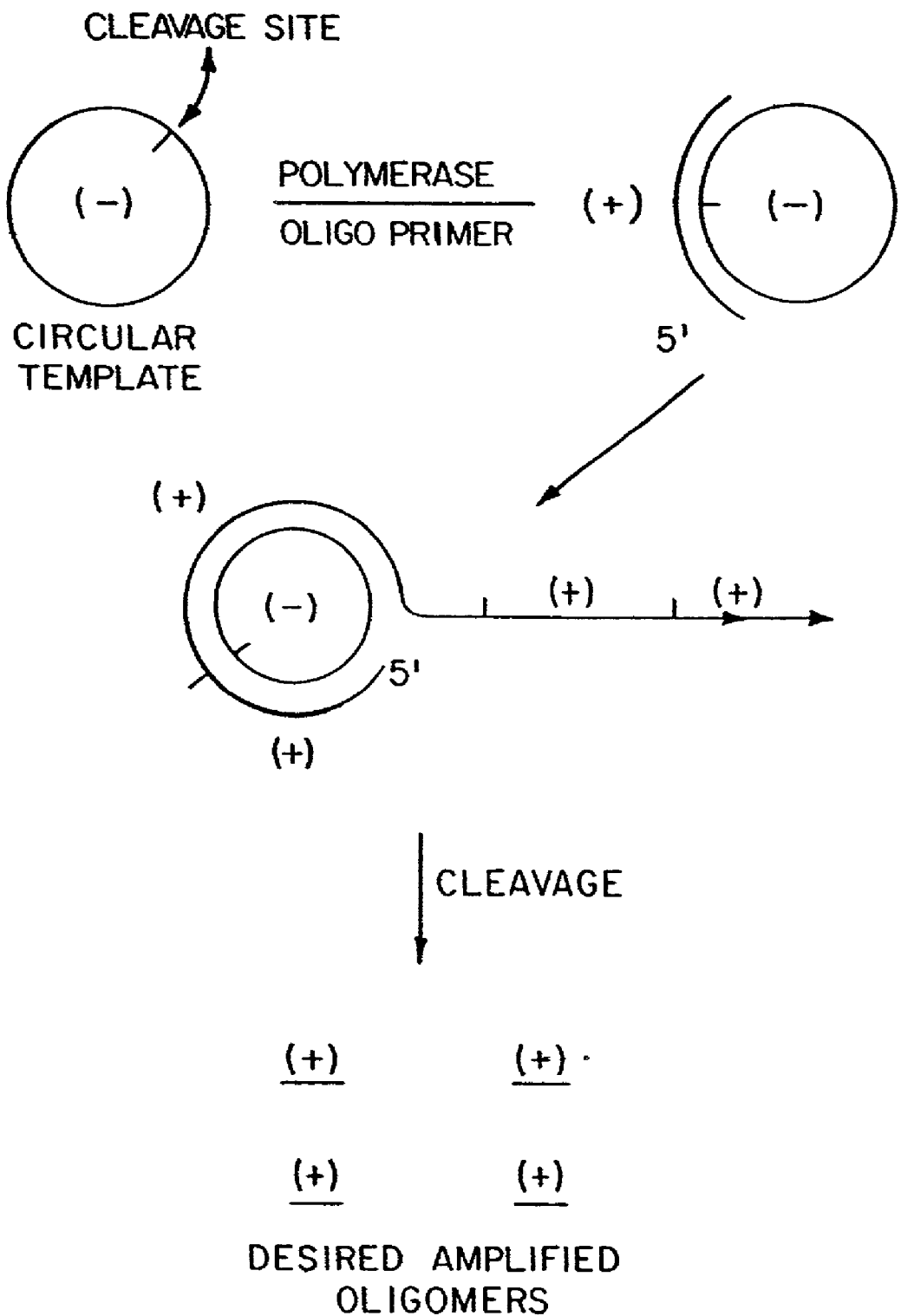
FIG. 1. Schematic of the rolling circle synthetic method of the present invention.
Figure 2:
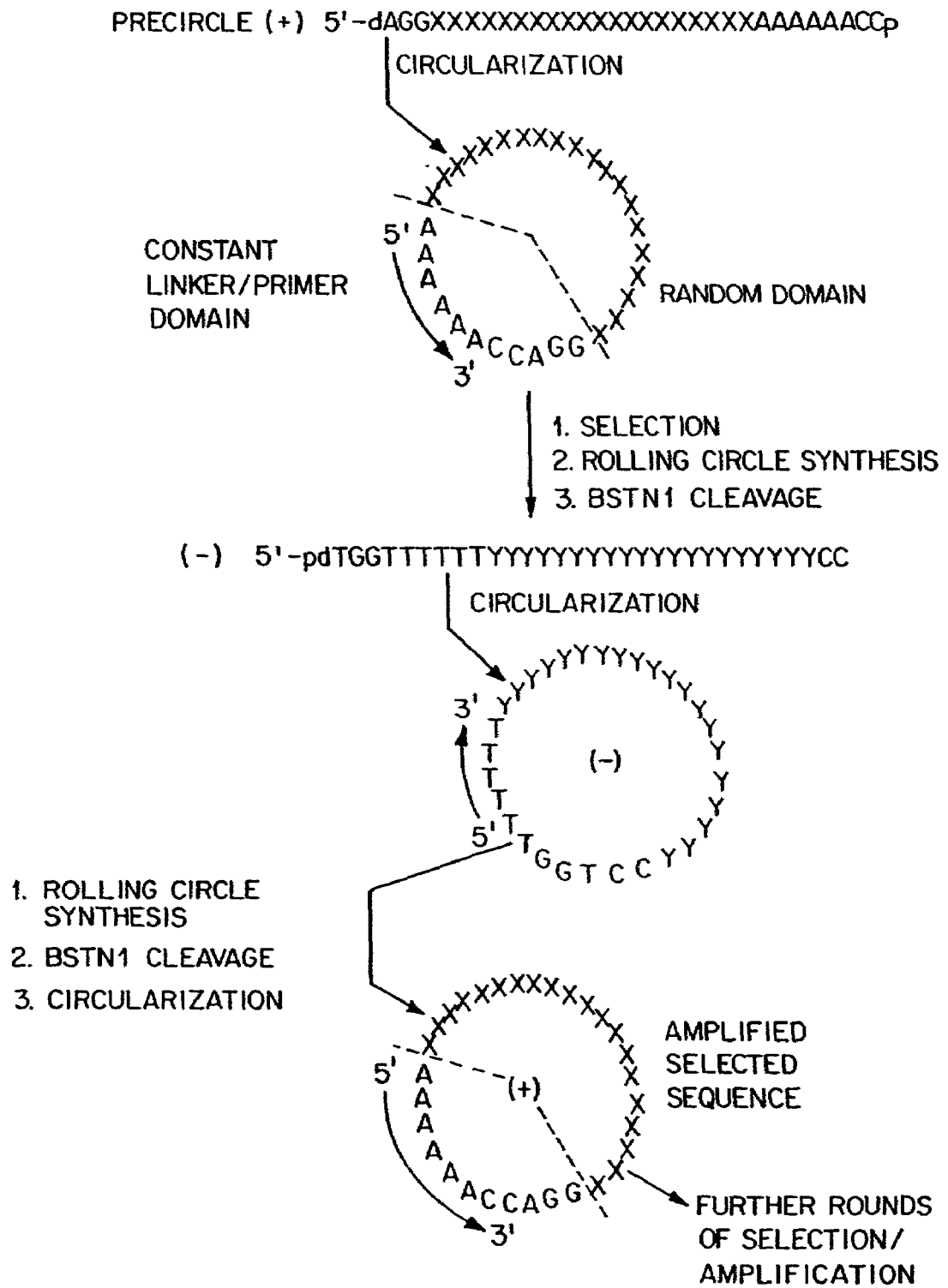
FIG. 2. Schematic of the selection and amplification of a circular oligomer (SEQ ID NO:23), (SEQ ID NO:24), (SEQ ID NO:25), AND (SEQ ID NO:26).

As used herein, desired "oligonucleotide" or "oligomer" refers to a sequence and length defined nucleic acid sequence or analog thereof as the desired product of the method of synthesis of the invention. A "multimer" or "oligonucleotide multimer" is a nucleic acid sequence containing multiple copies of an oligomer joined end to end. It is also referred to herein as a "concatemer". An "isolated circular template" refers to a circular nucleic acid sequence including a sequence complementary to the desired oligomer that is formed by circularization of a linear precircle. An "isolated oligonucleotide primer" refers to a nucleic acid sequence that is sufficiently complementary to a nucleic acid sequence of the circular template to bind to the isolated circular template and acts as a site for initiation of synthesis of a multimer. A "sense" sequence refers to a DNA sequence that encodes the information for a protein product. An "antisense" sequence refers to a DNA sequence complementary to a sense sequence that can bind to a sense sequence and inhibit its expression. An "effective" amount refers to an amount of a component effective to produce multimers longer than the circular template. A "drug lead" refers to a molecule that affects the function or structure of a target biomolecule and is used to design other pharmaceutical compounds having similar molecular shape or composition and function.

The present invention provides a novel, inexpensive, and simple method for the enzymatic construction of DNA and RNA oligonucleotides, or analogs thereof, having a specific sequence and well-defined ends. This synthetic method has several advantages over presently used techniques. First, the cost of oligomers produced by this method is lower than that of machine-synthesized or PCR-generated oligomers. Previous methods of amplifying a target nucleic acid sequence by circular replication methods used plasmid-sized DNA of several thousand nucleotides long. These previous amplification methods therefore produced sequences thousands of nucleotides in length even when the sequence of interest may only have been a few dozen nucleotides long. Thus, the amplification reactions would consume a large quantity of nucleotides while only a comparatively small amount of the nucleotides actually were components in the desired product.

Second, the method of the present invention is very simple and produces relatively pure oligomers. Because the method of the present invention does not incorporate unwanted nucleotides into the product molecules, the resulting oligonucleotides are easier to purify than those oligomers resulting from the prior art methods of replication. Third, the method does not consume costly organic solvents or other reagents, nor does it generate costly organic waste.

The method of the present invention can be applied to the synthesis of oligomers of about 4 to about 1500 bases in length. Herein, the synthetic method is referred to as the rolling circle method. This method involves the synthesis of single-stranded multimers complementary to a circular template.

The rolling circle synthetic method of the present invention advantageously uses readily available enzymes and a chemically prepared template to generate large amounts of a complementary oligonucleotide sequence. The method is advantageous because it uses only a small excess of nucleotide triphosphates, with the unused portions being recycled. The synthesis of RNA oligonucleotides requires no primer, and the synthesis of DNA oligonucleotides requires only substoichiometric amounts of primer. The method further produces oligomers with well-defined ends. The direct product of the reaction is reasonably pure, and can be further purified very easily using standard techniques, if desired.

This synthetic method is ideal for the large-scale preparation of desirable oligomers of DNA or RNA, such as the commercially sold hybridization primers, PCR primers, ribozymes, or any oligonucleotide that has been (or will be) shown to be of potential therapeutic value.

The rolling circle method is advantageous for many reasons including the following: (1) it allows optimum production of single-stranded oligonucleotides, unlike PCR and cloning; (2) it uses lower amounts of nucleotide units in the synthesis as compared to DNA synthesizers; (3) it requires only a catalytic amount of circular template and, optionally, primer (PCR to produce DNA oligomers requires stoichiometric amounts of primer); (4) it produces oligomers having clean, well-defined ends (unlike runoff transcription); (5) it is more efficient than single-stranded PCR amplification or runoff transcription because the polymerase enzyme is not required to associate and dissociate from the template in cycles; (6) expensive thermal cyclers and thermostable polymerases are not required; (7) it is possible to make DNA and RNA oligomers and analogs by this method using the same templates; (8) it is better suited for synthesis of circular oligonucleotides; (9) it allows for production in very large batches (hundreds or thousands of grams); (10) it does not use organic solvents or potentially toxic reagents; (11) fewer errors in the sequences are made (machine-synthesized DNA contains structural errors about every 50–100 bases or so, whereas enzyme methods make errors at the rate of about 1 in $10^4$–$10^8$ bases); and (12) the product generally needs relatively little purification (perhaps gel filtration or dialysis) because only small amounts of template and polymerase are needed to produce large amounts of oligomer. Thus, the present invention reduces, and in certain situations completely eliminates, difficult and expensive large-scale chromatographic purification.

The oligonucleotide products of the synthetic method may be either linear or circular. Circular oligomers have distinct advantages over linear oligomers. Circular DNA oligomers have a half-life of greater than about two days in human serum (as compared to a half-life of about twenty minutes for linear oligomers). See, for example, S. Rumney and E. Kool, *Angew. Chem., Intl. Ed. English*, 31, 1617 (1992).

Rolling Circle Synthesis of Oligomers

Overview. The method of the invention for the synthesis of DNA and RNA oligomers, and synthetically modified analogs thereof such as, for example, DNA phosphorothioates, RNA phosphorothioates, 2'-O-methyl ribonucleotides, involves these general steps: (1) providing an effective amount of a single-stranded oligonucleotide circular template and, in the case of DNA synthesis, an effective amount of a single-stranded oligonucleotide primer; (2) in the case of DNA synthesis, annealing the oligonucleotide primer to the oligonucleotide circular template to form a primed circular template; (3) combining the circular template (the primed template in the case of DNA synthesis) with an effective amount of at least two types of nucleotide triphosphates and an effective amount of a polymerase enzyme to form a single-stranded nucleotide multimer complementary to the circular oligonucleotide template; and preferably (4) cleaving of the single-stranded nucleotide multimer into the desired single-stranded oligonucleotides, i.e., oligomers, and optionally circularizing an oligonucleotide to form a circular product of DNA, RNA, or analog thereof.

The circular oligonucleotide template (sometimes referred to herein as a DNA nanocircle or vector) used for DNA or RNA oligonucleotide synthesis is composed of a single nucleotide strand containing naturally occurring or modified nucleotides. Preferably, the circular template contains DNA. The nucleotide sequence of the circular template is selected such that when the circular template is transcribed by a DNA or RNA polymerase, the desired DNA or RNA oligonucleotide will be produced.

It is notable that RNA synthesis requires no primer, and surprisingly there is no need for an RNA polymerase promoter sequence on the circular template. It is possible to use a primer for RNA synthesis according to the invention, but the synthetic reaction is preferably conducted in its absence. Similarly, an RNA promoter sequence may be present on the circular nanovector, but is preferably absent.

In a standard reaction, the synthetic method requires only very small amounts of the circular template, primer (for DNA synthesis), and polymerase enzyme, i.e., only an effective catalytic amount for each component. Surprisingly, no auxiliary proteins need to be added to assist the polymerase. A relatively larger amount, i.e., at least a stoichiometric amount, of the nucleotide triphosphates is required. After the reaction, the mixture consists of a large amount of the product oligomer and only small amounts of the template, primer, polymerase enzyme, and cleaving enzyme or reagent. Thus, the product is produced in relatively good purity, and can require only gel filtration or dialysis before use, depending on the application. Advantageously, the polymerase enzyme, the circular template, unreacted primer (in the case of DNA synthesis), and unreacted nucleotide triphosphates can be recovered for further use. A primer may be used in RNA synthesis according to the invention, but the synthetic reaction is preferably conducted in its absence. Similarly, an RNA promoter sequence may be present on the circular nanovector, but is preferably absent.

Construction of circular template. A circular oligonucleotide template which is complementary in sequence to the desired oligonucleotide product can be prepared from a linear precursor, i.e., a linear precircle. The linear precircle preferably has a 3'- or 5'-phosphate group and can contain any desired DNA or RNA or analog thereof, some examples of which are set forth below in connection with the descriptions of the rolling circle synthetic method. If the desired oligonucleotide product sequence is short (i.e., less than about 20–30 bases), a double or higher multiple copy of the complementary sequence can advantageously be contained in the template circle. This is generally because enzymes cannot process circular sequences of too small a size. Typically, a circular template has about 15–1500 nucleotides, preferably about 24–500, and more preferably about 30–150 nucleotides. It is to be understood that the desired nucleotide product sequence can either be a sense, antisense, or any other nucleotide sequence.

In the case of RNA synthesis, the circular oligonucleotide template is preferably constructed such that it contains a nucleotide sequence that encodes a biologically active RNA sequence, including but not limited to a catalytic RNA sequence, an antisense RNA sequence, or a "decoy" RNA sequence. The circular oligonucleotide template also preferably encodes a group that will be cleavable in the nucleotide multimer product. Where the oligonucleotide multimer product is RNA, cleavage of the multimer into monomeric products is conveniently effected autolytically by encoding a ribozyme and its cleavage site in the circular oligonucleotide template. DNA (and RNA) can be cleaved using, for example, a restriction enzyme, thus the oligonucleotide multimer can advantageously contain multiple copies of a restriction sequence encoded by the circular template. For example, the sequence 5'- . . . G A T C . . . -3' will be cleaved immediately before the G by the restriction enzyme Sau3AI. The product oligomers will thus contain the sequence on the 5' end. Alternately, a Type-II restriction site can be encoded within a hairpin forming sequence, so that the entire cleavable group will be removed by the cleaving enzyme, leaving only the desired sequence, as in Example 3. Another method, described by Szybalski et al., *Gene*, 40, 169 (1985), uses an added oligomer to direct a Type-II restriction enzyme to cleave at any desired sequence. A specific cleavable group might also be a natural DNA base, encoded by its complement in the circular template, which could be cleaved chemically, as in Examples 2 and 8, or it could be a modified base, as in Example 9 or 10.

Linear precircle oligonucleotides, from which the circular template oligonucleotides are prepared, can be made by any of a variety of procedures known for making DNA and RNA oligonucleotides. For example, the linear precircle can be synthesized by any of a variety of known techniques, such as enzymatic or chemical, including automated synthetic methods. Furthermore, the linear oligomers used as the template linear precircle can be synthesized by the rolling circle method of the present invention. Many linear oligonucleotides are available commercially, and can be phosphorylated on either end by any of a variety of techniques.

Linear precircle oligonucleotides can also be restriction endonuclease fragments derived from naturally occurring DNA sequence. Briefly, DNA isolated from an organism can be digested with one or more restriction enzymes. The desired oligonucleotide sequence can be isolated and identified by standard methods as described in Sambrook et al., *A Laboratory Guide to Molecular Cloning*, Cold Spring Harbor, N.Y. (1989). The desired oligonucleotide sequence can contain a cleavable site, or a cleavable site can be added to the sequence by ligation to a synthetic linker sequence by standard methods.

Linear precircle oligonucleotides can be purified by polyacrylamide gel electrophoresis, or by any number of chromatographic methods, including gel filtration chromatography and high performance liquid chromatography. To confirm a nucleotide sequence, oligonucleotides can be subjected to RNA or DNA sequencing by any of the known procedures. This includes Maxam-Gilbert sequencing, Sanger sequencing, capillary electrophoresis sequencing, automated sequencing, wandering spot sequencing procedure, or by using selective chemical degradation of oligonucleotides bound to Hybond paper. Sequences of short oligonucleotides can also be analyzed by plasma desorption mass spectroscopy or by fast atom bombardment.

The present invention also provides several methods wherein the linear precircles are then ligated chemically or enzymatically into circular form. This can be done using any standard techniques that result in the joining of two ends of the precircle. Such methods include, for example, chemical methods employing known coupling agents such as BrCN plus imidazole and a divalent metal, N-cyanoimidazole with $ZnCl_2$, 1-(3-dimethylaminopropyl)-3 ethylcarbodiimide HCl, and other carbodiimides and carbonyl diimidazoles. Furthermore, the ends of a precircle can be joined by condensing a 5'-phosphate and a 3'-hydroxyl, or a 5'-hydroxyl and a 3'-phosphate. Enzymatic circle closure is also possible using DNA ligase or RNA ligase under conditions appropriate for these enzymes.

One enzymatic approach utilizes T4 RNA ligase, which can couple single-stranded DNA or RNA. This method is described in D. C. Tessier et al., *Anal. Biochem.*, 158, 171–178 (1986), which is incorporated herein by reference. Under high dilution, the enzyme ligates the two ends of an oligomer to form the desired circle. Alternatively, a DNA ligase can be used in conjunction with an adaptor oligomer under high dilution conditions.

Preferably, the method of forming the circular oligonucleotide template involves adapter-directed coupling. Methods such as this are described in the Examples and in G. Prakash et al., *J. Am. Chem. Soc.*, 114, 3523–3527 (1992), E. T. Kool, PCT Publication WO 92/17484, and E. Kanaya et al., *Biochemistry*, 25, 7423–7430 (1986), which are incorporated herein by reference. This method includes the steps of: binding a linear precircle having two ends to an adapter, i.e., end-joining oligonucleotide; joining the two ends of the linear precircle; and recovering the single-stranded circular oligonucleotide template. The end-joining oligonucleotide is complementary to the two opposite ends of the linear precircle. The precircle and the adapter are mixed and annealed, thereby forming a complex in which the 5' and 3' ends of the precircle are adjacent. The adapter juxtaposes the two ends. This occurs preferentially under high dilution, i.e., no greater than about 100 micromolar, by using very low concentrations of adapter and precircle oligomers, or by slow addition of the adapter to the reaction mixture. Any suitable ligation chemistry can be used to join the ends of the linear precircle. For example, the ends can undergo a condensation reaction, wherein the 5'-phosphate is coupled to the 3'-hydroxyl group or the 3'-phosphate is coupled to the 5'-hydroxyl group, after about 6–48 hours of incubation at about 4–37° C. This occurs in a buffered aqueous solution containing divalent metal ions and BrCN at a pH of about 7.0. Preferably, the buffer is imidazole-HCl and the divalent metal is Ni, Zn, Mn, Co, Cu, Pb, Ca, or Mg. More preferably, the metals are Ni and Zn. Other coupling reagents that work include 1-(3-dimethylaminopropyl)-3 ethylcarbodiimide HCl, and other water-soluble carbodiimides, or any water-active peptide coupling reagent or esterification reagent.

The ends of the linear oligonucleotide precircle can alternatively be joined using a self-ligation reaction. In this method, the 5' end of the linear precircle is 5'-iodo- or 5'-tosyl- and the 3' end is 3'-phosphorothioate.

The circular oligonucleotide template can be purified by standard techniques although this may be unnecessary. For example, if desired the circular oligonucleotide template can be separated from the end-joining group by denaturing gel electrophoresis or melting followed by gel electrophoresis, size selective chromatography, or other appropriate chromatographic or electrophoretic methods. The isolated circular oligonucleotide can be further purified by standard techniques as needed.

Construction of primer. A primer is used to initiate rolling circle synthesis of DNA oligonucleotide multimers using the circular oligonucleotide template. The primer is generally short, preferably containing about 4–50 nucleotides, and more preferably about 6–12 nucleotides. This primer is substantially complementary to part of the circular template, preferably to the beginning of the desired oligomer sequence. A substantially complementary primer has no more than about 1–3 mismatches while still maintaining sufficient binding to the template. The 3' end of the primer must be at least about 80%, preferably 100%, complementary to the circular template. There is no requirement that the 5' end be complementary, as it would not have to bind to the template. Although a portion of the primer does not have to bind to the circular template, at least about 4–12 nucleotides should be bound to provide for initiation of nucleic acid synthesis. The primer can be synthesized by any of the methods discussed above for the linear precircle oligomer, such as by standard solid-phase techniques. See, for example, S. L. Beaucage et al., *Tetrahedron Lett.*, 22, 1859 (1981) (for DNA), and S. A. Scaringe et al., *Nucleic Acids Res.*, 18, 5433 (1990) (for RNA).

An effective amount of the primer is added to the buffered solution of an effective amount of the circular template under conditions to anneal the primer to the template. An effective amount of the primer is present at about 0.1–100 moles primer per mole of circular template, preferably 0.1–10. An effective amount of the circular template is that amount that provides for sufficient yield of the desired oligomer product. The effective amount of the circular template depends on the scale of the reaction, the size and sequence of circular template, and the efficiency of the specific rolling circle synthesis. Typically, the amount of the circular template is present at about a 1:5 to 1:20000 ratio with the amount of desired oligomer product, i.e., 1–5000 fold amplification, preferably 1:50 to 1:5000 ratio.

Conditions that promote annealing are known to those of skill in the art for both DNA-DNA compositions and DNA-RNA compositions and are described in Sambrook et al., cited supra. Once formed, the primed circular template is used to initiate synthesis of the desired oligomer or multimer.

Rolling circle synthesis. Rolling circle synthesis is initiated when nucleotide triphosphates and polymerase are combined with a circular oligonucleotide template. In the case of DNA synthesis, a primed circular template is utilized. At least two types of nucleotide triphosphate, along with an effective catalytic amount of the desired polymerase enzyme are used in the reaction. In DNA synthesis, the polymerase starts at the primer, elongates it, and continues around the circle, making the desired oligonucleotide product sequence. It continues past the starting point, displacing the synthesized DNA (or RNA) as it goes, and proceeds many times around the circle. The process is similar for RNA synthesis, except that the polymerase can initiate synthesis at any point on the circular template and without the aid of a primer. This amplified run-on synthesis produces a long single multimer strand which is made up of many end-to-end copies of the nucleotide sequence complementary to the circular template sequence, and contains multiple copies of the desired oligonucleotide product.

The size of the multimer product can be about 60 to $5 \times 10^6$ nucleotides in length. The method is capable of producing longer RNAs than other known synthetic methods, and results in higher yields. After cleavage, the RNA products produced by the present invention are more pure and have greater homogeneity at the 5' and 3' ends. Preferably, the RNA concatemers produced are more than 1000 nucleotides in length, more preferably in excess of 5000 nucleotides in length. For DNA synthesis, the multimer product is preferably about 500–100000 nucleotides in length.

The length of the multimer can be controlled by time, temperature, relative and absolute concentrations of enzyme, triphosphates, template, and primer. For example, longer periods of time, or lower concentrations of template, will tend to increase the average multimer length. The rolling circle method preferably uses only catalytic amounts of template, primer, and polymerase enzymes and stoichiometric amounts of the nucleotide triphosphates. Theoretically, the maximum size of multimer product is unlimited, however, often it is about $10^4$–$10^6$ nucleotides in length.

More preferably, the template concentration is about 0.1 µM to about 1 mM, the primer concentration is about 0.1 µM to about 1 mM, and the triphosphate concentration is about 1 µM to about 1000 mM. The preferred molar ratio of triphosphate(s) to template is about 50:1 to about $10^7$:1. The preferred molar ratio of primer to template is about 0.1:1 to about 100:1. These preferred amounts, i.e., concentrations and molar ratios, refer to amounts of the individual components initially provided to the reaction mixture.

The preferred reaction time for the rolling circle synthesis is about 1 hour to about 3 days. Preferably, the temperature of the reaction mixture during the rolling circle synthesis is about 20–90° C. For polymerase enzymes that are not thermally stable, such as DNA polymerase I and its Klenow fragment, and other nonengineered enzymes, the temperature of synthesis is more preferably about 20–50° C. For thermostable polymerases, such as that from *Thermus aquaticus*, the temperature of synthesis is more preferably about 50–100° C.

Oligomers may be radiolabeled if desired by adding one radiolabeled base triphosphate to the reaction mixture along with the unlabeled triphosphates at the beginning of the reaction. This produces multimer and product oligomers that are radiolabeled internally. For example, spiking the reaction mixture with α-$^{32}$P-dCTP will produce oligomers internally labeled with $^{32}$P at every C residue. Alternatively, a radiolabeled primer oligomer can be used, which results in a 5' radiolabeled multimer.

Preferred polymerase enzymes that effectuate the synthesis of a multimer in rolling circle synthesis have high fidelity, high processivity, accept single-stranded templates, and have relatively low exonuclease activity. For DNA polymerization, i.e., formation of DNA multimers, suitable enzymes include, but are not limited to, DNA Polymerase I, Klenow fragment of DNA Polymerase I, T7 DNA Polymerase (exonuclease-free), T4 DNA Polymerase, Taq Polymerase, and AMV (or MuLV) Reverse Transcriptase or closely homologous mutants. This group of enzymes is also preferred. More preferably, the enzyme for DNA polymerization is the Klenow enzyme.

For RNA polymerization, i.e., formation of RNA multimers, suitable enzymes include, but are not limited to, the phage polymerases and RNA Polymerase II. Preferred enzymes for RNA polymerization are T7, T4, T3, *E. coli* and SP6 RNA Polymerases, as well as RNA Polymerase II and RNA Polymerase III or closely homologous mutants. Particularly preferred enzymes are T7 and *E. coli* RNA polymerase.

Nucleotide triphosphates suitable for use in the synthetic method of the invention or for use in constructing the circular oligonucleotide template used in the method of the invention include are any that are used in standard PCR or polymerase technology. That is, any nucleotide triphosphate can be used in the rolling circle method that is capable of being polymerized by a polymerase enzyme. Suitable NTPs include both naturally occurring and synthetic nucleotide triphosphates. They include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP as well as the alpha-thiotriphosphates for all of the above, and 2'-O-methyl-ribonucleotide triphosphates for all the above bases. Other examples include 2'-fluoro-NTP and 2'-amino-NTP. Preferably, the nucleotide triphosphates used in the method of invention are selected from the group consisting of dATP, dCTP, dGTP, TTP, and mixtures thereof. Modified bases can also be used, including but not limited to, 5-Br-UTP, 5-Br-dUTP, 5-F-UTP, 5-F-dUTP, 5-propynyl dCTP, and 5-propynyl-dUTP. Most of these nucleotide triphosphates are widely available from commercial sources such as Sigma Chemical Co., St. Louis, Mo. Nucleotide triphosphates are advantageously used in the method of the present invention at least because they are generally cheaper than the nucleotide precursors used in machine synthesis. This is because the nucleotide triphosphates used herein are synthesized in as little as one step from natural precursors.

The rolling circle method of the present invention can also be used to produce double-stranded DNA oligomers, if desired. This is carried out by one of two methods. Rolling circle synthesis can be carried out separately on each of the complementary strands, and the multimer products combined at the end and then cleaved to give the desired duplex oligomers. Alternatively, two complementary circular templates can be placed in the reaction mixture simultaneously along with one primer for each strand (the primers are not complementary to each other). In this way, two primed circular templates are formed. The rolling circle synthesis can be carried out for both the complementary strands at the same time. That is, amplified run-on synthesis occurs with each primed circular template. This is possible because the two circular templates, although complementary to each other in sequence, cannot hybridize completely with each other as they are topologically constrained. As the complementary multimeric strands are formed, they combine to form the desired double-stranded multimer. This double-stranded multimer can then be cleaved to produce the desired double-stranded oligomers having well-defined ends.

The multimeric products generated from the synthetic method include linear or circular, single or double stranded DNA or RNA or analog multimer. The multimer can contain from about 60 to about $5 \times 10^6$ nucleotides, preferably about 500–100,000, or about 5–100,000 copies of the desired nucleotide sequences. Once formed, a linear multimer containing multiple copies of the desired sequence can be cleaved if desired into single copy oligomers having the desired sequence either while synthesis is occurring or after oligonucleotide synthesis is complete.

Cleavage of multimer into desired oligomers. The RNA or DNA oligonucleotide multimer can be cleaved into single-stranded oligomers by a variety of methods. Cleavage can be carried out during the rolling circle stage, i.e., as the multimer is formed, or after the polymerase reaction. Purification of the resultant oligomer can then be carried out if desired. Also, if desired, at this stage the synthesized oligomers can be cyclized into new circles for use as DNA/RNA binding agents, therapeutic or diagnostic agents, or as templates for the rolling circle synthesis of the complementary strand.

There are several techniques that can be used for the cleavage reaction. For example, restriction endonucleases can be used to cleave specific sequences that occur in the multimer. They can be used alone, or in some cases, with addition of a short DNA strand that aids in the reaction. The cleavage reaction also can be carried out using chemicals other than enzymes to effect cleavage of the multimer. For example, Maxam-Gilbert cleavage reagents can be used to cleave the strand at a base that occurs once between each oligomer.

In the case of RNA synthesis, the method preferably produces multiple copies of a short, sequence-defined RNA oligonucleotide (oligoribonucleotide). These RNA oligonucleotides are formed by cleavage of the long concatemeric repeating unit RNA product of rolling circle transcription. In a preferred embodiment, cleavage is autolytic, as where the monomeric units contain self-cleaving ribozymes. During the transcription reaction, the repeating RNAs self-cleave, reaching monomer length (i.e., they are cleaved to produce oligonucleotides containing only one copy of the desired RNA oligonucleotide sequence) after a sufficient length of time has elapsed. Typically the monomers are linear, but they may be cyclic, as where the monomer contains a hairpin-type ribozyme capable of intramolecular ligation. The resulting monomeric RNAs preferably include catalytically active ribozymes which can sequence-specifically cleave RNA targets in trans. As an example, a self-cleaving multimer would result from inclusion of the hammerhead sequence (A. C. Forster et al., *Cold Spring Harbor Symp. Quant. Biol.*, 52, 249 (1987)) in the RNA oligomer. Cleavage of the concatemeric RNA product can also be accomplished chemically or enzymatically, as by contact with a second molecule possessing site-specific endonuclease enzymatic activity. The second molecule can be, for example, a protein or a ribozyme acting in trans. For example, an RNA multimer could also be cleaved at any sequence by using a hammerhead sequence used in trans. See J. Haseloff et al., *Nature*, 334, 585 (1988). Another example of cleavage of an RNA multimer would be specific cleavage between G and A in the sequence 5'-GAAA, which can be achieved by the addition of the oligomer 5'-UUU and $Mn^{2+}$, following the method of Altman described in S. Kazakov et al., *Proc. Natl. Acad. Sci. USA*, 89, 7939–7943 (1992), which is incorporated herein by reference. RNA can also be cleaved using catalysts such as those described in J. Chin, *J. Am. Chem. Soc.*, 114, 9792 (1992), incorporated herein by reference, which have been attached to a DNA oligomer for sequence specificity. Alternatively, the enzyme RNase H can be used along with addition of a DNA oligomer, or base-specific RNases can be used.

For DNA, any one of several methods can be used as well. Single-stranded or double-stranded multimers can be cleaved into single-stranded or double-stranded multimers, respectively. For example, the multimer can be cut at a restriction enzyme site that has been incorporated into the sequence, leaving the restriction sequence in the oligomer product. This is demonstrated by Examples 1 and 7. Optionally, the remaining restriction site sequences can be removed from the oligonucleotide with an exonuclease or another restriction or nuclease enzyme. A hairpin sequence can be cut out using a Type II restriction enzyme. This is demonstrated by Example 3. The strand can be cut at any desired site using a Type II restriction enzyme and the method of Szybalski as described in W. Szybalski, *Gene*, 40, 169 (1985), and A. Podhadjska et al., *Gene*, 40, 175 (1985), which are incorporated herein by reference.

The Szybalski and Podhadjska et al. references concern the use of FokI restriction enzyme and an adapter oligonucleotide to cleave DNA at predetermined sites, i.e., they disclose a method of providing enzyme specificity by synthetic design. That is, these references disclose methods for cleaving of DNA, but not methods for amplifying DNA. The result of the method disclosed by these references is a double-stranded DNA molecule that contains a recognition sequence for class IIS restriction endonucleases.

If the nucleotide sequence of the desired oligomer does not contain all four bases, the fourth base can be added once per repeat and cleaved from the specifically by the Maxam-Gilbert methods, thereby producing oligomers with 3'- and 5'-phosphate end groups. This is done by encoding the complement of this fourth base, or any other cleavable nucleotide, either natural or modified, into the circular oligonucleotide template. Maxam-Gilbert methods are described in J. Sambrook et al., *Molecular Cloning*, 2nd ed.; Cold Spring Harbor Press, 1989, which is incorporated herein by reference.

Chemical cleavage of a nucleotide multimer at a natural nucleotide incorporated into the multimer is demonstrated by Examples 2, 8 and 11. Cleavage of a multimer at a modified nucleotide is demonstrated by Example 9. In this example, a base is modified with a photolabile group, such as an ortho-nitrobenzyl group, which is cleaved by light. Alternatively, an incorporated modified base can be used to cleave a multimer by specific chemical or redox signals, leaving the desired oligomers. For example, a modified purine such as N-7-deaza-7-nitro purine can be incorporated into the oligonucleotide multimer, permitting base-catalyzed cleavage at that site, as by the use of piperidine. Similarly, a N-7-methyl purine can be incorporated to provide a site for base-catalyzed cleavage of the multimer.

Another possibility for cleavage of the nucleotide multimers formed by the rolling circle synthesis of the present invention is the development of sequence-specific endonucleases. For example, S1 nuclease can be attached covalently to a linear or circular oligomer to give cleavage at specific sequences. RNase H can also be attached to such oligomers for cleavage of RNA.

Once the multimer is cleaved into the oligomer, the oligomer can be isolated by standard methods. The oligomer can also be circularized using the same methods described for circularizing a linear precircle into the circular template as described herein.

Figure 3:
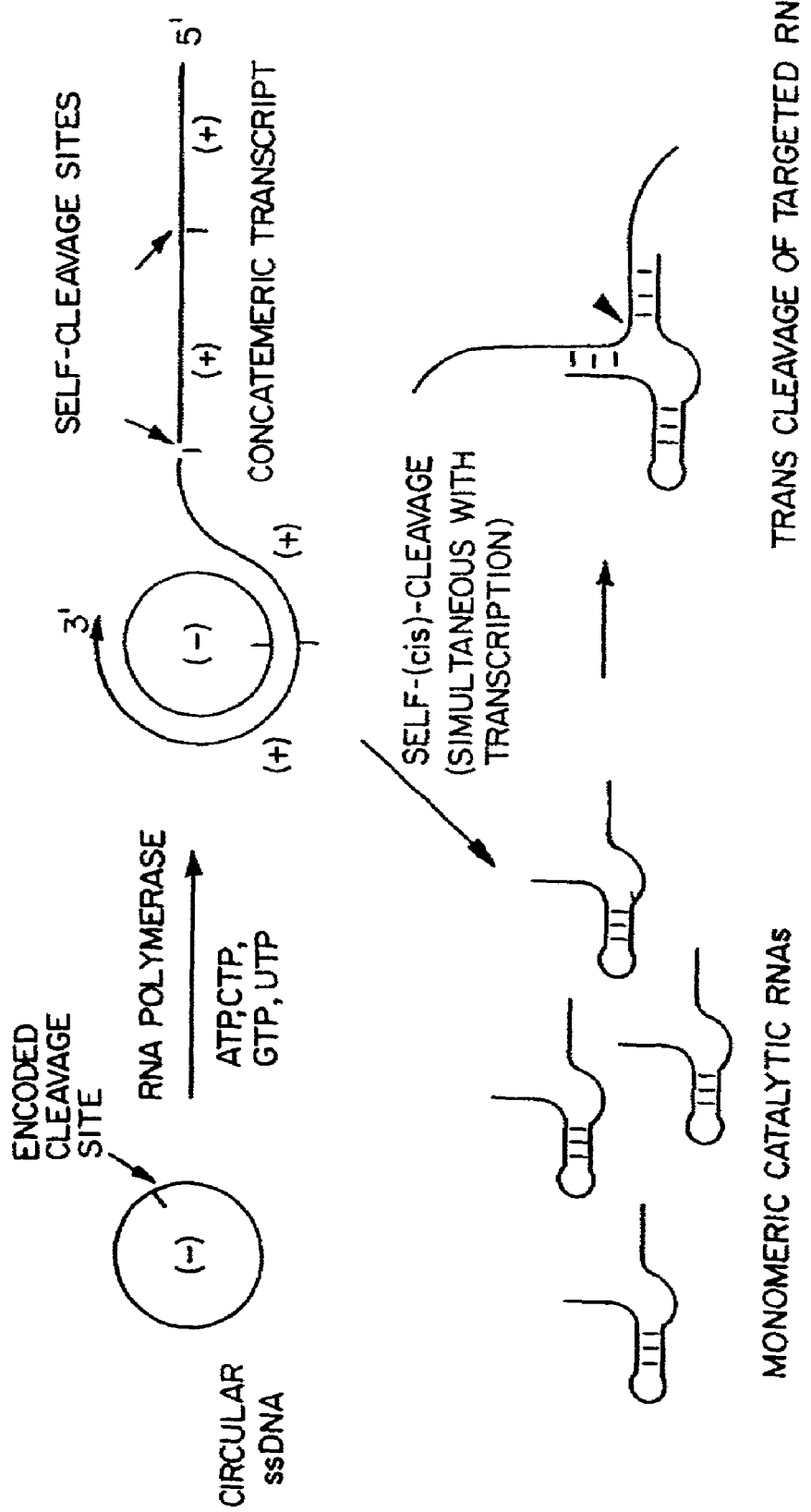
FIG. 3. Scheme for rolling transcription of a synthetic nanocircle vector encoding a catalytic RNA-cleaving domain and its own substrate; concatemers self-process to monomeric RNAs having the length of the circle.

RNA oligonucleotide products. The RNAs produced by the present method are preferably catalytic RNAs that cleave nucleic acid sequences, such as ribozymes. Preferred ribozymes include hairpin ribozymes, hammerhead-motif ribozymes, and hepatitis delta catalytic RNAs. The catalytic RNAs produced by the present invention are preferably capable of cleaving disease-related RNAs, such as, for example, bcr-abl mRNA (Reddy et al., U.S. Pat. No. 5,246, 921, issued Sep. 21, 1993, incorporated herein in its entirety). Hammerhead-motif catalytic RNAs can readily be adapted to cleave varied RNA sequences (O. C. Uhlenbeck, *Nature*, 328, 596–600 (1987); J. Haseloff et al., *Nature*, 344, 585–591 (1988); R. H. Symons, *Ann. Rev. Biochem.*, 61, 641–671 (1992); D. M. Long et al., *FASEB J.*, 7, 25–30 (1993)), which references are incorporated herein in their entirety) by altering the sequence of the noncatalytic, substrate-binding domain of the RNA encoded by the circular DNA template. Such modifications to the sequence of the substrate-binding domain are easily made during synthesis of the circular DNA template thereby permitting the method of the invention to produce any desired diagnostically or biologically useful RNA. Monomeric catalytic RNAs can act not only in cis fashion (intramolecularly) but also in trans to cleave other target RNAs (FIG. 3) (Reddy et al., U.S. Pat. No. 5,246,921, issued Sep. 21, 1993; Cech et al., U.S. Pat. No. 5,354,855, issued Oct. 11, 1994; Cech et al., U.S. Pat. No. 5,093,246, issued Mar. 3, 1992; and Cech et al., U.S. Pat. No. 4,987,071, issued Jan. 22, 1991, all of which are incorporated herein in their entirety). Catalytic RNAs produced by the invention include RNAs possessing any desired enzymatic activity, including but not limited to endo- or exo-nuclease activity, polymerase activity, ligase activity, or phosphorylase/dephosphorylase activity.

Self-cleaving monomeric ribozymes produced by rolling circle transcription of circular DNA templates carry "stringency clamps" that may serve to increase their substrate sequence specificity. The cleavage site in the concatemeric transcript is formed by intramolecular hybridization. Self-cleavage typically results in a monomeric product in which the 5' and 3' ends are folded back onto the chain and duplexed in a hairpin configuration. To cleave in cis, binding of the substrate-binding sequences of the ribozyme monomer to the substrate must successfully compete with an intramolecular complement of the substrate-binding sequences. The stringency clamps also substantially reduce the susceptibility of the RNA oligonucleotides to degradation by various agents present in media, serum and the like.

Intracellular RNA synthesis. Synthesis of RNAs from circular oligonucleotide templates, preferably DNA nanocircles, can be performed in solution (i.e., in vitro), or inside a cell. Suitable cells include cells of bacteria, plants, or animals. The cell can, for example, be in cell culture (ex vivo), or it can be present in a living whole organism, such as a plant or animal (in vivo). Preferably in vivo synthesis of RNA takes place inside a mammal, more preferably a human.

In order for RNA transcription of the circular DNA templates to take place inside a cell, the circular DNA template must be introduced into a cell, and the cell must contain or be supplied with an effective RNA polymerase and the required NTPs. The circular template can be introduced into or taken up by the cell using any convenient method, such as direct injection, electroporation, heat-shock, calcium phosphate treatment, lipid-mediated or cation-mediated delivery such as the use of polyethyleneimine, lipofectin, lipofectamine-plus (Gibo-BRL), and the like. Cellular binding, uptake, and intracellular distribution of circular decoy DNA molecules bearing hairpin or dumbbell structures was demonstrated by L. Aguilar et al., *Antisense & Nucl. Acid Drug Devel.*, 6, 157–163 (1996). Incubation with cationic lipids increases their uptake into normal hematopoietic cells. T. Albrecht et al., *Ann. Hematol.*, 72, 73–79 (1996); S. Capaccioli et al., *Biochem. Biophys. Res. Commun.*, 197, 818–825 (1993). Polyaminolipids have been shown to improve cellular uptake of oligonucleotides. J. K. Guy-Caffey et al., *J. Biol. Chem.*, 270, 31391–31396 (1995).

Because of their small size, the DNA circular vectors used as synthetic templates in the method of the invention are more easily introduced into cells than typical plasmid or viral vectors. Optionally, circular DNA templates can be chemically modified to improve properties such as cell permeability, provided that the modifications do not inhibit transcription. Examples of chemical modifications that improve cellular uptake include those designed to increase membrane permeability of the circular vector, such as covalent attachment of cholesterol or other suitable lipid, and those designed to induce receptor-mediated uptake by attaching a small ligand molecule to the circular DNA. Furthermore, small circular DNA vectors would be expected to have normal drug-like pharmacokinetics, in that the circular DNA vectors would be taken up, degraded, and excreted, in contrast to plasmid or viral vectors that may disrupt the normal functioning of a recipient cell by integrating into its genome. The small circular DNAs are orders of magnitude more resistant to degradation than linear DNAs, and many orders of magnitude more resistant than RNAs. Thus, circular DNA templates are expected to reach cells in greater numbers than RNA oligonucleotides for a given dosage and, once in contact with RNA polymerases, are expected to yield amplified amounts of RNA. High levels of RNA oligonucleotides inside the cell are thus achievable.

Intracellular production of the RNA transcripts from the circular oligonucleotides can be accomplished using RNA polymerase endogenous to the cell, or, optionally, the cell can be transformed with a gene encoding a desired RNA polymerase, such as T7 or *E. coli* RNA polymerase, operably linked to a promoter. Once inside the cell, the circular DNA template is transcribed to produce biologically active RNAs.

Any suitable cell or cell line can be used for exogenous transfection with the circular oligonucleotide template of the invention. Alternatively, cells explanted from a patient can be used.

In vivo production of the desired RNA transcript inside a living whole organism such as a plant or an animal, preferably a human, can be accomplished by introducing the exogenously transfected cells described in the preceding paragraph into the organism. Alternatively, in situ or endogenous transfection can be accomplished by directly contacting cells in the organism with an amount of the circular DNA nanovector template and, optionally, co-introducing into the cell a gene encoding a suitable RNA polymerase, such as T7 or *E. coli* RNA polymerase. Preferably, the polymerase gene is operably linked to a promoter. More preferably, it is present on a vector, such as a retrovirus, an adenovirus, a vaccinia vector, a plasmid, or the like.

The circular DNA template is administered to the mammal such that it is taken up by a cell of the mammal. The circular DNA template can be targeted to particular mammalian cells or to bacterial cells, preferably pathogenic bacterial cells, in a mammal or other animals, such as a bird or other vertebrates. Administration can be via direct injection, for example, at a tumor site, or by subcutaneous, intramuscular, or intravenous injection. Other modes of administration include but are not limited to inhalation, intranasal administration, ocular administration, site-specific incubation or infusion. One of skill in the art will appreciate that the present method is not dependent upon any particular mode of administration; rather, the mode of administration selected is governed upon the therapeutic effect desired.

Oligonucleotide therapies. The method of the invention contemplates treating a disease in a mammal, preferably a human, by administering to the mammal a small circular DNA template of the invention such that it is transcribed in vivo by rolling circle transcription of circular DNA template to produce therapeutic DNAs and RNAs. Advantageously, the circular DNA template can be systemically administered to treat bacterial and/or viral infections in mammals, particularly drug-resistant infections. RNAs suitable for therapeutic use are biologically active RNAs that include, but are not limited to, catalytic RNAs, (for example, a hammerhead-motif ribozyme), antisense RNAs sequence, or "decoy" RNAs. Catalytic RNAs can function, for example, as sequence-specific endoribonucleases, polymerases (nucleotidyltransferases), or dephosphorylases (acid phosphatases or phosphotransferases). Cech et al., U.S. Pat. No. 5,354,855, issued Oct. 11, 1994, incorporated herein in its entirety. Preferably, the therapeutic RNAs produced include catalytic ribozyme monomers or concatemers that cleave a target disease-associated RNA in trans. A target RNA may, for example, be a mutated mRNA or the RNA of a retrovirus, such as HIV-1.

Alternatively, therapeutic RNAs can first be exogenously produced by transcription of the circular DNA template, then administered directly to the human using any convenient method such as those described herein, such that they have a therapeutic effect on the human. The exogenously synthesized therapeutic RNAs may be chemically modified prior to administration to the human so as to render them less sensitive to enzymatic degradation. Alternatively, modified rNTPs that render the resulting RNA transcripts less sensitive to intracellular degradation may be supplied during synthesis.

RNA molecular weight standards. The invention further provides a population of RNA molecules produced by the rolling circle synthetic method of the invention for use as molecular weight standards. The RNA molecular weight standards are preferably provided in a kit that contains an RNA "ladder" and, optionally, instructions for use. An RNA ladder is composed of RNA molecules of increasing size in defined increments. Size is measured by nucleotide length (number of nucleotides). Preferably, the RNA molecules of an RNA ladder range in size from about 50 nucleotides to about 10000 nucleotides. The RNA molecular weight standards may be conveniently packaged in separate populations of short, medium length, or long RNA molecules. For example, a kit can contain a ladder composed of smaller molecular weight standards (for example, from about 50 to about 500 nucleotides) or a ladder composed of larger molecular weight standards (for example, from about 500 nucleotides to 10000 nucleotides), or both. Each ladder preferably contains RNA molecules of about 4 to 50 different molecular weights, preferably about 10 to 20 different molecular weights in even increments.

The increment size is determined by the length of the oligonucleotide encoded by the circular DNA template used to synthesize the ladder; each monomeric RNA unit (i.e., a single copy of the oligonucleotide encoded by the circular template) represents one increment. The circular DNA template preferably encodes at least one copy of a self-cleaving ribozyme oligonucleotide, and length of the ultimate transcript is controlled by adjusting the amount of time the reaction is allowed to proceed. For example, a 100 mer DNA circle can, under the appropriate conditions and after a period of time sufficient to permit partial autolytic processing of the multimeric transcript, produce well-defined RNA fragments that are 100, 200, 300, etc. nucleotides in length. Longer reaction times result in an increasing level of self-cleavage and yield populations of RNA products tending to be shorter in length (i.e., containing fewer copies of the sequence encoded by the circular template). The ladder-generating reaction is stopped or quenched after the desired amount of time has elapsed by adding an effective amount of denaturant such as formamide, urea, or ethylenediaminetetraacetic acid (EDTA).

The kit provided by the invention can contain the desired DNA nanocircle template and a suitable buffer, thus enabling the kit user to perform the reaction to generate the RNA ladder. The user can then detectably label the RNAs as desired during synthesis by supplying the appropriate nucleotides for incorporation into the RNA transcript. Alternatively, the kit provided by the invention can contain the RNA ladder itself, which may be in solution, preferably frozen in a quenching buffer, or in powder form (as by lyophilization). In a preferred embodiment, the RNA ladder provided by the kit is detectably labeled such that each RNA size increment is detectable. The detectable label can be a radioactive label, an enzymatic label, a fluorescent label, or the like.

The following examples are offered to further illustrate the various specific and preferred embodiments and techniques. It should be understood, however, that many variations and modifications may be made while remaining within the scope of the present invention.

EXAMPLES

Example 1

Synthesis of a 34-nt DNA Oligomer

A linear 34-nucleotide (34-nt) precircle DNA oligonucleotide having the sequence (SEQ ID NO:1):

5'-pAAAGAAGAGG GAAGAAAGAA AAGGGG TGGA AAAG, was machine synthesized on a Pharmacia LKB Gene Assembler Plus using standard β-cyano-ethyl phosphoramidite chemistry as disclosed in S. L. Beaucage et al., *Tetrahedron Lett.*, 22, 1859 (1981), which is incorporated herein by reference. This precircle template is complementary to the desired oligomer. The sequence of the desired oligonucleotide product is (SEQ ID NO:2):

5'-pTTTTCCACCC CTTTTCTTTC TTCCCTCTTC TTTC, which has an MnlI enzyme cleavage site at its end. Using this enzyme, a polymeric version of this oligomer, i.e., a multimer, can be cut into oligomers having this sequence. A ligation adaptor, 5'-TTTTCTTTCTT (SEQ ID NO:27), was also machine synthesized, as described above. This was also used as the primer oligomer.

The precircle template (100 nmol) was cyclized into the template circle (SEQ ID NO:3):

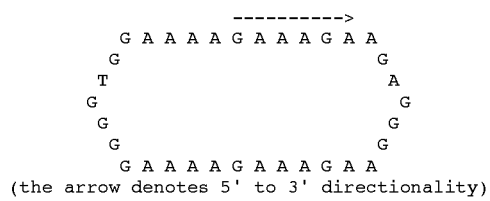

(the arrow denotes 5' to 3' directionality)

using the following method with the ligation adaptor to align the ends. The precircle template and ligation adaptor oligomers were placed in a 1-mL syringe in a programmable syringe pump. The oligomers were at 50 µM concentration. The syringe was connected by a tube to a 5-mL reaction vial. A reaction buffer, composed of 20 mM EDC, 20 mM mg Cl2, and 50 mM 2-(N-Morpholino)ethane-sulfonic acid (MES) buffer (obtained from Sigma Chemical Co., St. Louis, Mo.) was placed in the vial. The syringe pump was then used to deliver the adaptor to the reaction vial slowly (over a period of 24 hours at 4° C.). This method kept the effective concentrations very low, maximizing cyclization relative to dimerization. At the same time, it allowed the reaction to be carried out in a relatively small volume, making recovery of the product easier. Alternatively, the circular template can be constructed using BrCN/imidazole and a divalent metal in a manner analogous to that disclosed in G. Prakash et al., *J. Am. Chem. Soc.*, 114, 3523–3527 (1992), and E. Kanaya et al., *Biochemistry*, 25, 7423–7430 (1986). Gel electrophoresis was used to separate the circular product from starting material. This separation step was optional. Further experimental details of an analogous cyclization step are outlined in Example 5.

For the rolling circle synthesis of the desired oligonucleotide product, the template circle (10 µM), primer (10 µM), dATP (2 mM), dTTP (2 mM), and dGTP (2 mM) were dissolved in a buffer containing 34 mM tris(hydroxymethyl) aminomethane (Tris-HCl) (pH 7.4, obtained from Sigma Chemical Co., St. Louis, Mo.), 3.4 mM $MgCl_2$, 2.5 mM dithiothreitol, 25 µg/ml bovine serum albumin, and 20% polyethylene glycol 8000 (PEG 8000). The Klenow fragment of DNA Polymerase I (2 units, obtained from United States Biochemical, Cleveland, Ohio.) was also added. The reaction was allowed to proceed for 1 hour at 0° C., and then for 6 hours at 37° C. Further experimental details of an analogous rolling circle synthesis step are outlined in Example 6. Gel electrophoresis of a small aliquot of this solution showed very light bands corresponding to the template and very dark slow bands corresponding to the nucleotide multimers produced. The sequence of these multimers is as follows (SEQ ID NO:4):

```
                          ↓
5'...TTTTCCACCC CTTTTCTTTC TTCCCTCTTC TTTCTTTTCC

↓
ACCCCTTTTC TTTCTTCCCT CTTCTTTCTT TTCCACCCCT

↓
TTTCTTTCTT CCCTCTTCTT TCTTTTCCAC CCCTTTTCTT

↓
TCTTCCCTCT TCTTTCTTTT CCACCCCTTT TCTTTCTTCC

↓
CTCTTCTTTC TTTTCCACCC CTTTTCTTTC TTCCCTCTTC
↓
TTTC...-3'
(arrows mark MnlI cleavage sites)
```

To cleave the product multimers into the desired oligonucleotide product, 10 units of MnlI restriction enzyme (available from New England Biolabs, Beverly, Mass.) can be added. Incubation at 37° C. results in cleavage of the multimers into a single product, which would be seen as a very dark band by gel electrophoresis. This dark band is the desired 34-base oligomer. Further experimental details for an analogous cleavage step are outlined in Example 7.

If desired, the oligomer could be further purified. Gel filtration should easily remove unreacted oligomers and the two proteins. If removal of the very small amount of circle template is desired, gel electrophoresis or affinity chromatography will accomplish this.

The oligonucleotide product can also be converted into circular form if desired, using the method described in G. Prakash et al., *J. Am. Chem. Soc.*, 114, 3523–3527 (1992), which is incorporated herein by reference. This method will work using the crude oligomer i.e., unpurified product, from the reaction. These 5'-phosphorylated circle precursors are hybridized with short complementary DNA templates, which bring the reactive 3'-hydroxyl and 5'-phosphate ends adjacent to one another. These ends are ligated using BrCN/ imidazole/$Ni^{2+}$, in a manner analogous to the method described in G. Prakash et al. and E. Kanaya et al. It is worth noting that this second circle could be used as a template for rolling circle synthesis of the precircle template oligomer, eliminating the need for any machine synthesis in the long term.

Example 2

Synthesis of a Linear Oligomer of Sequence $dT_{12}$

The circular template used for the synthesis of the sequence 5'-pdTTTTTTTTTT TTp (SEQ ID NO:7) is (SEQ ID NO:5):

```
      A A A A A A A A A C
    A                     A
    A                     A
    A                     A
      C A A A A A A A A A
```

The precircle sequence used to synthesize this circular template is 5'-dCAAAAAAAAA AAACAAAAAA AAAAAAp (SEQ ID NO:5). The primer/adaptor sequence is 5'-dTTTTGTTT. The circular template is constructed from the linear precircle and the adaptor using BrCN/imidazole under high dilution. Alternatively, the circular template can be constructed using 1-(3-dimethylaminopropyl)-3 ethylcarbodiimide HCl under the conditions described in Example 1.

For the rolling circle synthesis of the desired oligonucleotide product, only two triphosphates, dTTP and dGTP, are used following the conditions described in Example 1. Workup can be done by polyethylene glycol (PEG) precipitation. The product formed is the multimer 5' . . . GTTTTTTTTT TTTGTTTTTT TTTTTTGTTT TTTTTTTTT . . . (SEQ ID NO:6). The pellet can be resuspended in a Maxam-Gilbert G buffer. This suspension is treated by the Maxam-Gilbert "G" reaction. The Maxam-Gilbert "G" reaction is described in J. Sambrook et al., *Molecular Cloning*, 2nd ed.; Cold Spring Harbor, 1989, Chapter 13, which is incorporated by reference. The resultant desired oligomer has the sequence 5'-pdTTTTTTTTTT TTp (SEQ ID NO:7).

Example 3

Synthesis of dAAGAAAGAAA AG

A schematic of the synthesis of the linear sequence 5'-pdAAGAAAGAAA AG (SEQ ID NO:8), is shown below in Scheme II. In this example, a partially self-complementary sequence was included in the circular template. No adapter was needed for cyclization because the molecule is self-complementary. The method for cyclization used is described in G. W. Ashley et al., *Biochemistry*, 30, 2927 (1991), which is incorporated herein by reference. The multimer was synthesized as described in Examples 1 and 5. The multimer product can be cleaved with BsmAI restriction enzyme, which removes the hairpins, leaving the desired product oligomer as the 5'-phosphate. Note that the product oligomer contains no restriction enzyme sequences.

Scheme II precircle
5'-AGACGAAGAT CAAACGTCTC TAAGACTTTT CTTTCTTAGp self-templated (no adapter needed)  (SEQ ID NO:22)

ligation using the
method disclosed in
G.W. Ashley et al.
↓

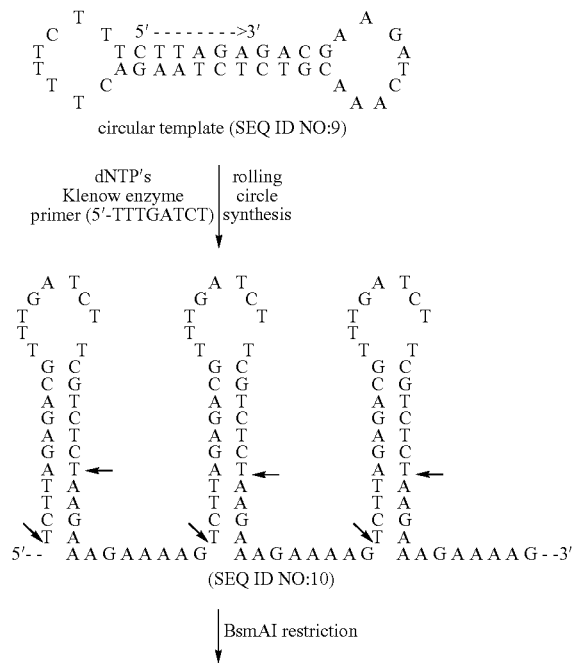
circular template (SEQ ID NO:9)
(SEQ ID NO:10)
Desired Oligomer (SEQ ID NO:11)
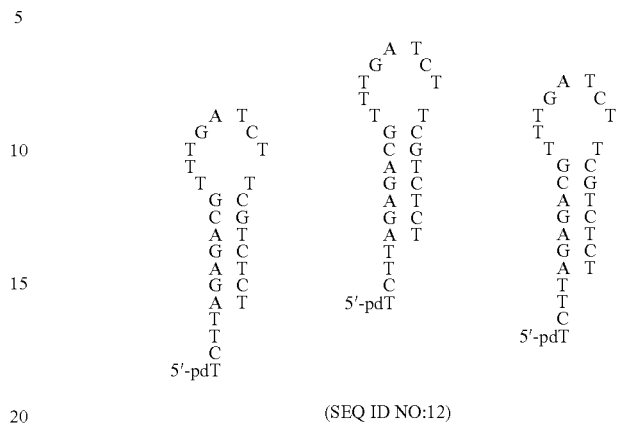
(SEQ ID NO:12)
Example 4
Synthesis of Additional Template
A circle very similar to that in Example 1 was constructed. In this example, the circular product was used as a template to produce more of the original template. A schematic illustration of this synthetic procedure is shown below in Scheme III.
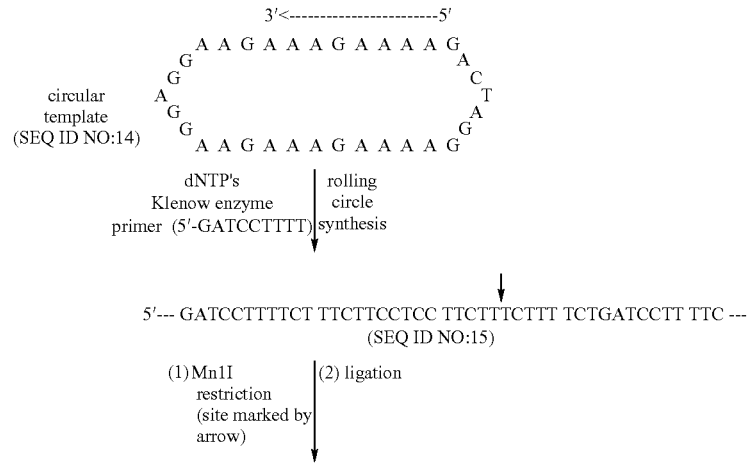

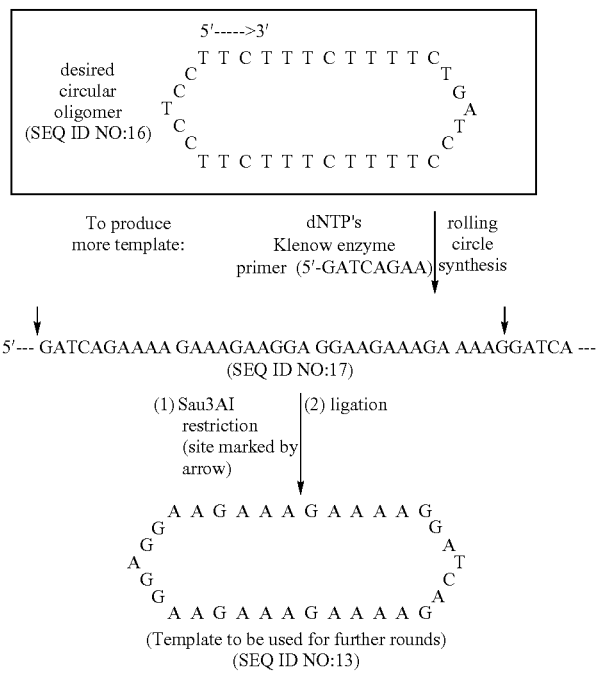

Example 5

Closure of Linear Oligomer into Circular Form

DNA oligomers were synthesized on a Pharmacia LKB Gene Assembler Plus using standard β-cyanoethyl phosphoramidite chemistry as described in S. L. Beaucage et al., *Tetrahedron Lett.*, 22, 1859 (1981), which is incorporated herein by reference. The oligomer to be ligated (34-mer) had the sequence 5'-pAAAAGAAAGA AGGAGGAAGA AAGAAAAGGAT CAG (SEQ ID NO:18), and was 5' phosphorylated using Phosphate-On™m reagent (available from Cruachem, Sterling, Va.), whereas the shorter adaptor oligomer (8-mer) was left with hydroxyl termini. The template 34-mer was designed to include the single-stranded version of a double stranded restriction enzyme site such as that for Sau3AI (GATC). The adaptor 8-mer had the sequence 5'-TTTTCTCG, and was designed to be complementary to 4 bases at each terminus of the template 34-mer, thus bringing the ends into proximity upon binding.

The 5'-phosphorylated oligomers were chemically ligated to produce primarily DNA circles using EDC. A typical preparative reaction contained up to 100 μM target and 100 μM adaptor in a 10 mL reaction containing 200 mM EDC, 20 mM MgCl$_2$, and 50 mM 2-(N-Morpholino)ethanesulfonic acid (MES) buffer (pH 6.1, obtained from Sigma Chemical Co., St. Louis, Mo.). To keep the concentration of target oligomer low enough to favor intra-molecular reaction (circularization) over intermolecular reaction (multimerization), up to 1 μmol of prescribe oligomer dissolved in 1 mL of water was added to the other reagents (9 mL at 10/9 final concentration) at 4° C. over a period of 50 hours with stirring, using a syringe pump to carry out the addition. Reaction was continued for an additional 16–24 hours after addition was complete to promote maximal reaction.

Products were recovered by precipitation with 30 mL of ethanol in the presence of 100 μg of rabbit muscle glycogen carrier (Sigma Chemical Co., St. Louis, Mo.) and purified by preparative gel electrophoresis. Yields were calculated from absorbance measurements at 260 nm using extinction coefficients calculated by the nearest neighbor method.

Example 6

Synthesis of Single-stranded Multimers Complementary to a Circular Template DNA circles synthesized as described in Example 5 were used to direct the primed synthesis of complementary multimers by the rolling circle method. The primer oligonucleotide was annealed to the template circle in a reaction consisting of 1 μL of 100 μM template circle, 1 μL of 100 μM primer, and 2 μL of 5×Klenow reaction buffer (335 mM Tris(hydroxymethyl)aminoethane)-HCl (pH 7.4), 34 mM MgCl$_2$, 25 mM dithiothreitol, and 250 μg/ml bovine serum albumin). This mixture was cooled from 25° C. to 4° C. over several hours and then either kept on ice or frozen for future use. The reaction mixture contained the annealing reaction (4 μL), 4 μM of 50% polyethylene glycol 8000 (PEG 8000), 1 μL mixed deoxyribonucleotide triphosphates (specifically this was a mixture of dATP, dTTP, dGTP, dCTP (sodium salts) each at 2 mM), and 1 μM of 2 U/μL Klenow fragment of DNA Polymerase I (United States Biochemical) and was assembled on ice. Synthesis was allowed to proceed for 1 hour at 0° C. and then for 6 hours at 37° C. Product multimers were recovered as a pellet by centrifugation at 10,000 rpm for 10 minutes at room temperature in a microcentrifuge.

Example 7

Enzymatic Cutting of Linear Multimers into Oligomers

Single-stranded multimers containing a restriction enzyme site were cleaved using the appropriate restriction enzyme at a temperature that allowed transient hybridization between restriction enzyme sites in either an intermolecular or intramolecular fashion to create a double stranded site. In the case of multimers containing the recognition site for Sau3AI, digestion of the multimers produced from the standard synthesis reactions described in Examples 5–7 was done as follows.

The PEG 8000 precipitate was dissolved in 10 μL reaction buffer (as recommended by the manufacturer of Sau3AI) containing 1 unit of Sau3AI (New England Biolabs, Beverly, Mass.). Digestion was allowed to proceed overnight at 25° C. and products were analyzed by electrophoresis on a 20% polyacrylamide, 8 M urea denaturing gel. DNA was visualized by staining with methylene blue (Sigma Chemical Co.). The principal product had gel mobility identical to that of an authentic 34-mer, and had the sequence 5'-pdGATC-CTTTTCT TTCTTCCTCC TTCTTTCTTT TCT (SEQ ID NO:19).

Example 8

Chemical Cleavage of Linear Multimers

This method can be used when the desired oligomer contains only one, two, or three different bases. An unused base is then incorporated into the multimer once at the end of every oligomer unit. For example, if the desired oligomer contains only C, A, and G bases, then the corresponding circular template will contain only the complementary G, T, and C bases; a single A base will be added at the site between the start and end of the desired sequence. The multimer transcript will consist of repeats of the desired sequence separated by a single T at each unit. Submitting this multimer to Maxam-Gilbert "T" reaction/cleavage conditions, as disclosed in J. Sambrook et al., *Molecular Cloning*, 2nd ed., Chapter 13; Cold Spring Harbor Press, 1989, incorporated herein by reference, results in cleavage of the chain at each T, with loss of the T base, and leaving the desired oligomers with phosphates on the ends.

Linear multimer can be isolated by pelleting from the transcription reaction as described above in Example 6. To confirm success of the rolling circle reaction, a small portion can be checked for length on an analytical scale by agarose gel electrophoresis, using markers of known length. Cleavage is then carried out on the isolated multimer, using standard Maxam-Gilbert-type conditions (scaling up as necessary for preparative amounts of DNA). The product oligomer can be isolated by ethanol precipitation.

For example, the sequence 5'-dCGAGAAAAGA AAGAAGGAGG AAGAAAGAAA AGA (SEQ ID NO:20) (a 33-mer) is the desired oligomer. The circular template then has the sequence (SEQ ID NO:21):

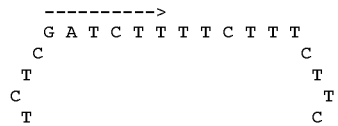

```
        ---------->
      G A T C T T T T C T T T
    C                         C
    T                         T
    C                         T
    T                         C
      T T C T T T C T T C C T
```

(the arrow denotes 5' to 3' directionality)

The rolling-circle reaction can be carried out as described above in Examples 1 and 6 (on larger scale), using the primer sequence 5'-dAAAGACG. This results in isolation of 50 mg of multimer after pelleting. Treatment of this product with hydrazine under Maxam-Gilbert conditions, followed by piperidine treatment, gives a reaction solution containing the desired monomer oligomers. Ethanol precipitation gives the isolated oligomer as desired. If necessary, this product can be further purified by reverse-phase, ion exchange, or gel filtration chromatography.

Example 9

Light-induced Cleavage of Linear Multimers

In this method, light is used to induce multimer chain cleavage at a specially modified base, which occurs once at the end of every oligomer sequence in the multimer. This modified base contains a photolabile group, such as ortho-nitrobenzyl. When flashed with light, this group falls off and induces reaction to make the nucleoside anomeric bond itself labile to hydrolysis. Further piperidine treatment induces chain cleavage with loss of this base, as with Maxam-Gilbert methods.

This base may be a modified analog of one of the four natural bases, and in this case is coded for in the circular template by its natural complement. An example of a modified nucleotide base which can be made base-labile by irradiation with light is a pyrimidine (thymine or cytosine) which has been modified by an O-nitrobenzyloxycarbonyl-hydrazinoethyl group. UV irradiation induces loss of the O-nitrobenzyl group followed by decarboxylation, leaving the C5-hydrazinoethyl group. The hydrazine moiety reacts spontaneously with the pyrimidine base to which it is attached, making it labile to hydrolysis. Hydrolysis and multimer chain cleavage is carried out as described in Example 10.

Alternatively, this base is a nonnatural nucleotide which pairs with another nonnatural base. An example of such a nonnatural pair is the iso-C/iso-G pair described in J. Piccirilli et al., *Nature*, 343, 33 (1990), which is incorporated herein by reference. Use of such a nonnatural pair allows incorporation once per unit without placing requirements or restrictions on the use of the four natural bases in the desired sequence.

Example 10

Chemical Cleavage of Linear Multimers by Incorporation of a Nonnatural Activated Base The circular template is constructed to contain one nucleotide at the end of each coded oligonucleotide which is not contained within the desired oligomer sequence. This nucleotide codes for a nonnatural nucleotide which will be incorporated between each repeated oligomer sequence in the multimer.

This nonnatural nucleotide contains synthetic modifications which allow it to be cleaved selectively, leaving the desired DNA sequences untouched. Cleavage is carried out by addition of a chemical reagent to solution which reacts selectively with the nonnatural nucleotide base, phosphate, or ribose moiety.

In the case where the nonnatural activated nucleotide is a synthetic analog of a natural base, it will be coded for by the natural pair of that base. For example, if the nonnatural nucleotide is a synthetically modified deoxyadenosine, then it will be coded for by a thymidine in the circular template. In that case, the desired oligomer contains any combination of C, T, and G bases, but not A bases.

In the case where the nonnatural activated nucleotide does not pair with any of the natural bases, but instead pairs with a second nonnatural base, the activated nucleotide is coded for by the second nonnatural base in the template circle. For example, if the nonnatural activated base is a modified analog of deoxyisoguanosine, then it will be coded for by a deoxyisocytidine in the circular template. In that case, the desired oligomer may contain any of the four natural bases.

An example of a nonnatural activated nucleotide which is a synthetic analog of a natural base is described below. 8-allyldeoxyadenosine 5'-triphosphate (ADA) is incorporated into the linear multimer once at the end of each desired oligomer sequence. The ADA nucleotide is coded for by a thymidine in the template circle. The linear multimer is then cleaved in the following manner: an activating reagent is added to a solution of the multimer, which reacts with the three-carbon allyl moiety, producing an alkylating functional group at the end of the three-carbon chain. This functional group then spontaneously alkyates the N-7 position of the purine ADA base, leaving a positive charge on the base. It is now labile to hydrolysis, and the multimer is activated for chain cleavage. A second example of such a base is N-4-allyldeoxyadenosine, which will react in similar fashion.

Hydrolysis and multimer cleavage is carried out by the Maxam-Gilbert method: the activated multimer is dissolved in 10% aqueous piperidine and is heated to 90° C. for 30 min. The solution is frozen and lyophilized and is redissolved in water and dialyzed to remove the small products of cleavage from the desired oligomers. These product desired oligomers contain phosphates at both ends. If no phosphates are desired, they can be removed enzymatically.

An example of a nonnatural activated nucleotide which does not pair with any of the natural bases is 8-allyldeoxy-isoguanosine (ADIG). It is cleaved by the same methods described in the preceding paragraph. Further examples include all purine structures which contain an N-5 and an N-7 moiety.

An example of an activating reagent which reacts with the allyl group is N-bromosuccinimide. A second example is molecular bromine ($Br_2$). A third example is an epoxidizing reagent.

A second example of a nonnatural activated nucleotide is (N4)-mercaptoacetyl-deoxyadenosine, where the mercaptan is protected by a protecting group such as t-Butylthio. When this activated nucleotide is present in the multimer it can be made labile to hydrolysis by the following procedure: to a solution of the multimer is added sodium borohydride or dithio threitol to deprotect the mercaptan. The multimer is dialyzed to remove the small reaction products. An activating reagent is then added which reacts with the mercapto group to make it a good leaving group. The N7 of the purine then is spontaneously alkylated, making it labile to hydrolysis. Hydrolysis and multimer cleavage is then carried out as described above.

An example of an activating reagent for the mercaptan is acetic anhydride. This forms the acetylmercapto group, which is a good leaving group. A second example of an activating group is disodium chlorophosphate. A third example is 1-(3-dimethylaminopropyl)-3 ethylcarbodiimide HCl.

Example 11

Chemical Cleavage of Linear Multimers by Catalytic Alkylation of N7 of an Extra Purine This procedure requires no synthetically modified bases to be incorporated into the multimer. The circular template is constructed to contain one additional pyrimidine nucleotide (C is preferred) at the end of each coded oligonucleotide. After rolling circle synthesis, the multimer contains an extra purine nucleotide (G is preferred) in between each desired oligomer.

This extra purine can be made labile to hydrolysis in the following manner. An oligonucleotide modified with a thio-ether group is added to a solution of the multimer. This oligonucleotide is complementary to part of the desired oligomer sequence in the multimer. The thioether is thus brought into close proximity to the N7 group of the extra purine nucleotide. The proximity is controlled by careful choice of the sequence of the thioether-oligonucleotide and by the chemical structure of the chain carrying the thioether. After hybridization has occurred, an activating reagent is added to solution. This reagent alkylates the thioether to produce a reactive sulfenium group ($SR_3^+$). This group spontaneously alkylates the N7 group of the extra purine, and the product of the reaction is the alkylated purine in the multimer, and the thioether-oligonucleotide, which can then catalyze alkylation at another extra purine.

Hydrolysis and multimer chain cleavage is carried out as described in Example 10. Examples of activating reagents are dimethyl sulfate, S-adenosylmethionine, dimethylpyro-carbonate and trimethyl sulfur chloride. A further example of a thioether-oligonucleotide is a circular oligonucleotide modified with a thioether at the 5-position of a pyrimidine base. The preferred pyrimidine base is the same one that codes for the extra purine. The circular oligonucleotide contains the same sequence as the template circle.

Another example of this method is the case in which the thioether oligonucleotide is the same as the template circle. In this case, rolling circle synthesis is carried out and at the end of (or during) the reaction the chemical activating reagent is added to solution to make the multimer labile to hydrolysis.

Example 12

Use of a Randomized Circular Oligomer in Screening for Biological Binding, and Identification of a Circular Sequence as a Pharmaceutical Agent A pharmacological target molecule is selected for screening. This target will depend on the disease to be treated, and it is a target which, when strongly complexed at an active site, will result in a pharmacologically desirable effect. Examples of pharmacological target molecules and the expected result of binding include: binding of HIV reverse transcriptase or HIV tat protein for inhibition of the AIDS virus; binding of FK506 binding protein for activity as an immunosuppressant; binding of squalene synthase for a cholesterol lowering effect; binding of mutated p53 protein for an antitumor effect; binding of mutated ras protein for an antitumor effect; binding of the bcr-abl mutant protein for an antileukemic effect; binding of influenza coat proteins for an anti-influenza effect; binding opiate receptors for an analgesic effect; binding to a transcription repressor protein to enhance transcription of a specific gene; binding to the multidrug resistance protein to suppress resistance to anticancer drugs; binding to d-ala-d-ala to inhibit bacterial growth; binding to d-ala-d-lactate to inhibit growth of vancomycin-resistant *enterococcus*; binding of rhinovirus coat proteins for treatment of common cold; binding of resin to lower blood pressure; binding bcl-2 protein to induce apoptosis in cancer cells; binding of thrombin to inhibit clotting; and binding of NO-synthase to inhibit septic shock.

An affinity column is then prepared. The pharmacological target molecule is attached to a commercially available activated solid support using procedures suggested by the manufacturer. Usually this consists of simple mixing of the support with the molecule of choice.

A circular oligonucleotide pool is constructed, which is a series of same-size molecules that contain a randomized domain of 10–100 bases and a domain of known sequence of 8–40 bases in length. This pool is eluted down the affinity column under approximately physiological conditions of pH and ionic strength. Fractions are collected of this eluent. Nucleotide content can be measured by monitoring the eluent stream for absorbance at 260 nm, or individual fractions can be checked. The distribution of oligomers in the fractions will depend on each molecule's binding ability: early fractions will contain the majority of molecules, which have low affinity for the target molecule. Later fractions will contain fewer oligomer sequences which have better binding ability. The latest fractions which contain DNA can be collected; these will contain the best-binding subset of sequences. This last enriched pool will then be subjected to amplification using the rolling-circle procedure; alternatively, they can be linearized and a PCR procedure can be used. The amplified products are re-cyclized and subjected to further rounds of affinity selection and amplification. After 3–30 rounds the selected sequences will be enriched in only a few strong binding sequences. The successful molecules in this pool can be identified as to sequence and structure, and they can be tested for inhibition of the specific target's function in an in vitro or in vivo assay. The most inhibitory molecules may be used as pharmaceutical agents. Alternatively, the structure can be analyzed, and a synthetic molecule can be synthesized which mimics structurally the important parts of the selected oligonucleotide. This new synthetic molecule may be used as a pharmaceutical agent.

The successful subset of enriched circular molecules can be identified as to sequence in the following way: They are used as template circles in a rolling circle synthesis to produce a complementary set of multimers. A short linear primer is used (along with a DNA polymerase and the NTP's) to make a linear complement of the multimer set. A restriction enzyme is then used to cleave the set into short duplexes having sticky ends.

At the same time, a convenient plasmid vector is chosen which contains this same restriction site, and the short duplexes can be cloned using standard procedures. For example, the plasmid is also cleaved by this restriction enzyme to make a linear duplex with sticky ends. The set of short duplexes is mixed with this linear plasmid, and ligated with T4 DNA ligase. This will produce a set of new circular plasmids with the enriched circle sequences inserted. These can be transfected into *E. Coli* according to standard procedures, plated and allowed to form colonies. Each colony can be identified by sequencing using standard procedures.

An alternative method for identifying sequence of the enriched circular oligomers is to linearize them with a restriction enzyme and sequence them directly using the Sanger dideoxy method. This will identify positions having strongly conserved bases and preferences in variable bases, and will show base positions that have no strong preference.

Example 13

Design and Construction of Partially Sequence-randomized Circular Oligomers for Selection and Screening The total length of the circular oligomers will be 30–200 nucleotides. They will contain three domains: left domain of known sequence (5–30 nucleotides); a sequence-randomized domain of 5–190 nucleotides; and a right domain of known sequence (5–30 nucleotides). When in circular form, the left and right domains will be adjacent to one another, with the right domain being 5' to the left domain In enzyme-linearized form, the left domain is at the 5'-end, followed by the random domain, and then the right domain. The initial synthesis is done using an automated synthesizer to construct a linear version of the oligomer with a phosphate on one end. Cyclization is carried out using the procedure described in Example 5. Alternatively, cyclization is carried out enzymatically, using T4 DNA ligase and a short adaptor oligomer which is complementary to the ends being joined, or using T4 RNA ligase without an adaptor.

To create the random domain using the synthesizer, two approaches can be taken. At the randomized positions, a fifth reagent bottle can be used which contains a mixture of the four phosphoramidites of the natural bases. A second approach is to use a synthesizer which can simultaneously draw reagents from more than one bottle at a time.

A randomized coupling step during DNA synthesis can be carried out with a completely sequence-random 1:1:1:1 mixture of the four phosphoramidites, or it can be any ratio of a mixture of two or more bases.

The design of the left and right domains requires the following features: the joining of the right and left domains creates a restriction enzyme site, and conversely, the cleavage of the circular oligomer with this enzyme creates a linear oligomer with the left domain on the 5' end and the right domain on the 3' end. The choice of restriction enzyme prefers the following features: the ability to cleave single-stranded DNa, and a recognition sequence of 5 bases or longer. One example is the enzyme BstN I, which recognizes the sequence 5'-CCAGG, cleaving it after the two C's, and with single strand cleaving activity. If a circular oligomer contains this sequence, the enzyme will cleave it, leaving the sequence 5'-AGG on the 5'-end, and the sequence 5'-GG on the 3'-end.

In linearized form, the right (3') domain must be able to serve as a primer binding site (for dideoxy sequencing), and so should be 8–15 bases in length to allow sufficient binding. The right and left domains should each be at least four bases in length to allow an adaptor oligomer to bind for the cyclization reaction. One skilled in the art can choose added bases which are required for these purposes in addition to the restriction sequence.

For rolling circle synthesis using a partially randomized circle, the sequence of the primer oligomer will be complementary to at least eight contiguous bases of the combined right and left domains.

Example 14

Effect of Circle Size on Rolling Circle DNA Synthesis

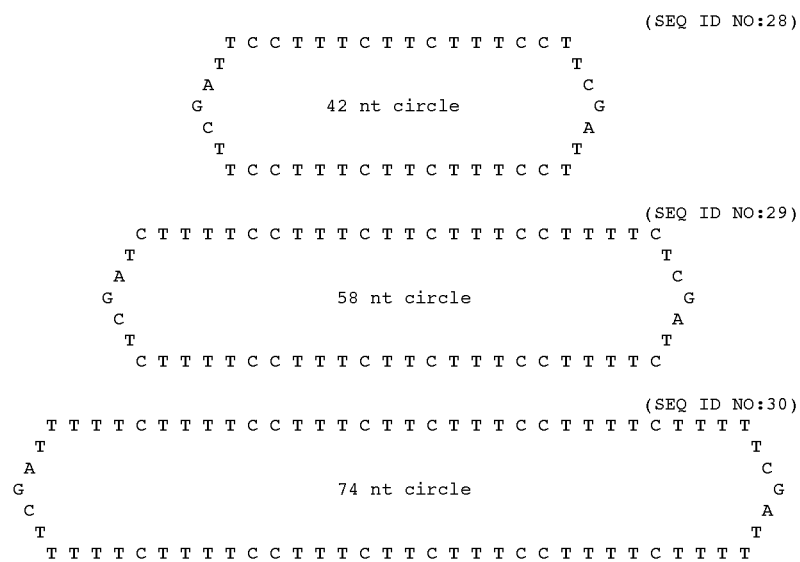

Successful rolling circle reactions using a 34 nucleotide circular template were described in Example 6. In order to investigate the effects of increasing size on the reaction, three larger circles 42-, 58-, and 74 nucleotides in length were tested. The primer sequence used was 5'-AGGAAA-GAAGAAAGGA (SEQ ID NO:31). Conditions for the reaction were as follows: 1.0 µM circle, 1–5 µM cold primer, 1.0 mM dNTP's, 2.5 units Klenow enzyme (USB), in a buffer containing 50 mM Tris.HCl (pH 7.5), 10 mM MgCl$_2$, 1 mM DTT, and 50,82 g/mL BSA. The total reaction volume was 20 µL. The reaction was incubated for 3 hours at 37° C. and then quenched by addition of denaturing formamide loading buffer (80% formamide, 10 mM EDTA). The results were analyzed by polyacrylamide denaturing gel electrophoresis.

All three circles successfully extended the primer. Further, repetitive banding patterns appeared in the lanes corresponding to the RNA synthesized using each of the three circles. These banding patterns strongly indicate that the circles were indeed used as the RNA transcription template. The banding patterns did vary by circle size as predicted. Moreover, the lengths of the transcripts in all cases were about the same, in the general range of 1000–4000 nucleotides.

Thus, the rolling reaction was not sensitive to circle size over the range of about 28 to 74 nucleotides in size. It is remarkable that a circle as small as 28 nucleotides, which is considerably smaller than the polymerase itself, behaved as a good template.

Example 15

Comparison of Rolling Circle Reactions on Small Synthetic Circles and on Single-stranded Phage φX174

Standard rolling circle conditions as given in Example 6 were used to elongate primers complementary to the above three circles (42–74 bases in length) and to a single-stranded, 5386 nucleotide-long phage. The primer for the synthetic circles was 5'-AGGAAAGAAGAAAGGA (SEQ ID NO:31), and that for the phage was 5'TGTTAACTTCT-GCGTCAT (SEQ ID NO:32). Both primers were radiolabeled, and the reactions were run as before, using a 1 µM concentration of circle. The results were analyzed by 1% agarose gel electrophoresis, and a 1-kB marker ladder was used to evaluate sizes. Results of the experiment showed that the primers were successfully elongated in all four cases, and the products have fairly wide size distributions.

The reactions using the three synthetic circles as templates gave products with banding indicating a multimeric sequence. The lengths ranged generally from 500 to 2000 nucleotides, indicating the presence of multimers that are ~25–50 monomer units in length. The experiment using φX174 gave different results. The lengths of the products fell in the ~2000–8000 nucleotide range. Therefore, the products contained only ~0.5 to 1.5 monomers, since the template circle was ~5 kB in size.

The results establish that many more useful monomers can be produced from small synthetic circles than can be produced from a much larger naturally occurring circle. Further, the larger circle did not "roll" successively, that is, it did not progress substantially more than once around the circle. Possibly the duplex being synthesized inhibits the further progression of the polymerase after the first time around, as has been reported in the literature. The small circles are short enough that any duplex being formed is strained by the curvature, and tends to unwind spontaneously as synthesis progresses.

Example 16

Construction of a DNA Circle Containing a Randomized Domain

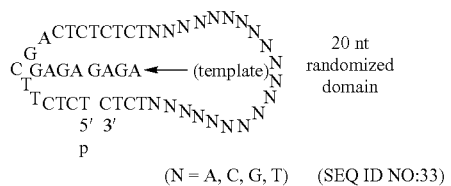

(N = A, C, G, T)  (SEQ ID NO:33)

chemical ligation

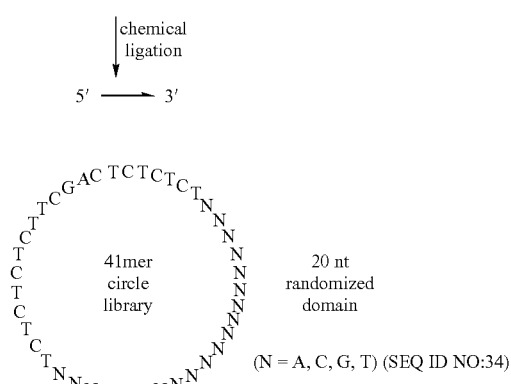

(N = A, C, G, T) (SEQ ID NO:34)

A 41-nucleotide DNA circle was constructed to have a 20-nt randomized domain as shown. The circle precursor contained a 5' phosphate and was designed to form a triple helical complex with a short purine-rich template as shown. The randomized part of the precursor was made using one bottle of mixed A, T, C, G phosphoramidites on the DNA synthesizer. Precursor (50 μM) and template oligomers (55 μM) were incubated for 7.5 hours at room temperature in a buffer containing 100 mM NiCl$_2$, 200 mM imidazole.HCL (pH 7.0), and 125 mM BrCN. The circular product depicted above was produced by the reaction and was isolated by preparative denaturing PAGE.

This product with its 20-nucleotide randomized domain represents a mixture of ~10$^{12}$ different circular DNA sequences. This mixture, or library, is suitable for subsequent selection/amplification experiments.

Example 17

Confirming the Multimer Sequence in Rolling Circle DNA Synthesis

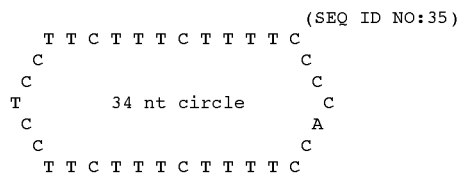

(SEQ ID NO:35)

The above circle was used as template in a standard rolling circle reaction under conditions described in Example 6 above. The primer used was 5'-AAGAAAGAAAAG (SEQ ID NO:36). After the reaction, the products were analyzed by electrophoresis on a 1% agarose gel and visualized by staining. One of the dark bands, having a length of approximately 1000 nucleotides, was excised and the DNA recovered from the gel by simple elution. This DNA was then sequenced using Sanger dideoxy methods, using a primer of sequence 5'-pTTTCTTCCTCCTTCTTTCTTTTC-CCCACCTTTTC (SEQ ID NO:37) (which corresponds to the precursor of the circle used as template). The sequencing results indicate that this approximately 1000-nucleotide length DNA was a multimer of the expected repeating monomer sequence. There was a minor background of other sequences, but it was clear that the major product was a multimer of the expected repeating monomer.

Example 18

Small Synthetic DNA Circles Act as Efficient Templates for RNA Synthesis

Small synthetic DNA circles can act as templates for RNA synthesis in addition to DNA synthesis. The following DNA circle was used as an efficient template for RNA synthesis:

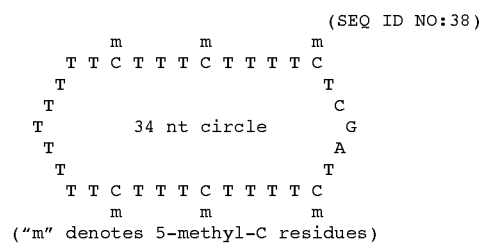

(SEQ ID NO:38)

("m" denotes 5-methyl-C residues)

Standard runoff transcription reactions using linear DNA template with a T7 RNA Polymerase promoter at the 5'-end of the sequence were carried out as described in Milligan et al., *Nucleic Acids Res.*, 15:8783 (1987). In some reactions the circular template depicted above was added, and extra long bands were found in some of the reaction tubes containing the circular template in addition to the linear template.

A control experiment was then carried out in which the linear runoff template was not included in the reaction tubes. Long RNA molecules were produced in the presence of circular template alone. This was especially surprising since the circular template did not contain any known promoter sequences.

Transcription reactions were performed using α-$^{32}$P-dUTP as a limiting nucleotide to allow efficient labeling of the RNA being synthesized. In the reactions containing circular template, an apparent repeating banding pattern was found, and most of the products found were longer than what a 15% gel could resolve. Further, the intensity of the bands resulting from the use of the circular template alone were approximately as strong as those produced by the linear promoter template alone. These results indicated that the two transcription reactions were roughly equivalent in efficiency.

Example 19

Rolling Circle RNA Synthesis does not Require a Promoter 41-mer DNA circles containing a 20-nucleotide variable sequence domain were synthesized as described in Example 1. The 20-nucleotide variable sequence domain contained runs of $T_{20}$, $C_{20}$, $A_{20}$, and $G_{20}$. Some of the circles contained an optimized T7 RNA polymerase promoter: $N_{20}$=5'-CCCTATAGTG AGTCGTATTA (SEQ ID NO:39). These 41-mer circles were used to synthesize single-stranded multimers using the following conditions: 25 mM Tris-HCl, pH 8.1; 20 mM NaCl; 15 mM $MgCl_2$; 0.4 mM spermine4HCl; 100 μg/mL Acetylated BSA; 10 mM dithiothreitol; 12.5 U/mL RNase inhibitor (Promega); 0.5 mM each rATP, rGTP, rCTP; 0.27 μCi α-$^{32}$P rUTP; 1 μM template circle (AG2C1); 50 U T7 RNA Polymerase (New England Biolabs). Results of these rolling-circle reactions showed that circles containing $T_{20}$ and $C_{20}$ domains gave long RNAs; however, those with $A_{20}$ and $G_{20}$ domains did not. It is likely that long A runs inhibit transcriptional elongation. This finding, in fact, has been reported previously in the literature. J. Tomizawa and H. Masukata, *Cell*, 51:623 (1987). The poor elongation with the $G_{20}$ run is likely due to the circle forming aggregates because of the G-rich sequence.

Finally, the data show that when a T7 promoter was present in the circle, only short RNAs were produced. This indicates that for some reason the rolling, or progression of the polymerase, was retarded by the promoter sequence. Thus, the rolling circle reaction of the present invention preferably works with circular templates that do not contain polymerase promoters. This ability to work better in the absence of polymerase promoters, along with the unusually small circle sizes, makes the process of the present invention different from natural transcription of circular templates. Further, the circular templates of the present invention encode only the RNA of interest and not extraneous sequences that are normally found when sequences are transcribed from plasmids.

Example 20

Use of Different RNA Polymerase Enzymes for Rolling Circle RNA Synthesis

Four separate enzymes were tested for their ability to carry out transcription on 34-mer circular templates. The enzymes used were T7 (New England Biolabs), T3 (Promega), and SP6 (Gibco BRL) RNA polymerases derived from phages, and *E. coli* RNA Polymerase (Boehringer Mannheim). The working concentrations of the T7, T3 and SP6 polymerases were 2 U/μl and the working concentration for *E. coli* RNA Polymerase was 0.3 U/μl. The synthesis reactions were performed under the conditions set forth in Example 19 above. No auxiliary proteins (such as DNA unwinding protein, cisA protein, or rep protein) were added to the reactions. Products were examined by both polyacrylamide and agarose gel electrophoresis, and were internally radiolabeled using limiting α-$^{32}$P-dUTP.

All four enzymes worked well at rolling transcription. The only observable difference in efficiency among the different enzymes was that the *E. coli* RNA Polymerase gave somewhat longer RNA products than the other three enzymes.

Example 21

Rolling Circle RNA Synthesis in an Extract from Eukaryotic Cells

Eukaryotic RNA polymerases were also tested for their ability to carry out transcription on circular templates. A commercially available nuclear extract from Drosophila (Promega) was added to reactions both containing and lacking a 34-mer template under the following recommended transcription conditions 7.5 mM HEPES buffer, pH 7.6; 60 mM potassium glutamate; 3.75 mM $MgCl_2$; 0.03 mM EDTA; 1.5 mM DTT; 3% glycerol; 0.5 mM each rATP, rCTP, rGTP; and 0.06–0.02 mM rUTP. The concentration of circular template was 3 μM. When no circular DNA templates were added, the extract can by itself give a small amount of new radiolabeled RNA. However, when a 34-nucleotide circle was present, a much larger amount of RNA was observed. These RNA molecules were too long to be resolved by polyacrylamide gel electrophoresis. Two experiments were performed to confirm that the RNA transcription was due to rolling transcription. First, a control reaction was performed using the linear precursor to the circle, and the result was very little RNA. This suggested that the circular structure was essential for the RNA synthesis. Second, the concentration of UTP was successively lowered, producing observable, regular banding patterns indicative of repetitive sequences. This result also suggested that the circular template was being used in rolling transcription. Thus, RNA polymerases from higher organisms can use small circles as templates. It is therefore likely that if such circles are delivered into living cells, the circles will act as templates for the production of RNA.

Example 22

Initiation Sites and Sequences of RNA Multimers

The circle shown in Example 18 was used as a template in a series of rolling circle transcription reactions in which varying amounts of rUTP were added. The conditions for the reactions were as follows: 25 mM Tris-HCl, pH 8.1; 20 mM NaCl; 15 mM $MgCl_2$; 0.4 mM spermine4HCl; 100 μg/mL Acetylated BSA; 10 mM dithiothreitol; 12.5 U/mL RNase inhibitor (Promega); 0.5 mM each rATP, rGTP, rCTP; 0.27 μCi α-$^{32}$P rUTP; 1 μM template circle (AG2C1); 50 U T7 RNA Polymerase (New England Biolabs). The concentration of rUTP was varied in the series of reactions from 0 to 60 mM. The reactions were carried out in a reaction volume of 15 μL for 1.5 hours at 37° C.

Polyacrylamide gel analysis for the products showed that as the limiting nucleotide (rUTP) decreased, regular repeating banding patterns became evident on the autoradiogram. The repeating unit corresponded to 34 nucleotides, the length of the template. Closer examination showed that the dark bands appeared largely at sites where a C residue was present in the circle. Thus, initiation of transcription is occurring primarily at C template residues, using rGTP as the first nucleotide in the transcribed RNA strand.

Subsequent experiments were performed with circles containing 28 T's and only one C nucleotide. These experiments showed that it was also possible to initiate transcription at a T (using a rATP as the first nucleotide). In general, a circle is likely to require at least a short pyrimidine-rich domain so that transcription can initiate.

The above results also provide strong evidence that the circle is successfully serving as the template for a desired RNA multimer. All other circles have shown similar banding patterns (although with different sequences and lengths) when limiting UTP is present. A longer band about 150 nucleotides in length was isolated from an analogous transcription reaction and then treated with RNase T1. Results showed bands as predicted from the expected nucleotide selectivity of this enzyme.

Example 23

Circles Encoding Repeating Stem-loop Antisense RNAs

It has previously been shown (E. D'Souza and E. Kool, *J. Biomolecular Structure and Dynamics*, 10:141 (1992)) that stem-loop DNA structures can bind tightly to single-stranded DNA targets by triplex formation. Similar binding of single-stranded RNA targets is possible by use of stem-loop RNA structures. These stem-loops bind tightly to a disease-related mRNA or viral RNA and inhibits mRNA splicing, mRNA translation, or viral replication. A 53-mer circle containing a binding domain that encodes a binding sequence that can bind to HIV1 gag gene near the start codon and a structural domain that encodes a stem-loop sequence is constructed as shown below. When transcribed by the rolling circle method it produces a repeating sequence which folds into multiple stem-loop structures. These stem-loop structures then bind tightly to a targeted RNA, inhibiting gag translation in vitro. When added to HIV1 infected cells it enters the cell by endocytosis, is transported to the nucleus, and is transcribed by the rolling circle process. The resulting stem-loop multimer inhibits viral replication by binding multiple HIV RNAs at the gag gene site.

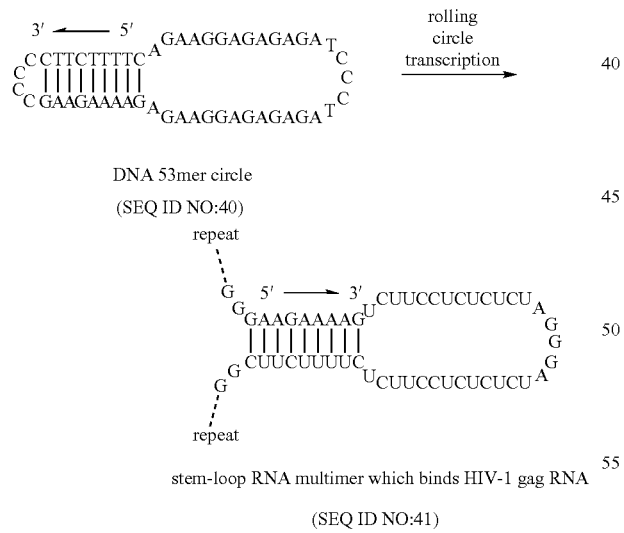

Alternatively, the 53 mer circle encodes a repeating RNA multimer, shown below, which folds into stem-loop structures which bind bcr-abl mRNA from the Philadelphia chromosome mutation leading to chronic myeloid leukemia. The stem-loops bind a sequence directly at the L6-type junction, thus causing inhibition of translation of this mRNA and inhibiting growth of the leukemic cells.

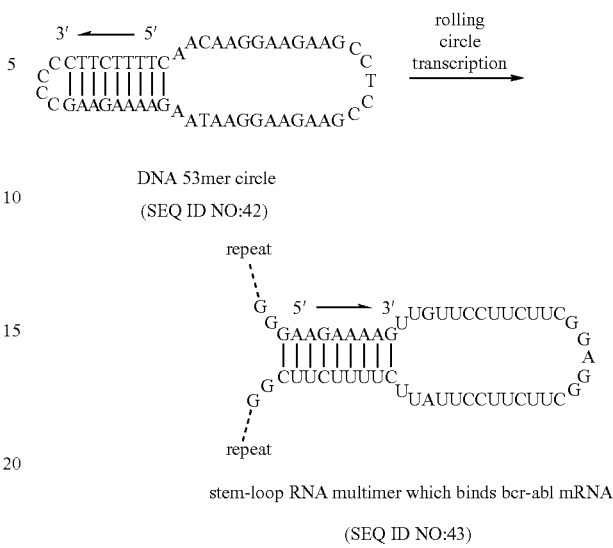

Example 24

Circles Encoding RNA Hairpin Decoy Sequences

A circle is constructed which encodes multimer RNAs that fold into repeating hairpin structures. Hairpin structures are double helical regions formed by base pairing between adjacent (inverted) complementary sequences in a single strand of RNA or DNA. These hairpins correspond to known binding sites for viral proteins that are important for viral replication. This binding to the multimer hairpins causes these proteins to be sequestered, rendering them unable to activate viral replication efficiently. Examples of known proteins in HIV-1 that could be bound by this method are the tat protein, which normally binds TAR RNA, and rev protein, which normally binds RRE RNA. U. Vaishnav and F. Wong-Staal, *Ann. Rev. Biochem.*, 60, 577 (1991).

A specific sequence is shown below. This 45 mer circle encodes repeating multimers of RNA that fold into hairpins capable of binding the HIV-1 rev protein tightly. It contains a binding site capable of binding the HIV-1 rev protein and a structural domain that encodes a hairpin sequence. Addition of these DNA circles to HIV-1-infected cells leads to inhibition of viral replication repeat

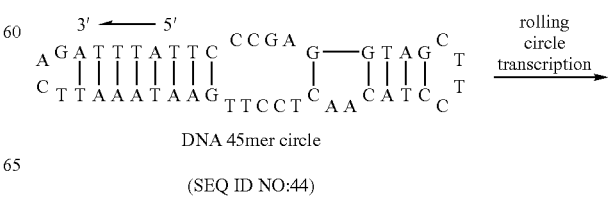

-continued

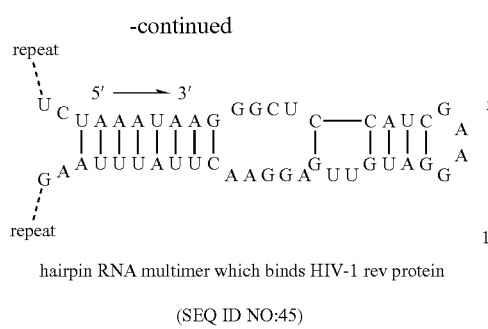

hairpin RNA multimer which binds HIV-1 rev protein (SEQ ID NO:45)

Example 25

Circles Encoding Ribozymes which Cleave RNA

Another way to inhibit translation of specific genes is to generate short RNA ribozymes which cleave specific RNA sequences in a given gene, thus leading to gene inactivation. Hammerhead-type and hairpin-type ribozymes can be constructed from short RNAs of about 14–75 nucleotides in length. Circular DNAs are constructed for encoding specific ribozyme sequences. These circles contain a binding sequence that can bind a target in RNA and a structural domain that encodes the ribozyme. A circle can encode a repeating ribozyme multimer which remains concatenated but still folds into active ribozymes. Alternatively, a circle can encode both a ribozyme and its cleavage site. In this second case the multimeric ribozyme first cleaves itself into monomer-length ribozymes; then it goes on to cleave the target mRNA or viral RNA in trans.

For example a 49 mer DNA circle is made that encodes a hammerhead-type ribozyme and its cleavage site which corresponds to the abnormal junction of the Philadelphia chromosome bcr-abl mRNA. When the DNA circle is added to CML cells it is transcribed by the cellular machinery into a multimeric RNA. This multimer first cleaves itself successively into shorter units (as short as monomer), and these shorter units cleave the mutant RNA. Thus, the circular DNA assists in inhibiting leukemic cell growth.

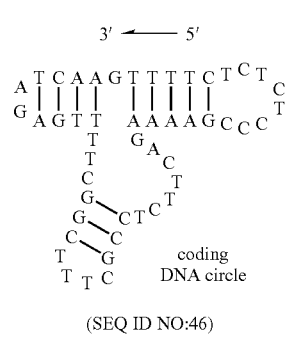

(SEQ ID NO:46)

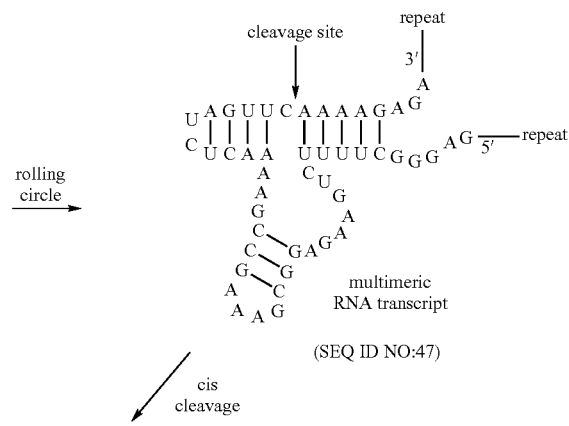

(SEQ ID NO:47)

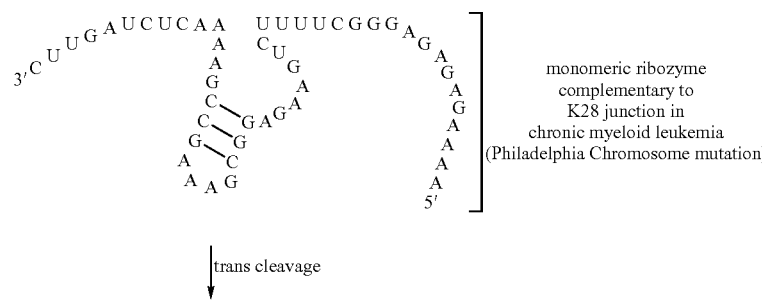

monomeric ribozyme complementary to K28 junction in chronic myeloid leukemia (Philadelphia Chromosome mutation)

(SEQ ID NO:48)

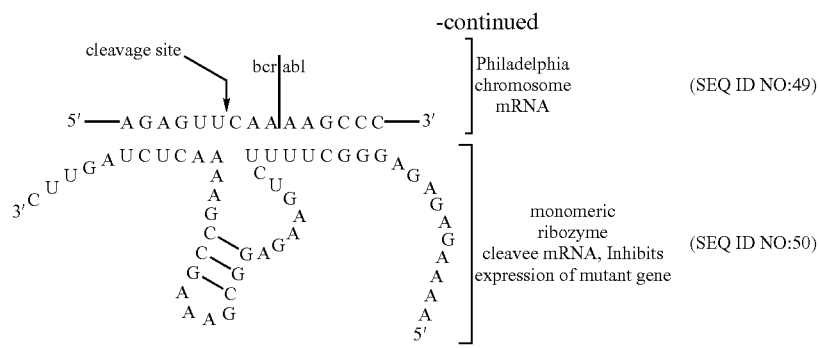

(SEQ ID NO:49) Philadelphia chromosome mRNA (SEQ ID NO:50) monomeric ribozyme cleavee mRNA, Inhibits expression of mutant gene

Example 26

Figure 4:
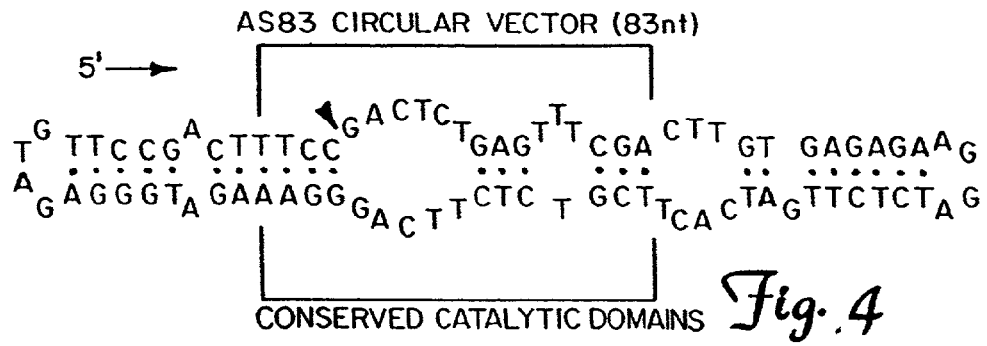
FIG. 4. Sequence of the synthetic AS83 DNA nanocircle (SEQ ID NO:51), which contains sequences mimicking catalytic segments of the Avocado Sunblotch Viroid. The arrowhead marks the encoded self-cleavage site of hammerhead-motif RNA after transcription; the horizontal arrow denotes 5' to 3' strand orientation; and the boxed portion indicates sequences encoding catalytically active RNA and substrate for cleavage.
Figure 5:
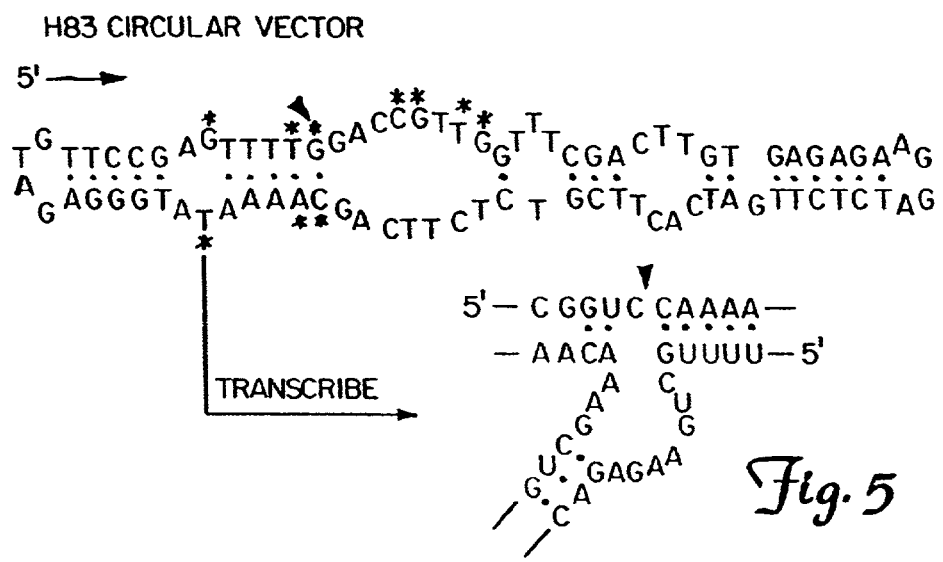
FIG. 5. Sequence of the synthetic H83 nanocircle (SEQ ID NO:52), which encodes a ribozyme targeted to nucleotides 1751–1764 of HIV-1 gag. The H83 sequence was designed by changing specific nucleotides (marked by an asterisk) in the encoded catalytic domains of AS83 nanocircle; the encoded cleavage site is denoted by an arrowhead. The sequence of the catalytic H83 transcription product (SEQ ID NOS:53 and 54) is also shown.
Figure 6:
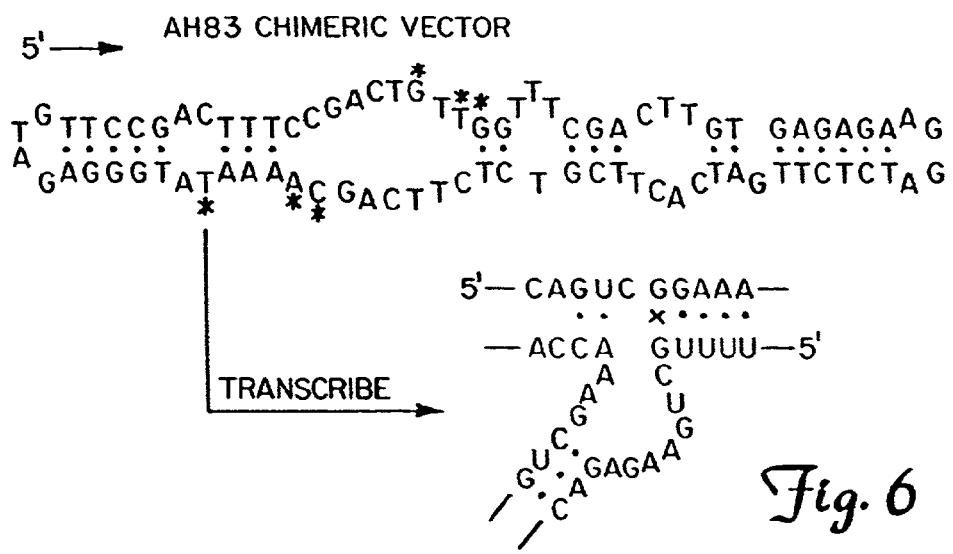
FIG. 6. Sequence of the synthetic non-autolytic AH83 chimera (SEQ ID NO:55), in which the catalytic domain is that of the H83 nanocircle but the cleavage site is that of AS83 nanocircle. The sequence of the catalytic AH83 transcription product (SEQ ID NOS:56 and 57) is also shown.

Construction of Circular DNA Templates for use in Generating Catalytic RNAs Linear oligodeoxynucleotides were synthesized on an Applied Biosystems 392 DNA synthesizer using the standard DNA cycle. Construction of an 83-nucleotide circle (AS83) (FIG. 4) was accomplished by enzymatically ligating a 41 mer (5'pGAGATGTTCC GACTTTCCGA CTCTGAGTTT CGACTTGTGA G) (SEQ ID NO:62) and a 42 mer (5'pAGAAGGATCT CTTGATCACT TCGTCTCTTC AGGGAAAGAT GG) (SEQ ID NO:63). Ligations were performed sequentially using T4 DNA ligase and two 30 nucleotide splint oligonucleotides. The first ligation for the AS83 circle used the top splint in a reaction mixture containing 50 µM each of the 41 mer and the 42 mer, 60 µM splint oligonucleotide (5'AAGTCGGAACATCTC-CCATCTTTCCCTGAA) (SEQ ID NO:64), 0.1 units/µL ligase (USB), 10 mM MgCl$_2$, 50 mM Tris.HCl (pH 7.5), 10 mM DTT, and 100 µM ATP. The reaction was incubated at 4° C. for 14 hours. The cyclization—ligation was then carried out with a second splint (5'TCAAGAGATCCT-TCTC-TCACAAGTCGAAAC) (SEQ ID NO:65) under the same conditions but with the concentration of the linear precursor lowered to 1 µM, splint to 3 µM, and enzyme to 0.33 units/µL. Products were isolated by preparative denaturing PAGE. The construction of circles H83 (FIG. 5) and AH83 (FIG. 6) was done in exactly analogous fashion, with ligations performed at the same sites (and splints of the same length but with sequence adjusted to be fully complementary). The characterization of the circles was carried out as described in E. Rubin et al., Nucleic Acids Res., 23, 3547–3553 (1995) (incorporated herein in its entirety).

The sequence of the DNA circle AS83 was designed to mimic internal segments (bases 56–98 and 147–184) of the (−) avocado sunblotch viroid (R. H. Symons, Nucleic Acids Res., 9, 6527–6537 (1981)), which contains hammerhead-motif catalytic RNAs in (+) and (−) forms (C. J. Hutchins, et al., Nucleic Acids Res., 14, 3627–3640 (1986)). The circular single-stranded DNA thus encodes a conserved hammerhead RNA sequence as well as its own substrate for cleavage; it does not, however, contain any known RNA polymerase promoter sequences. The 83 nucleotide DNA circle was constructed convergently, as described in E. Rubin et al., Nucleic acids Res., 23, 3547–3553 (1995), in 10.5% preparative yield from 41 nucleotide and 42 nucleotide oligonucleotides by enzymatic ligation using a 30 nucleotide DNA splint followed by a second intramolecular ligation at lower concentrations using a second splint.

The circular DNA templates H83 and AH83 differed from AS83 by only a few nucleotides in the noncatalytic (substrate-binding) domains in order to alter the cleavage sequence specificity of the hammerhead RNA products. Circle H83 contained 11 nucleotides different from the initial AS83 vector; the mutations were predicted to change the ribozyme target from that of a segment of ASBV viroid RNA to that of nucleotides 1753–1767 in the gag gene of HIV-1 RNA (N. Sarver et al., Science, 247, 1222–1225 (1990)). The vector also encodes a short segment of its own cleavage substrate so that self-processing is possible. Circle AH83 is a chimeric mutant containing sequences encoding the putative HIV-cleaving hammerhead but with a cleavage site for the AS83 catalytic RNA; this circular vector was predicted to produce concatemeric RNAs by rolling transcription, but without subsequent self-cleavage, thus serving as a control for the self-processing mechanism of H83.

These circular DNA vectors were much smaller than standard vectors used for generation of specific RNAs; for example, plasmid DNAs are commonly two orders of magnitude larger. Molecular modeling of the AS83 circular DNA vector confirms its small size even relative to T7 RNA polymerase; the polymerase has dimensions of 65×75×75 Å, while the DNA circle has an internal diameter of about 90 Å when in the fully open (single-stranded) form. (In the absence of a polymerase, the DNA circle is likely to have significant intramolecular secondary structure.) The E. coli holoenzyme has an even larger diameter, at about 100×100× 150 Å. The internal diameter of the circles are therefore small enough to hinder or preclude the passage of the polymerase through its center; moreover, normal turning of the enzyme around the helix axis during synthesis would require the nascent RNA strand to be pulled many times through the circle. Processive transcription on these circles must thus necessarily involve a rolling mechanism, in which the circular structure rotates about its phosphodiester bonds to avoid these potential steric problems.

Example 27

Generation of Catalytic RNAs by Rolling Transcription of Circular DNA Templates Conditions for the reactions were: 1 µM circular template (AS83, H83 or AH83), 50 units of T7 RNA polymerase (New England Biolabs), 0.5 mM ATP, GTP, CTP, 60 µM UTP, 0.27 µCi of alpha-[$^{32}$P]UTP in a pH 8.1 (25 mM Tris HCl) buffer containing 20 mM NaCl, 15 mM MgCl$_2$, 0.4 mM spermine HCl, 100 µg/mL acetylated bovine serum albumin, 10 mM DTT, and 12.5 units/mL RNase inhibitor (Promega), in a total reaction volume of 15 µL. Reaction time is 1.5 hours at 37° C., and the reaction is stopped by the addition of one volume of 30 mM EDTA, 8 M urea, and frozen at −70°. When E. coli RNA polymerase holoenzyme (Boehringer Mannheim) was used, 2 units were added to each reaction. Reactions were heated to 90° C. for 2 minutes, and then chilled on ice before being loaded on a 10% polyacrylamide denaturing gel.

Dialysis was used to quantify RNA transcripts. The polymerase reactions for quantitation by dialysis were carried out as above, but with all four rNTP's at 0.5 mM. Aliquots (10 mL) were removed at desired time points and analyzed by removal of mononucleotides by equilibrium dialysis followed by UV quantitation of the remaining polymer, using an extinction coefficient of 11703 per nucleotide at 260 nm. The data are an average from four separate experiments.

Subjecting the circular DNA template AS83 to standard in vitro transcription conditions (J. F. Milligan et al., *Nucleic Acids Res.*, 15, 8783–8798 (1987), incorporated herein in its entirety) using either T7 or E. coli RNA polymerase produced, surprisingly, large amounts of RNAs ranging in length from 83 nucleotides to several kilobases. Quantitation of the RNAs produced showed that the transcription was efficient, with about 21% of the nucleotides taken up into RNA after 1.5 hours. Examination of the RNA products showed a marked, regular banding pattern which suggested sequence-specific self-processing of the RNA under the transcription conditions. The bands were visible even at quite short (15 minute) reaction times. The smallest band in the ladder was approximately 83 nucleotides in length, and bands consistent with higher multiples of 83 nucleotides were also visible. This is consistent with self-processing of the concatemeric RNA strands during the transcription reaction to yield products as short as the monomeric repeat unit (FIG. 7). Further incubation of the transcription products in the presence of 25 mM $Mg^{2+}$ showed increasing amounts of shorter bands, with the monomer band becoming predominant within about 2–3 hours.

Circles H83 and AH83 were transcribed with efficiencies similar to that of the original AS83 circular vector. Some polymerase selectivity was observed, in that T7 RNA polymerase successfully transcribed AS83 and, to a lesser extent, the chimera AH83, but transcribed the H83 circle very poorly. The E. coli polymerase, however, transcribed the H83 vector with high relative efficiency. Rolling transcription of the H83 circle yielded a PAGE banding pattern approximately the same as for the previous AS83 circle, while the AH83 circle yielded only very long RNAs not resolved by the gel. Agarose gel analysis showed that the RNAs from the chimeric circle ranged in length from about 500 to 7,500 nucleotides, corresponding to about 6 to 90 turns around the circular template. A lack of self-processing was observed, as expected, for the chimeric AH83, confirming the requirement for a complementary cleavage site in the RNA for self-processing during the reaction. The fact that all three circles can be transcribed with good efficiency indicated that the sequence and secondary structure variations necessary for altering ribozyme cleavage specificity can be tolerated in such a vector.

RNase T1 sequencing of the monomeric products was performed by isolating the monomer bands produced from transcription of AS83 and H83 circular vectors by excision from a PAGE gel in which transcripts were not radiolabeled. After isolation the RNAs were 5'-end-labeled with g-$^{32}$P-ATP and T4 polynucleotide kinase and treated either with base (20 mM $Na_3PO_4$, pH 12) or with RNase T1 (according to the protocol supplied by USB). Nucleotide sequencing of the monomer-length RNAs confirmed them to be the expected sequences complementary to the circular templates and resulting from the predicted autolytic processing. For the AS83 vector, the monomeric sequence was 5'-pG-GAAAGUCGG AACAUCUCCC AUCUUUCCCU GAA-GAGACGA AGUGAUCAAG AGAUCCUUCU CUCA-CAAGUC GAAACUCAGA GUCp (SEQ ID NO:66); and for the H83 vector, the monomeric sequence was 5'-pCAAAACUCGG AACAUCUCCC AUAUUUUGCU GAAGAGACGA AGUGAUCAAG AGAUCCUUCU CUCACAAGUC GAAACCAACG GUCp (SEQ ID NO:67). Control reactions confirmed the absolute requirement, for the production of RNA end product, of the polymerase, the closed circular DNA, and all four nucleotides in the transcription reaction mixture.

It is not known at present where transcription is initiated in these circular vectors, and the invention is not to be viewed as requiring initiation at any particular nucleotide on the circular DNA template. Initiation can theoretically take place at any nucleotide on the template.

Example 28

Ribozyme Cleavage of Target RNAs

To explore the possibility that the monomeric 83 nucleotide catalytic RNAs might be able to act not only in cis fashion but also in trans to cleave other target RNAs, the monomer 83 nucleotide RNA produced using the H83 vector was examined for its ability to cleave a separate short 16 nucleotide RNA strand containing nucleotides 1752–1767 from HIV1 gag (sequence: 5'-pUUGUUGGUCCA-AAAUG) (SEQ ID NO:68). A similar experiment was performed to test whether the AS83 monomer RNA, could cleave in trans a short RNA sequence from (+) ASBV (sequence: 5'-pUCUGAGUCGGAAAGG) (SEQ ID NO:69) which includes nucleotides 64–73 of avocado sunblotch viroid RNA). In addition, since multimeric ribozymes have been suggested as potentially useful biologically active agents (J. Ohkawa et al., *Proc. Natl. Acad. Sci. USA*, 90, 11302–11306 (1993)) the activity of the long-repeating RNA generated from the chimeric AH83 vector, which contained about 6 to 90 joined hammerhead motifs directed to the same HIV-1 gag RNA target, was also tested.

RNA target oligonucleotides were synthesized on an Applied Biosystems instrument using the standard RNA cycle. They were 5'-end-labeled with $^{32}$P for analysis of cleavage reactions by PAGE gels and autoradiography. The complementary target for the AS83 ribozyme is 5'-pU-CUGAGUCGG AAAGG (SEQ ID NO:69) (which includes sequences 64–73 of avocado sunblotch viroid RNA), and that for the H83 and AH83 ribozymes is 5'-pUUGUUG-GUCC AAAAUG (SEQ ID NO:68) (corresponding to sequences 1752–1767 of HIV-1 gag).

Monomeric RNA was produced by autolytic processing of the concatemer RNA transcript (see Examples 26 and 27). The resulting monomeric RNAs retained their hammerhead (catalytic) domains, and the loose ends resulting from self-cleavage at the substrate sequence on the concatemeric product remained attached to the catalytic domain of the monomers. Monomeric 83 mer RNAs were excised from a 10% polyacrylamide denaturing gel of transcription products and eluted into 2.5 M $NH_4OAc$, and ethanol precipitated.

Multimeric RNA (from the AH83 circle) containing multiple copies of the hammerhead (catalytic) domain but a nonfunctional, modified self-cleavage sequence (see Examples 26 and 27) was isolated by ethanol precipitation following heat denaturation of the polymerase.

Cleavage reactions were carried out in a pH 8.3 buffer containing 50 mM Tris.HCl, 25 mM $MgCl_2$, and 10 mM NaCl, at 37° C. The reactions were stopped by the addition of one half-volume of 30 mM EDTA, 8 M urea, and frozen at −70° C. Reactions were heated to 90° C. for 2 minutes, then chilled on ice before being loaded on a 10% polyacrylamide denaturing gel.

The monomeric RNAs were found to cleave at the predicted sites in both target RNAs. The specificity of cleavage by these ribozymes was confirmed by testing the AS83 monomeric ribozyme against the HIV-RNA target and vice versa; no cleavage was seen in these cases. The multimeric RNA was also found to cleave the target sequence at the same position that the monomeric ribozyme did. Thus, both multimeric catalytic RNAs and monomeric 83 nucleotide RNAs generated by self-processing (autolytic cleavage) can serve as active ribozymes to cleave other RNAs at the expected target sequences in intermolecular fashion (trans) as well as intramolecular fashion (cis).

Example 29

Circular DNA Vector Encoding Linear and Circular Hairpin Ribosomes that Cleave HIV-1 RNA Sequences A circular DNA 73 nucleotides in length was designed to encode a hairpin-motif ribozyme and its own substrate for cleavage (FIG. 8). Hairpin ribosomes are known to also effectively catalyze the reverse reaction, i.e., they can also induce ligation of selected RNAs.

The DNA circle was synthesized and characterized as described in Example 26 starting with two approximately half-length oligonucleotides, 5'-pCGAAAACTGG ACTACAGGGA GGTACCAGGT AATGTACC (SEQ ID NO:70), and 5'-pACAACGTGTG TTTCTCTGGT CTGCTTCTCA GGAAT (SEQ ID NO:71). It was then transcribed with *E. coli* RNA polymerase. Conditions for the transcription reactions were: 1 μM circle, 3 units of *E. coli* RNA polymerase holoenzyme (Boehringer Mannheim), 0.5 mM ATP, GTP, CTP, 60 μM UTP, 0.30 μCi of alpha-[$^{32}$P]UTP in a pH 8.1 (25 mM Tris.HCl) buffer containing 20 mM NaCl, 12 mM $MgCl_2$, 0.4 mM spermine.HCl, 100 μg/mL acetylated bovine serum albumin, 10 mM dithiothreitol (DTT), and 12.5 units/mL RNase inhibitor (Promega, Madison, Wis.), in a total reaction volume of 15 μM. Reactions were incubated at 37° C., and the reaction was stopped by the addition of one volume of 30 mM EDTA, 8 M urea, and frozen at −80° C.

Transcription of this circle led to the synthesis of multimeric RNA strands containing active hairpin ribozyme sequences which were capable of being self-cleaved to yield monomer-length (73 mer) RNAs which contain active hairpin ribosomes targeted to a sequence, 5'-CUGUA↓GUCCAGGAA (SEQ ID NO:72), found in the HIV-1 pol gene (cleavage is predicted at the site marked "↓"). Results after 90 minutes showed that transcription gave robust amounts of RNA products consisting mainly of long products not resolved by the gel and a number of shorter discrete bands. Two dimensional (2-D) gel electrophoresis of these products revealed that these bands were chiefly linear monomer and circular monomer, with higher multimers (chiefly circular) also visible. Incubation of the RNAs in a buffer containing $Mg^{2+}$ showed that the final products were almost completely circular monomer and, to a lesser extent, linear monomer. Thus, the linear RNA transcription products were shown to be capable of ligating themselves into circles, a form which would be expected to substantially increase their resistance to intracellular degradation.

Cleavage experiments using isolated samples of circular monomer and linear monomer 73 mer RNAs established that both forms could cleave HIV-1 RNAs in trans at the specific HIV-1 pol sequence predicted.

Example 30

Optimized Single-stranded Promotes Allow Efficient Bacterial Transcription of Nanocircle Vectors Materials and Methods Preparation of Oligonucleotides and Circular DNA Library. DNA oligonucleotides were synthesized on solid supports using the phosphoramidite method on an Applied Biosystems model 392 DNA/RNA synthesizer. Oligodeoxyribonucleotides were deprotected by treatment with concentrated ammonia at 55° C. for 8 hours. After deblocking, DNA oligonucleotides were purified by electrophoresis on polyacrylamide denaturing gels (PAGE). After elution from the gels, the oligonucleotides were desalted on C18 Sep-Pak cartridges. Single-strand concentrations of purified DNA oligonucleotides were determined by measuring the absorbance at 260 nm at high temperature. Single-strand extinction coefficients were calculated from mononucleotide and dinucleotide data with a nearest-neighbor approximation.

An initial 103 nucleotide circular ssDNA library containing 63 nucleotide fixed sequence and 40 nucleotide randomed sequence was generated by sequential enzymatic ligations of 5'-phosphorylated 56 nucleotide and 47 nucleotide oligonucleotides using T4 DNA ligase (New England Biolabs, Inc.) and 16 nucleotide splint oligonucleotides as previously described in Daubendiek et al., *Nat. Biotechnol.*, 15(3):273–277 (1997). The constituent 5'-phosphorylated sequences were: 5'-TTC GTC TG-$N_{40}$-TCT TTC AG-3' (SEQ ID NO:73) and 5'-TTT CGT CCT CAC GGA CTC ATC AGA ATG GCA CAT TGA CTG AGG AG-3' (SEQ ID NO:74).

In Vitro Selection. Conditions for initial rolling circle transcription reaction were: 1 μM circular DNA, 2 units *E. coli* RNA polymerase (RAP) holoenzyme (Boehringer Mannheim), 0.5 mM ATP, CTP, GTP, 60 μM UTP, 0.30 μCi of α-[$^{32}$P] UTP in 25 mM Tris-HCl (pH 8.1) buffer containing 20 mM NaCl, 15 mM $MgCl_2$, 0.4 mM spermine-HCl, 100 μg/mL acetylated bovine serum albumin, 10 mM dithiothreitol (DTT), and 12.5 units/mL RNase inhibitor (Promega), in a total reaction volume of 15 μL. After a 1.5 hour incubation at 37° C., the reaction was terminated by adding an equal volume of stop solution (30 mM $Na_2EDTA$, 8 M urea, 0.02% bromophenol blue, and 0.02% xylene cyanol). Self-processed 103 nucleotide product RNAs were purified by 10% denaturing PAGE gels run at 4° C.

After elution from the gels, the selected 103 nucleotide ssRNAs were reverse transcribed (Invitrogen) with 5'-phosphorylated 18 nucleotide primer (5'-GAC TGA GGA GTT CGT CTG-3')(SEQ ID NO:75) for 1 hour at 42° C. After buffer exchange with Bio-spin column (Bio-Rad), the cDNA products were PCR-amplified Taq polymerase for 15 cycles (temperature cycle: 94° C., 1 minute; 55° C., 1 minute; 72° C., 1 minute) in the presence of 100 pmol each of two primers, 5'-GAC TGA GGA GTT CGT CTG-3' (SEQ ID NO:75) and 5'-biotin-AAT GTG TTG CCA TTC TGA-3' (SEQ ID NO:76) (Biotin Phosphoramidite, 1-Dimethoxytrityloxy-2-(N-biotinyl-4-aminobutyl)-propyl-3-O-(2-cyanoethyl)-(N,N-diisopropyl)-phosphoramidite, Glen Research, Catalog No. 10-1953-xx). The PCR products were extracted with phenol/CHCl$_3$, ethanol precipitated, and blunted with T4 DNA polymerase (LifeTechnologies, Inc.).

The blunt-ended PCR products were immobilized on magnetic beads with streptavidin (Dynal) in the presence of 80 µM binding buffer (1 M NaCl, 10 mM Tris-HCl (pH 7.5), 1 mM EDTA), rinsed with two 80 µL volumes of the binding-buffer, and eluted with 70 µL volume of 0.15 N NaOH to recover the non-biotinylated ssDNA. The recovered solution was then ion-exchanged with a spin-column (Bio-Spin P-30 Column, Bio-Rad).

After quantifying the non-biotinylated ssDNA with 5'-phosphate by measuring the absorbance at 260 nm, 1 µM non-biotinylated ssDNA with 5'-phosphate was mixed with 2 µM 24 nucleotide splint DNA (5'-AAC TCC TCA GTC AAT GTG TTG CCA-3')(SEQ ID NO:77) in the presence of 10 mM Tris-HCl (pH 7.5) and 10 mM MgCl$_2$, annealed with a thermal cycler (rate: 1° C./minute) from 90° C. to 25° C., and incubated with 0.3 units T4 DNA ligase, 0.1 mM DTT, and 10 mM ATP at 25° C. for 12 hours in a final total reaction volume of 15 µL. The circular ssDNA, unreacted ssDNA, and splint ssDNA were ethanol-precipitated and used as templates to begin the next round of in vitro selection without purification. The rolling circle transcription reaction for next round was done under the conditions described above.

Control experiments were carried out as above but eliminating the ligation step. The population without ligation contained 1 µM non-biotinylated ssDNA with 5'-phosphate and 2 µM 24 nucleotide splint DNA to mimic the conditions performed on the selections undergoing ligation.

Cloning and Sequencing. The polymerase chain reaction products of the fifteenth round pool were ligated into a TA cloning vector (Invitrogen) and cloned into *E. coli* TOP10F' (Invitrogen). Plasmid DNAs were isolated and sequenced using BigDye terminator cycle sequencing kit (PE Applied Biosystems).

Synthesis and Activity of Selected Circular ssDNAs. All selected and redesigned circular ssDNAs were made by sequential enzymatic ligations as indicated above. Sequences were: E1 , 5'-GAC TGA GGA GTT CGT CTG GCA ACG AAT CAG ACT CTT TCG GTG ACA TTG CCC AGT TTA T-3' (SEQ ID NO:78) and 5'-TCT TTC AGT TTC GTC CTC ACG GAC TCA TCA GAA TGG CAA CAC ATT-3' (SEQ ID NO:79); E38, 5'-GAC TGA GGA GTT CGT CTG GCC ACG ATC TGA ATA GTC GTT CAT CCT CAG CGG TAG CGA A-3' (SEQ ID NO:80) and 5'-TCT TTC AGT TTC GTC CTC ACG GAC TCA TCA GAA TGG CAA CAC ATT-3' (SEQ ID NO:81); E15, 5'-GAC TGA GGA GTT CGT CTG GTA AAG TAT GTT GCT ACG ACT TCT TTA TTT ACC ACG ATG C-3' (SEQ ID NO:82) and 5'-TCT TTC AGT TTC GTC CTC ACG GAC TCA TCA GAA TGG CAA CAC ATT-3' (SEQ ID NO:83); mdr63, 5'-GAC TGA GGA GTT CGT CTG TCT TTC AGT TTC GTC CT-3' (SEQ ID NO:84) and 5'-CAC GGA CTC ATC AGA ATG GCA ACA CAT T-3' (SEQ ID NO:85); marA, 5'-GAC ACT GGA GTT CGT CTG GTA AAG TAT GTT GCT ACG ACT TCT TTA TTT ACC ACG ATG C-3' (SEQ ID NO:86) and 5'-AGA AAG TGT TTC GTC CTC ACG GAC TCA TCA GAG AGC GTT CAC TCT-3' (SEQ ID NO:87); inactive marA, 5'-GAC ACT GGA GTT CGT CTG GTA AAG TAT GTT GCT ACG ACT TCT TTA TTT ACC ACG ATG C-3' (SEQ ID NO:86) and 5'-AGA AAG TGT GTC GTC CTC ACG GAC TCA TCA GAG AGC GTT CAC TC-3' (SEQ ID NO:89); marA library, 5'-AGT TCG TCT G-N$_{40}$-A GAA AGT GTT-3' (SEQ ID NO:90) and 5'-TCG TCC TCA CGG ACT CAT CAG AGA GCG TTC ACT CTG ACA CTG G-3' (SEQ ID NO:91); and short marA (63 nucleotides), 5'-GAC ACT GGA GTT CGT CTG AGA AAG TGT TTC GTC CT-3' (SEQ ID NO:92) and 5'-CAC GGA CTC ATC AGA GAG CGT TCA CTC T-3' (SEQ ID NO:93).

All rolling circle transcription reactions were done under the above-mentioned conditions using *E. coli* RAP (Boehringer Mannheim) with 0.2 µM circular ssDNA templates. Reactions were incubated at 37° C., and were stopped by the addition of one volume of stop solution. Gel analysis was on a 10% PAGE run at 4° C. The transcribed and self-processed RNAs were quantified with a radioanalytical scanner (Molecular Dynamics Storm 860).

MarA—CAT chimeric reporter construct. The chloramphenicol transferase (CAT) gene fragment was amplified from pKK232-8 (Amersham Pharmacia Biotech) by PCR with 29 nucleotide and 27 nucleotide primers. Primer sequences were: 5'-AGG TCG ACT ATG GAG AAA AAA ATC ACT GG-3' (SEQ ID NO:94) and 5'-GGT ACC CAA AAG GCC ATC CGT CAG GAT-3' (SEQ ID NO:95). After purification from an agarose gel, the PCR product was amplified by PCR with 81 nucleotide and 29 nucleotide primers. The 81 mer primer had 51 nucleotides from the marA gene and a Hind III site. The 29 nucleotide primer contained a KpnI site. Primer sequences were: 5'-CCC AAG CTT GTC ACT GGA GAA AGT GTC AGA GCG TTC GGG TTA CTC CAA ATG GCA CCT GCA AAT GGA GAA AAA AAT CAC TGG-3' (SEQ ID NO:96) and 5'-GGG GTA CCC AAA AGG CCA TCC GTC AGG AT-3' (SEQ ID NO:97). As a result, the mer segment of the marA gene was upstream of the CAT gene. After purification from the agarose gel, this marA-CAT fragment (1300 nucleotides) was ligated into pUC19 (Amersham Pharmacia Biotech) at the HindIII site and KpnI site with T4 DNA ligase. The ligated plasmids were cloned into INVαF' *E. coli* (Invitrogen) and selected by blue-white colony color.

Heat Shock Assay. INVαF' *E. coli* strain (Invitrogen) was used. After cells were transfected with the CAT vector, cells were transformed using the TOPO TA Cloning Kit (Invitrogen) according to the manufacturer's protocol. Briefly, blue-white selection was used to choose colonies with the CAT vector (white colonies). The picked white colony was cultured in LB (Luria-Bertani) medium (1.0% Tryptone, 0.5% Yeast Extract, 1.0% Sodium Chloride) containing 50 µg/mL ampicillin until the absorbance at 600 nm became 0.1. Meanwhile, the colony in LB medium was shaken at 37° C. for approximately 5–6 hours. Thereafter, 1 µL of the cell solution with 0.1 absorbance was transferred into 100 µL LB medium with the nanocircular vector and heat-shocked at 42° C. for 1 minute. Then, the solution was cultured at 37° C. for 1 hour while shaking. Again, the solution was heat-shocked at 42° C. for 1 minute and then cultured at 37° C. for 1 hour while shaking. This heat-shock/culture cycle was performed on the solution for a total of 6 hours.

Cat assay. INVαF' *E. coli* strain (Invitrogen) was used. After cells were transfected with the CAT vector, cells were cultured in LB containing 50 µg/mL ampicillin until the absorbance at 600 nm reached 0.1. Then 1 µL cell solution with 0.1 absorbance was transferred into 100 µL LB solution with the circular DNA and incubated until the absorbance at 600 nm became 0.1–0.2. Cells were heat-shocked (42° C.) once each hour. The CAT activities were measured with [$^{14}$C] chloramphenicol (100 µCi/ml) and a CAT enzyme assay system (Promega). The efficiency of the CAT protein extraction was checked by reference to β-galactosidase activity: cells were cotransfected with pSV-β-Galactosidase Control Vector (Promega) and then the chemiluminescent signal due to β-galactosidase was determined with β-galactosidase enzyme system (Promega).

RT-PCR assay for cleavage of marA mRNA. After the cells were incubated with or without the circular DNA, when the absorbance at 600 nm became 0.1–0.2, the total RNAs were isolated with SV Total RNA Isolation System (Promega). The isolated RNAs were reverse transcribed using ThermoScript RT-PCR system (Life Technologies, Inc.) with a 22 nucleotide primer (5'-GTA TAT CCA GTG ATT TTT TTC T-3') (SEQ ID NO:98) for 1 hour at 65° C. Then the cDNA products were PCR-amplified by 25 cycles (temperature cycle: 94° C., 1 minute; 55° C., 1 minute; 72° C., 1 minute) in the presence of two different primer sets. The first primer set: 5'-GTA TAT CCA GTG ATT TTT TTC T-3' (SEQ ID NO:98) and 5'-ATG ACC ATG ATT ACG CC-3' (SEQ ID NO:99). The second primer set: 5'-GTA TAT CCA GTG ATT TTT TTC T-3' (SEQ ID NO:98) and 5'-AGA GCG TTC GGG TTA CTC CA-3' (SEQ ID NO:100). The PCR products were quantified with NIH Image software.

Results and Discussion

Figure 9A:
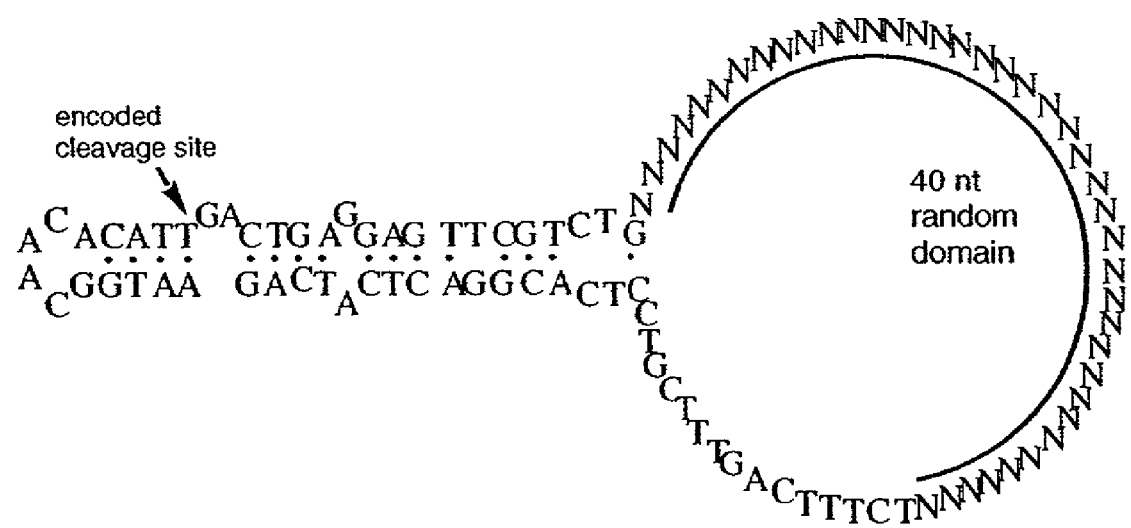
FIG. 9. (A) Diagram showing a 103 nucleotide (nt) single-stranded DNA nanocircle (SEQ ID NO:101) containing 40 nt of randomized sequence, and 63 nt fixed sequence encoding a hammerhead ribozyme. (B) Schematic illustration for in vitro selection.

In vitro selection strategy. To identify single-stranded DNA sequences that enhance or promote transcription, a single-stranded library containing a 40-nucleotide randomized domain incorporated into a 103-nucleotide single-stranded DNA nanocircle was built (FIG. 9A). The DNA library was incubated with *E. coli* RNA polymerase (RAP) holoenzyme. The resulting 103 nt ribozymes, produced by rolling circle transcription and self-processing, were eluted from polyacrylamide gels, reversed transcribed with a 5'-phosphorylated primer, and amplified by PCR with a 5'-phosphorylated primer and 5'-biotinylated primer. The PCR products were then made blunt-ended with T4 DNA polymerase. The non-biotinylated ssDNAs were recovered using strepavidin-derivatized magnetic beads and were circularized with T4 DNA ligase. The selected circular ssDNAs were then used as templates to begin the next round of in vitro selection. A small circular context has the advantage that if a given member of the library were transcribed, the result would be isothermally amplified by a rolling circle mechanism (Daubendiek et al., *J. Am. Chem. Soc.*, 117, 7818–7819 (1995)). Also encoded in the library nonrandom domain was a 63 nucleotide hammerhead ribozyme and its substrate for cleavage. Rolling circle transcription (RCT) would be expected to result in synthesis of long repeating RNAs, followed by self-cleavage in the $Mg^{2+}$-containing buffer (Daubendiek et al., *Nat. Biotechnol.*, 15(3):273–277 (1997)). The ultimate product of this process would be a monomeric 103-nucleotide ribozyme RNA of strictly defined length.

Figure 9B:
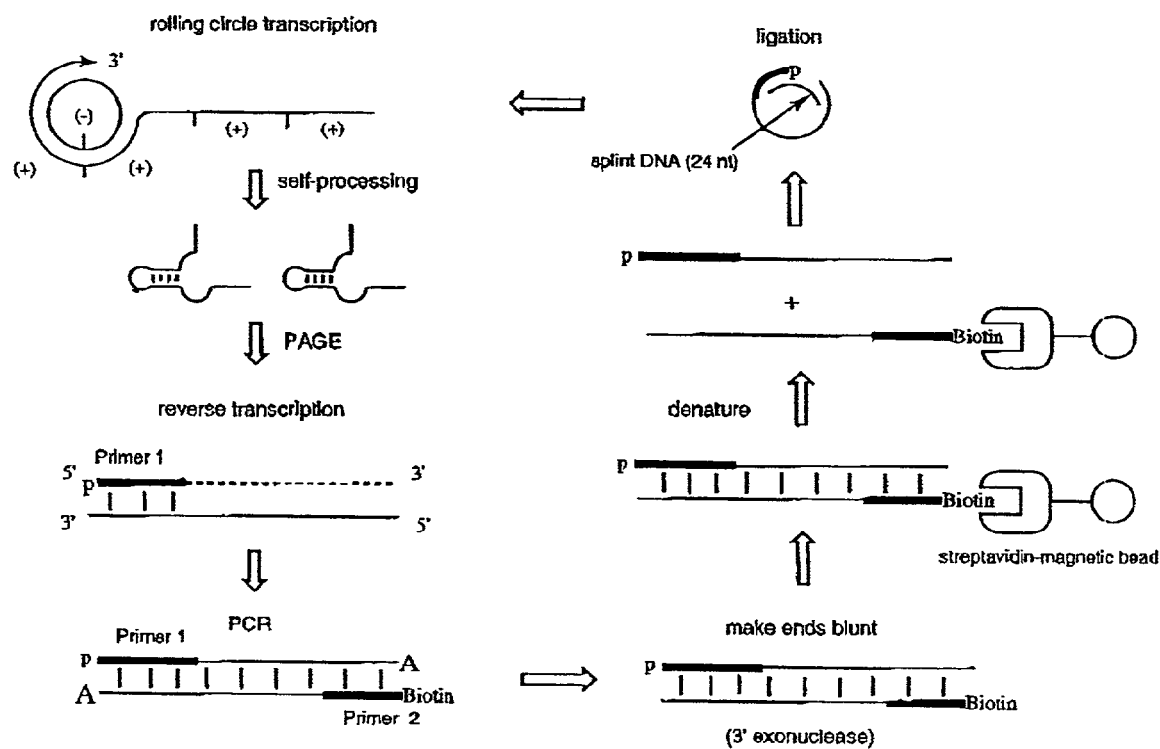

The overall scheme for selection is shown in FIG. 9B; it involves transcription of the circular library by *E. coli* RNA polymerase, separating the products (after self-processing) on a denaturing gel, excising monomer-length RNAs, amplifying them by RT-PCR, and then religating one strand from the PCR reaction to generate a new circular library enriched in sequences that are transcribed well. This scheme selects for more than mere transcription efficiency: it also tends to select for ribozymes that are efficient at self-processing, and for DNA sequences that are efficiently ligated to circular form. To encourage optimization of transcription, transcription times were kept relatively short and self-processing and ligation times relatively long.

Figure 10:
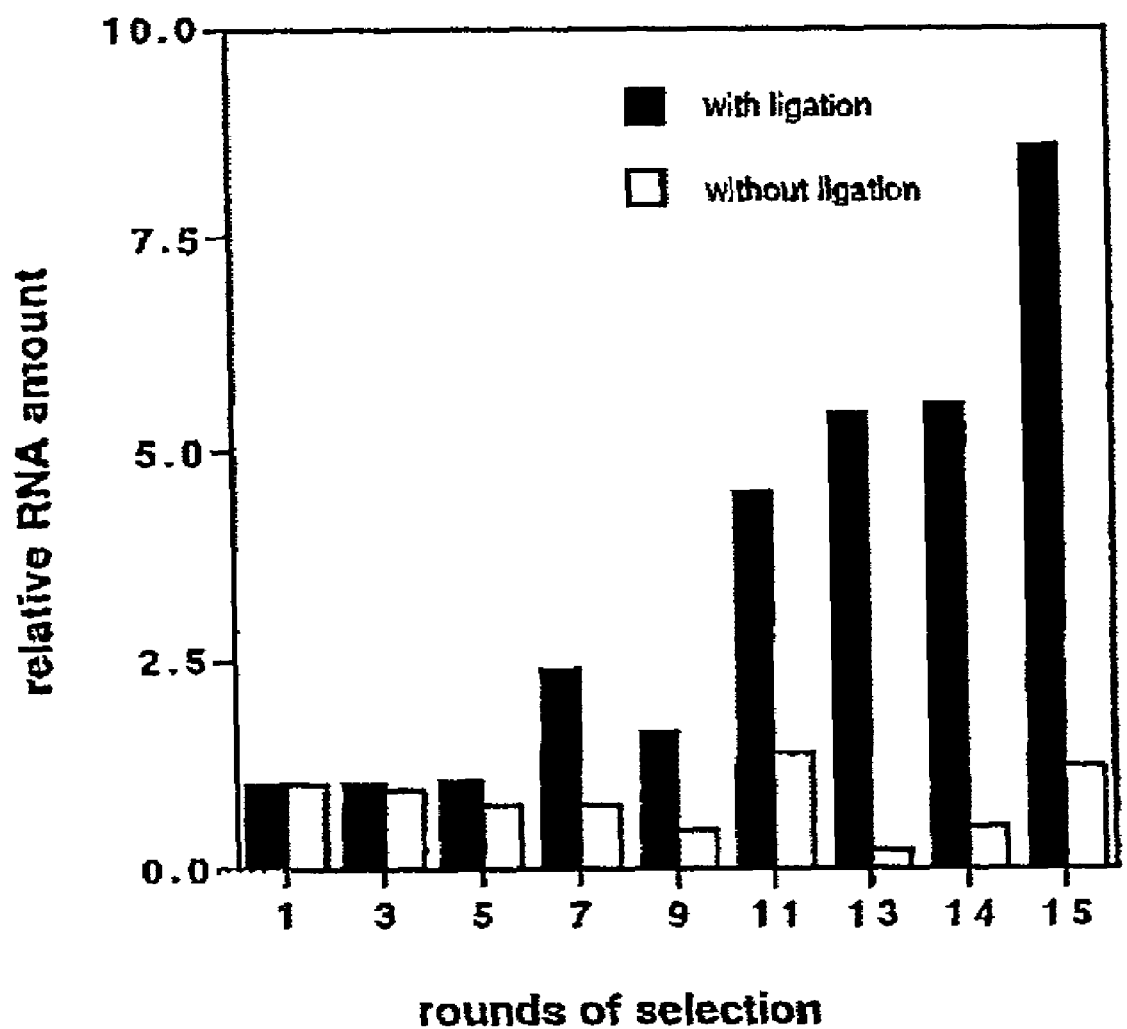
FIG. 10. Chart showing improvement of transcription activity over successive rounds of in vitro selection. Dark and light bars correspond to the relative RNA amounts (>80 nt product) for the successive population with and without ligation, respectively.

Fifteen rounds of selection and amplification were carried out by this approach. RNA amount was measured for each successive population at 37° C. after 1.5 hour. Fitness of the library (measured by total amounts of RNA>80 nucleotides produces) generally increased over the generations (FIG. 10). After fifteen rounds the fitness was increased several-fold over the original randomized set, and did not increase with further rounds (data not shown). Ligation to circular form was necessary for increasing fitness, consistent with a rolling circle mechanism of transcription. The PCR fragments were cloned after round 15 and plasmids were sequenced from 38 individual colonies. Sequences are shown in FIG. 11.

Selection yields strongly transcribed motifs in circular ssDNAs. The results from sequencing revealed three main sequence motifs that were represented more than once (FIG. 11), as well as 10 sequences represented only once. The presence of multiple examples of some of the motifs suggests that selection had indeed enriched the population with cases having superior fitness. Overall, there is a small bias toward T-rich sequences (28% T) and towards a deficiency in C (22% C). This may reflect the known preference of *E. coli* RAP for initiation with ATP opposite T, although some of the best-transcribed sequences are not T-rich (e.g., E38). Alternatively, it may reflect some nucleotide bias in the initial library and was not far from optimum without further mutations.

Figure 12:
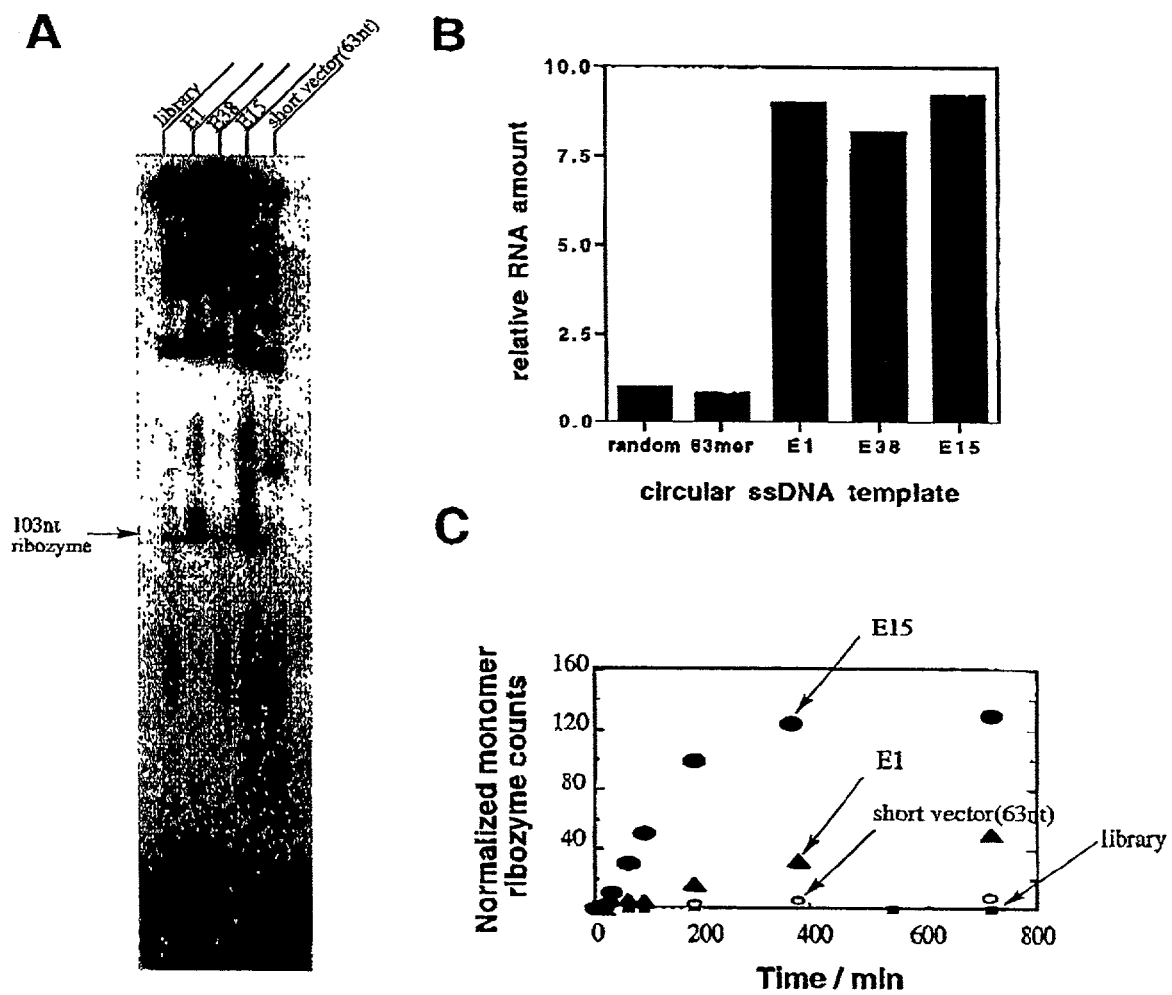
FIG. 12. Selected circular DNA motifs generate RNA synthesis in vitro with *E. coli* RNA polymerase. (A) Autoradiogram of denaturing 10% polyacrylamide gel showing in vitro transcription of the 103 nt initial library, a control 63 nt nanocircle lacking the randomized domain, and selected individual nanocircles E1, E15 and E38 (after 1.5 hours). (B) The relative RNA amounts (>80 nt product) for the 103 nt initial library, 63 nt nanocircle lacking the randomized domain, E1, E15, and E38. (C) Time course of the production of monomeric ribozyme for the 103 nt initial library (■), 63 nt nanocircle lacking the randomized domain (○), E1 (▼) and E15 (●).

The fitness of individual selected motifs was evaluated by separately examining one member of each of the three most common motifs. The individual DNA circles (labeled E1, E15 and E38, FIG. 11) were constructed in the same way as the library and were then evaluated for their ability to engender RNA synthesis in vitro with *E. coli* RNA polymerase. The results shown in FIG. 12A and B indicate that all three were considerably better transcribed than either the initial randomized nanocircle library, or than a 63 mer nanocircle lacking the randomized domain altogether. In addition to enhancement of total RNA synthesis, the rate of production of monomeric ribosomes was also enhanced for E15 and E1 (FIG. 12C), with that for E15 being the greatest. Motif E38 produced RNA that was relatively slow at self-processing (FIG. 12A) but produced the most total RNA, being 80-fold more strongly transcribed than the original circular library.

Finally, in determining whether canonical *E. coli* promoters would be active in the same context, a circle containing the 63 nucleotide ribozyme constant domain along with a 42 nucleotide *E. coli* tac promoter bottom strand was prepared (de Boer et al., *Proc. Natl. Acad. Sci. USA*, 80(1):21–25 (1983)). Transcription of this circle alone (bottom strand only) or in the presence of an equimolar amount of a 42 nucleotide top strand complement showed that neither was transcribed well in comparison to the E15 sequence (data not shown). Based on the amount of monomer ribozyme produced, the E15 circle produced 20-fold more RNA than the case with both strands of the tac promoter, and 40-fold more than the bottom strand of the promoter alone. This is consistent with a previous observation that rolling circle transcription can produce more RNA than DNAs having canonical promoters (Daubendiek et al., *J. Am. Chem. Soc.*, 117, 7818–7819 (1995)).

The predicted secondary structures for each of these three main motifs were evaluated (SantaLucia, J., Jr., *Proc. Natl. Acad. Sci. USA*, 95(4): 1460–1465 (1998)). There was no apparent structural similarity predicted for the randomized domains, save for the fact that all formed bulged stem-loop structures without exceptionally strong secondary structure.

Figure 13:
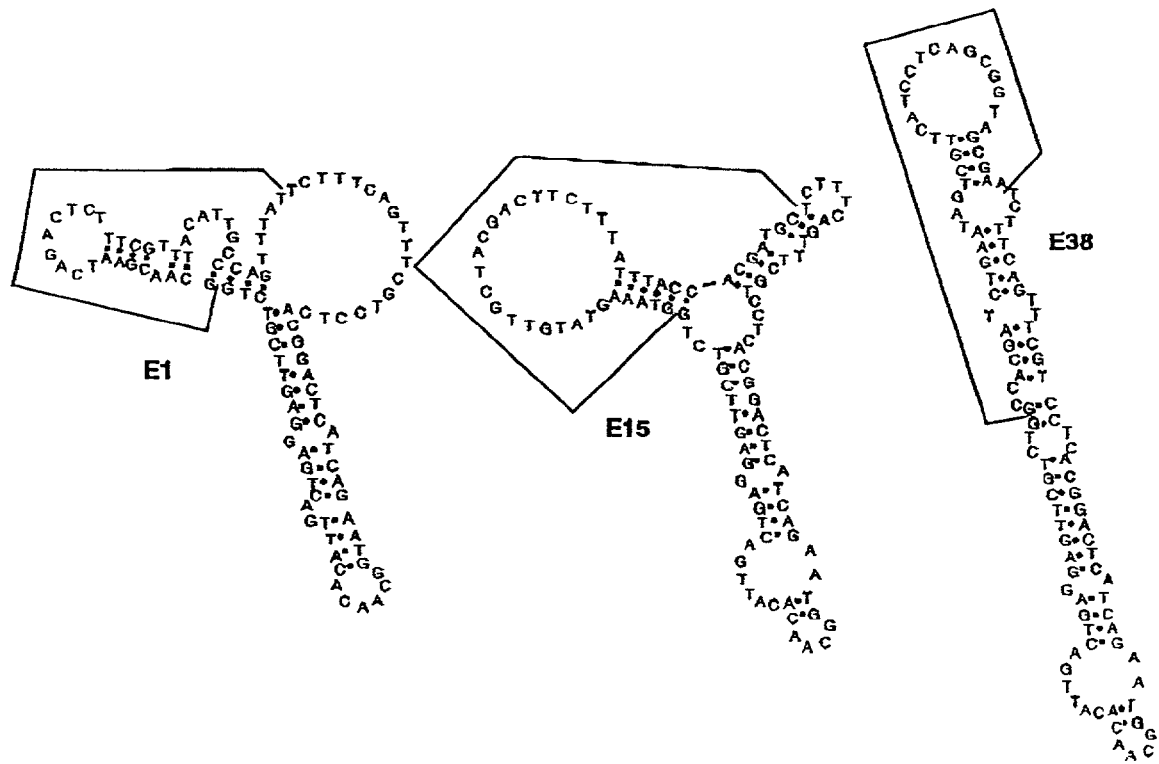
FIG. 13. Sequences and predicted secondary structures of E1 (SEQ ID NO:104), E15 (SEQ ID NO:109)and E38 (SEQ ID NO:105). Boxed part indicates selected sequence from the randomized 40 nt domain; unboxed part encodes ribozyme.

There appeared to be no correlation between predicted free energy of the folds and transcription ability. This may reflect that there is likely more than one way to increase the amount of monomer RNA produced. For example, increased initiation efficiency, increased processivity during transcription, increased self-processing ability, and increased ability of the DNA to be ligated to circular form may all contribute to fitness. Indeed, comparisons of predicted structures for E1, E15 and E38 (FIG. 13), which are all significantly different, appear to illustrate different winning strategies.

As mentioned above, one naturally occurring single-stranded promoter was previously identified that is active in *E. coli* (Masai et al., *Cell*, 89(6):897–907 (1997)). It may have been possible that some of the selected small motifs might also be active, or at least present and therefore potentially active, in *E. coli*. However, a search of the *E. coli* genome showed no significant homologies with our selected motifs.

Transplantation of promoter motif. As a further test of transplantability of a selected pseudo-promoter motif, a new nanocircle vector encoding a different hammerhead ribozyme was constructed. This new ribozyme was targeted to the marA RNA, which encodes multiple antibiotic resistance in certain pathogenic strains of *E. coli* (Cohen et al., *J. Bacteriol.*, 175(5):1484–1492 (March 1993)), and was predicted to cleave it between nucleotides 40 and 41. This new ribozyme (marA103) is different from the previous E15 by 13 nucleotides in sequence.

The transcription efficiency of this new 103 nucleotide nanocircle with *E. coli* RAP was measured (FIG. 14), comparing it to the previous E38 vector as well as to a 63 mer circle lacking the selected promoter-like domain (marA63). It retained full activity as compared to the E15 vector and indeed, exceeded that activity by a significant factor. Once again, its activity was much higher than the 63 mer lacking the promoter-like sequence. Thus, at least a conservative switch can be made in a local structural and sequence context and retain full transcriptional activity.

Figure 14:
FIG. 14. Autoradiogram of denaturing 10% polyacrylamide gel showing in vitro transcription of the 103 nt initial library, nanocircle E15, the new marA nanocircle with inactivated ribozyme, and two 63 nt nanocircle controls.

An A to C mutation in the conserved hammerhead domain of marA103 inactivated the cleavage activity of the ribozyme but did not diminish transcription, producing a long concatemeric RNA (FIG. 14).

A selected nanocircle vector is active against marA RNA in *E. coli*. Whether the marA103 nanocircle vector is transcribed in *E. coli* was evaluated. If it was transcribed, one expects that multimeric strings of ribosomes would be produced by RCT, and that these would subsequently self-process. The resulting monomeric ribosomes, or the concatemeric precursor, could then potentially cleave marA RNA in trans (Daubendiek et al., *Nat. Biotechnol.*, 15(3): 273–277 (1997); Ohmichi et al., *Nuclei Acids Res.*, 28(3): 776–783 (2000)).

Figure 15:
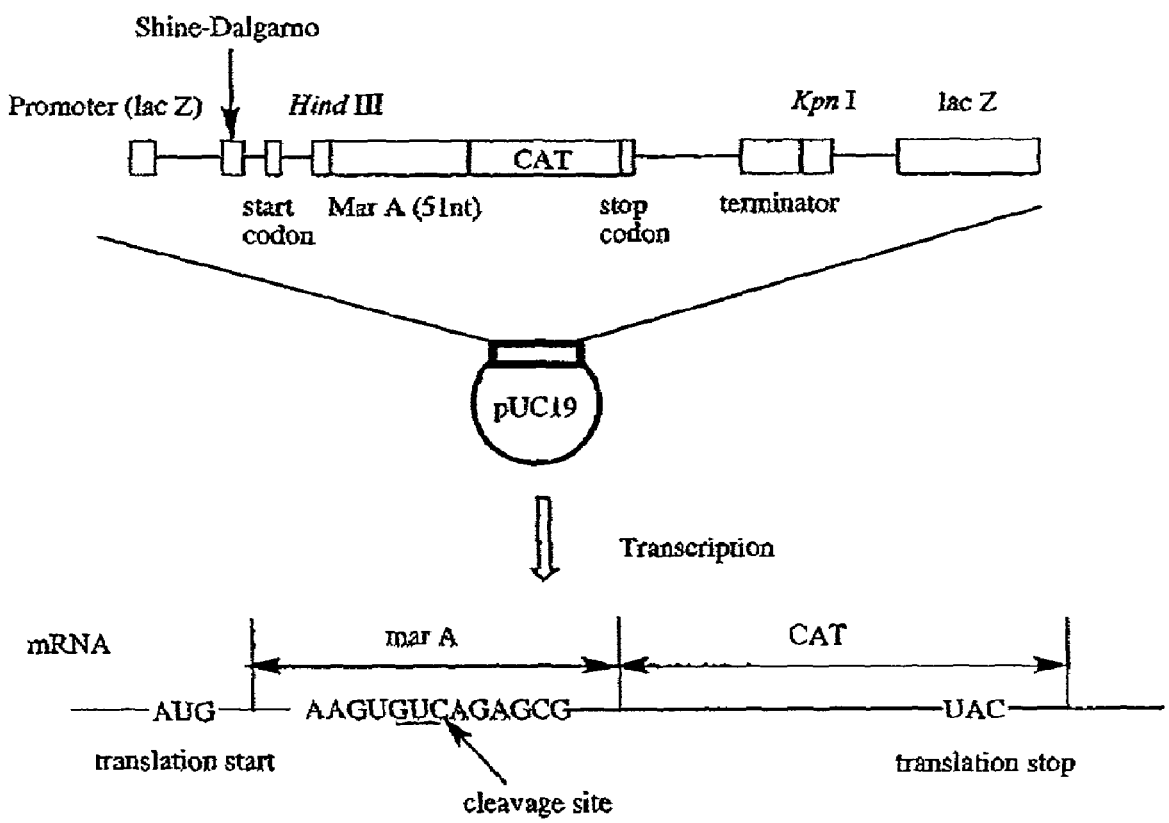
FIG. 15. Reporter plasmid construct encoding a 51 nt segment of marA RNA at the upstream end of the chloramphenicol transferase (CAT) gene, including a marA cleavage site (SEQ ID NO:124).

To evaluate this possibility, a reporter plasmid construct encoding a 51 nucleotide segment of marA RNA in the upstream end of the (CAT) gene was prepared (FIG. 15). Experiments showed that the extra 17 amino acids did not abolish CAT activity in the chimeric protein. With this construct, cleavage of the marA segment of RNA would then be expected to lead to downregulation of CAT activity by diminishing the amount of translatable CAT mRNA.

Figure 16:
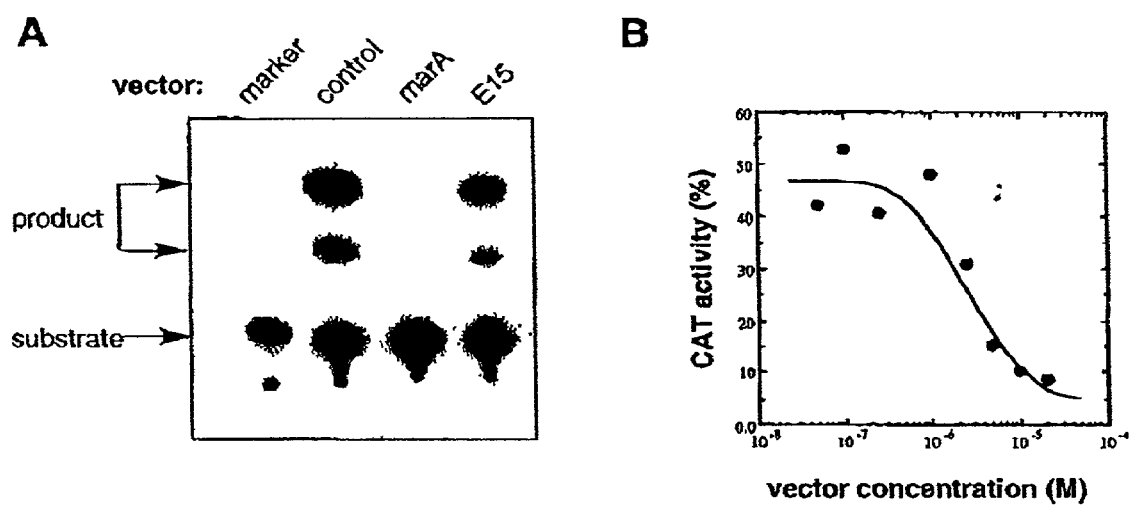
FIG. 16. (A) Thin-layer chromatogram showing levels of CAT expressed in the presence of 10 μM marA vector and E15 vector. The control lane is with no nanocircle vector. (B) Concentration dependence of downregulation of CAT activity with marA vector.

The marA103 nanocircle vector (NCV) and control DNAs were introduced into bacteria containing the reporter plasmid by heat shocking the cells. CAT activity (by radiolabeled thin layer chromatography) was measured as a function of nanocircle concentration in the medium (FIG. 16). The marA NCV was able to downregulate CAT activity markedly (FIG. 16A) as compared to the control with no vector, and to the case with the E15 vector, which should be transcribed strongly but encodes a non-marA ribozyme (FIG. 17). Varying the amount of the marA103 NCV revealed a concentration-dependent downregulation of CAT activity (FIG. 16B), reaching 50% maximal activity at about 7 uM nanocircle concentration and reaching about 80% inhibition at about 10 uM and above. Control experiments revealed that when a single A to C mutation, carried out to inactivate the ribozyme cleavage, was made, activity dropped significantly (FIG. 17), indicating that ribozyme cleavage is important. It also appears that some of the observed downregulation of CAT may be due to simple antisense activity of the ribozyme RNA, since this inactive marA NCV did show some downregulation activity. Overall, the data suggest that the main activity of the marA monomeric (or multimeric) ribosomes arises from their ability to cleave the intended target. A separate control was carried out with the 63 mer nanocircle lacking the promoter-like domain (FIG. 17); this circle was inactive over the same concentration range. This confirms that the greater amounts of RNA generated because of the promoter are needed to show trans-cleavage activity.

Finally, to independently check for cleavage of the intended target RNA (marA mRNA) in the bacterial cells, reverse transcriptase—polymerase chain reaction (RT-PCR) experiments with total isolated RNA in the presence or absence of 20 µM marA 103 nt vector were carried out, using pairs of primers on either side of the expected cleavage site, comparing the relative amounts of full-length RNA versus the expected shortened fragment (as judged by their corresponding 101 nucleotide and 60 nucleotide PCR fragments (FIG. 18)). The resulting cDNAs were then PCR-amplified in the presence of two different primer sets. The results show a 96% decrease in full-length RNA in the presence of the marA103 NCV as judged by the drop in amount of 101 nucleotide PCR fragment. Measurement of vector effects on the shorter 60 nucleotide PCR fragment show that the marA NCV causes a smaller 55% decrease, possibly due to an antisense mechanism. The results are consistent with cleavage between the two limiting primers spanning the intended site, providing further evidence in support of the expected ribozyme-mediated cleavage, decreasing CAT.

Example 31

Mammalian Cell Uptake of Nanocircle Vectors

Materials and Methods

Figure 19:
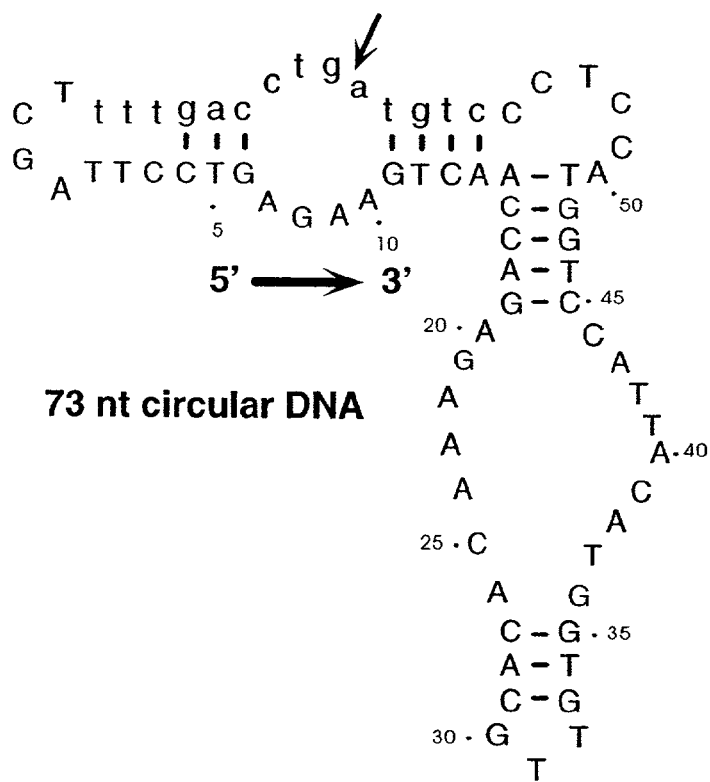
FIG. 19. Circular DNA template (SEQ ID NO:129) encoding a self-processing hairpin ribozyme.

Transfection of OST7-1 cells and extraction of total cellular RNA and DNA. Murine fibroblast cells, OST7-1, were grown in 60 mm plates to a confluency of about 60–70% (Seyhan et al., *Nucleic Acids Research*, 26(15): 3494–3504 (1998); Elroy-Stein & Moss, *Proc. Natl. Acad. Sci. USA*, 87(17):6743–6747 (September 1990)) and were transiently transfected with DNA nanocircles (SEQ ID NO:129, FIG. 19) and a plasmid vector harboring a T7 RNA polymerase promoter-driven sequence encoding a self-processing hairpin robozyme using lipofectamine-plus (Gibco-BRL) or lipofectin reagent (Gibco-BRL) in accordance with the manufacturer's instructions and as described in Seyhan et al., *Nucleic Acids Research*, 26(15):3494–3504 (1998). To monitor the time course of DNA uptake and intracellular accumulation of RNA transcripts, 2 µg of DNA was used to transfect the cells as described above except that the cell lysates were collected at 0, 12, 24, 36, 48 hours post-transfection. Total cellular RNA was extracted as described in Seyhan et al., *Nucleic Acids Research*, 26(15):3494–3504 (1998), and total cellular DNA was also extracted following manufacturer's instructions (Trizol, Gibco-BRL).

DNA and RNA dot-blot analysis. Total cellular DNA (1 µg) or RNA (5 µg), and aliquots of culture media (10 µl) obtained from the transfected cells were blotted onto a nylon membrane (Nytran Plus, 0.2 µm, S&S) using the Bio-Dot microfiltration apparatus (Bio-Rad) in accordance with the manufacturer's instructions. Membranes were prehybridized with (150 µl/cm$^2$) of 1 mM EDTA, 7% SDS, 0.5 M Na$_2$HPO$_4$ (pH 7.2) for 5 minutes at 65° C. For hybridization, prehybridization solution was replaced with the same solution. A 5'-labeled DNA probe (1×10$^6$ dpm/ml) was denatured for 5 minutes at 100° C. and added into the hybridization reaction and incubated at 43° C. for DNA blot and 44° C. for RNA blot for 24 hours. The probe used for DNA blot is complementary to the circular DNA precursor (5'-CTCCCTG-TAGTCCAGTTTTCG-3') (SEQ ID NO:128) and the probe used for RNA blot is same as the one used for primer extension. Post-hybridization washes were performed twice in (350 µl/cm$^2$) 1 mM EDTA, 40 mM Na$_2$HPO$_4$ (pH 7.2), 5% SDS and in 1 mM EDTA, 40 mM Na$_2$HPO$_4$ (pH 7.2), 1% SDS at 53° C. for DNA blot and at 43° C. for the RNA blot for 1 hour for each wash solution. Membranes were exposed for autoradiography without further drying, and quantified using a Bio-Rad model GS-525 Molecular Imager and Molecular Analyst 2.1 software.

Asymmetric PCR. Sensitive asymmetric PCR reactions were performed on total DNA isolated from the transfected cells to monitor the fate of the DNA circles. A 5'-labeled primer (1×10$^6$ dpm about 0.006 µM) complementary to the circular DNA template (see above) was included in reaction solution consisting of 50 mM KCl, 10 mM Tris.HCl (pH 8.3),1 mM MgCl$_2$, 1.25 units of Taq DNA polymerase (Perkin Elmer-Cetus), 0.4 mM ddGTP, 0.2 mM dATP, dCTP and dTTP, respectively, to generate discrete chain termination products (it yields a ddGTP-terminated 29 nt product) and about 100 ng of total cellular DNA and 1 µl of cell culture media containing transfected cells. The reaction was subjected to 22 cycles of PCR (94° C., 45 seconds; 95° C., 15 seconds; 47° C., 1 minute; 72° C., 1 minute and final extension of 72° C., 60 minutes). The products were separated on an 8% denaturing sequencing gel.

Results and Discussion

Cellular uptake of circular DNA templates. OST7-1 cells stably expressing T7 RNA polymerase were cotransfected with DNA nanocircles and, as an internal control to test for the expression of T7 RNA polymerase, a plasmid vector harboring a T7 RNA polymerase promoter-driven sequence encoding a self-processing hairpin ribozyme (Seyhan et al., *Nucleic Acids Research*, 26(15):3494–3504 (1998)). Primer extension analysis of the total cellular RNAs extracted from the co-transfected cells at time intervals yielded signals specific to the plasmid DNA, but not to the DNA circles. This indicated that OST7-1 cells were being transfected and were expressing T7 RNA polymerase. However, accumulation of transcripts from the DNA circles was too low to be detected by a standard primer extension assay.

Therefore, the uptake of circular DNA templates was monitored as a function of the amount of DNA template used (FIG. 20(A), row 2) and as a function of time (FIG. 20(A), row 3). Known quantities of the synthetic DNA circles used for transfection were blotted directly onto the nylon membrane as a control (FIG. 20(A), row 1). Specifically, total cellular DNA (1 µg samples) extracted at 48 hours after transfection from the cells transfected with series of quantities (0.5, 1, 2, 4, 6, 8 micrograms) of DNA templates were blotted as shown in FIG. 20(A), row 2. Total cellular DNAs (1 µg samples) extracted at 0, 12, 24, 36, and 48 hours from the cells after transfection with 2 µg of DNA templates were also blotted (FIG. 20(A), row 3). Aliquots of cell culture media (10 µl) obtained at 0, 12, 24, 36, and 48 hours after transfection were also blotted as shown in FIG. 20(A), row 4.

Figure 20:
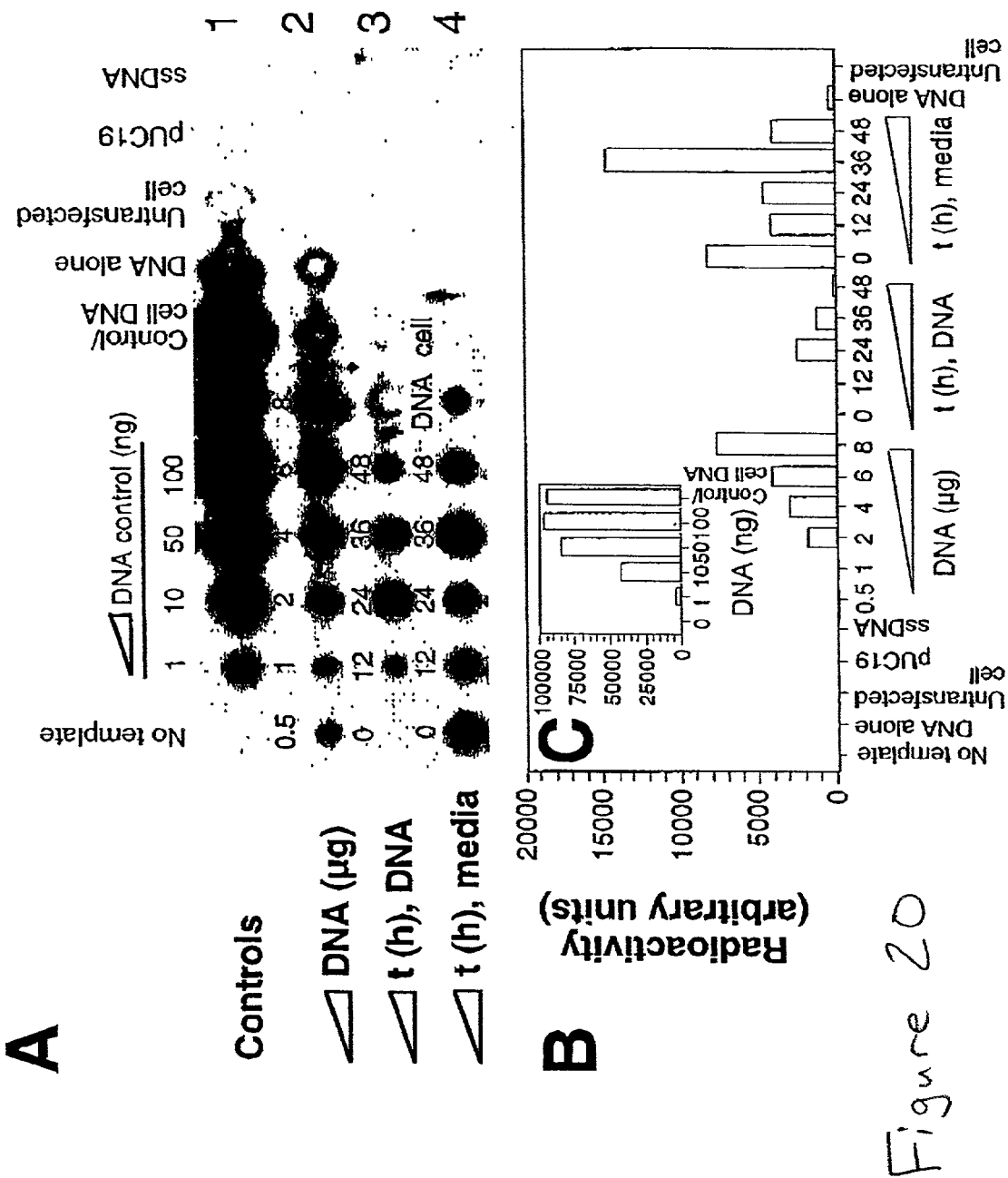
FIG. 20. (A) DNA dot-blot assay showing the internalization of DNA templates by OST7-1 cells. (B) Plot representing the quantitation of the results in A. (C) Inset plot representing the quantitation of the DNA dot-blot results, generated from known quantities of DNA circles (row 1).

DNA dot-blot and asymmetric PCR analysis on total cellular DNA and on aliquots of cell culture media obtained as a function of time after transfection showed a progressive internalization of DNA templates (FIG. 20). DNA accumulation appeared to peak at 24 hours then it declined, apparently due to cell division and intracellular degradation of the template DNA (FIG. 20(C). Analysis of cell culture media gave analogous results, except that DNA templates were detectable through the course of transfection. Circular template DNAs appeared to remain relatively stable within the culture media throughout transfection. A noticeable difference of signal intensity was observed between DNA samples complexed with transfection reagent and naked DNA indicating that DNA-lipid complex is more stable in culture media.

Figure 21:
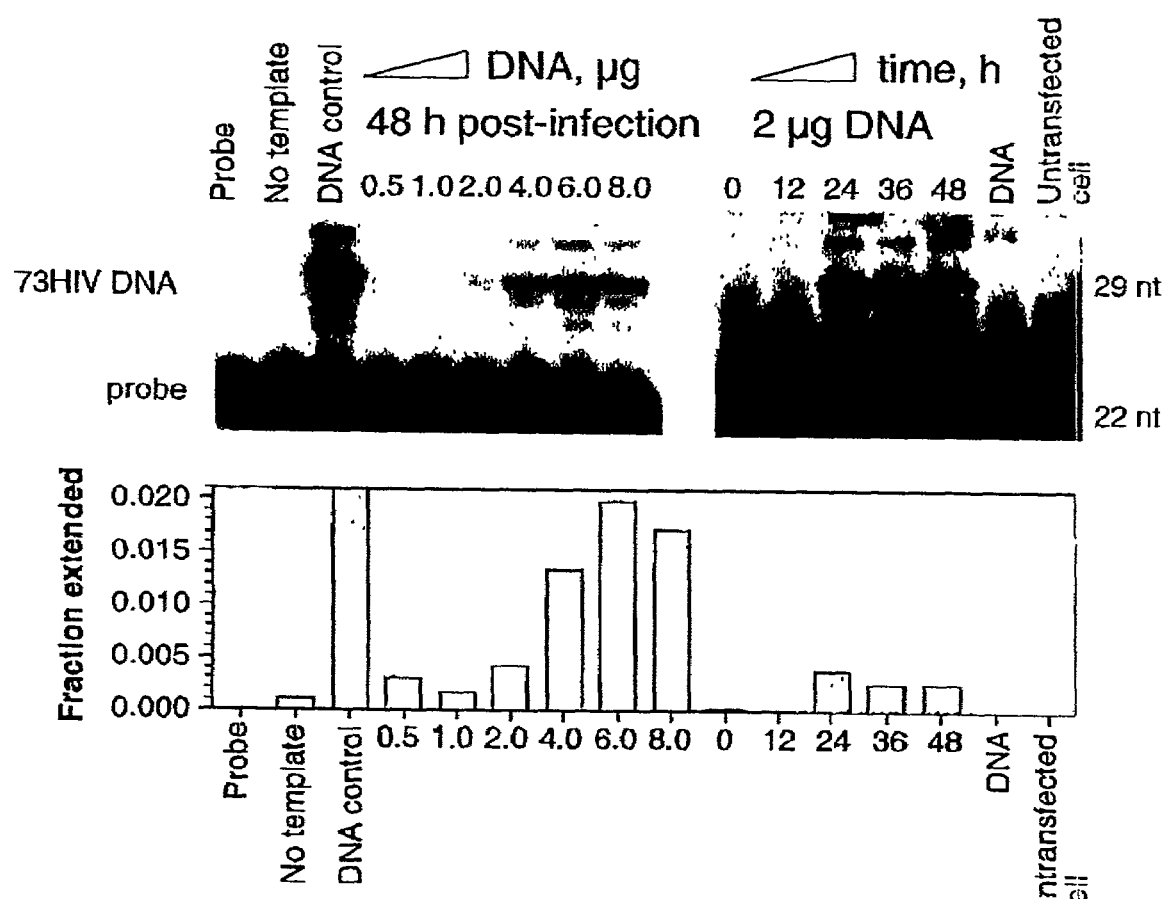
FIG. 21. Asymmetric PCR sequencing gel showing the internalization of DNA templates by OST7-1 cells. Top panel: total DNA extracts with: probe, probe alone; no template, PCR reaction was performed without the template; DNA control, 100 ng circular DNA and 1 μg of cellular DNA; DNA, DNA alone (without transfection reagent); untransfected cell, wherein the template DNA was omitted. 73 HIV DNA represents the specific asymmetric PCR termination product generated from total cellular DNA extracted from the cells transfected with DNA circles. Bottom panel: results were quantified and data was plotted as the fraction of extension products relative to sum of free primers and the extension products.

A series of titrated amounts of DNA circles was also used to assay the optimal DNA concentration for transfection (FIG. 21). Little intracellular DNA was detected when 0.5 and 1 µg DNA were used for transfection. However, significant amounts of intracellular DNA was detected when 2, 4, 6 and 8 µg of DNA used for transfection (FIGS. 20 and 21). No detectable signal was observed from the DNA extracts of control transfections where either DNA or lipofectin was omitted or when heterologous DNAs (100 ng of each pUC19 and salmon sperm DNA) were used in the DNA dot-blot assay (FIG. 20, row 1). Results from the asymmetric PCR assay were in accordance with the DNA dot-blot results and the formation of a specific PCR product confirms the specificity of the primer and the product (FIG. 21). The intracellular level of DNA circles was found to be about 87,000 copies per cell estimated by comparing intensity of the 24 hour time point signal obtained from the DNA extracts of cells transfected with 2 µg of DNA circles to known amounts of DNA of same species assayed by DNA dot-blot analysis (FIG. 20). Calculations were based on an estimated total cellular DNA content of 6 pg per cell.

Figure 22:
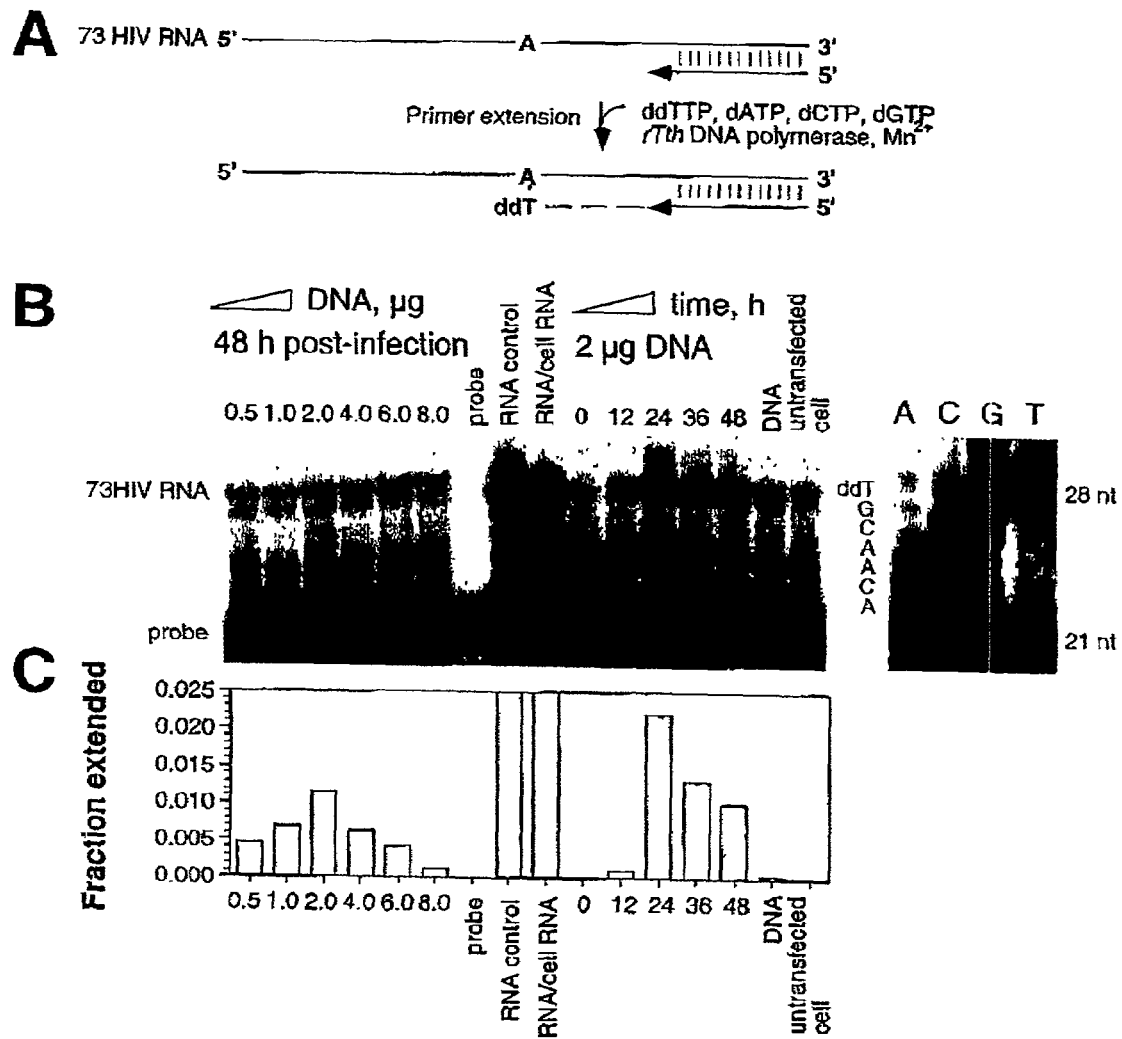
FIG. 22. (A) Schematic of the primer extension assay in detecting low quantities of RNA transcripts. (B) Sequencing gel showing the cycle-poisoned-primer extension assay. (C) The bands of the sequencing gel were quantified and plotted as the fraction of extension products relative to sum of free primers and the extension products.

Intracellular transcription from promoterless DNA nanocircles monitored by a sensitive primer extension assay. Total cellular RNAs isolated from transfected cells at time intervals after transfection with 2 µg DNA nanocircles, and at 48 hours after transfection with various quantities of DNA nanocircles, were analyzed by RNA dot-blot (data not shown) and by a sensitive primer extension assays (FIG. 22A). This assay is a modification of a reverse transcriptase primer extension assay using chain terminated nucleotides (Sigmund et al., *Methods Enzymol.*, 164, 673–690 (1988); Belfort et al., *Cell*, 41(2):375–382 (June 1985)). When the indicated dideoxynucleotides and deoxynucleotides were included, primer extension reactions were strongly terminated generating discrete termination products. This assay was further modified by coupling it to an asymmetric amplification step (cycle-poisoned-primer extension). In this assay rTth, a thermostable DNA polymerase (Perkin-Elmer/Cetus), which can catalyze the polymerization of DNA using RNA as its only template was used in the presence of MnCl$_2$ (Myers & Gelfand, *Biochemistry*, 30(31):7661–7666 (August 1991)). There was no DNA intermediate in the reaction and only one primer specific to the RNA was used.

The total cellular RNAs isolated at the indicated time points from transfection showed progressive accumulation of ribozyme transcripts within the cells (FIG. 22B). FIG. 21C shows the data for the probe, probe alone; RNA control, RNA transcript (0.5 pmol); RNA/cell RNA, about 0.5 pmol of RNA transcript was mixed with 1 μg of total cellular RNA; DNA, DNA alone without the transfection reagent; untransfected cell, wherein the template DNA was omitted in the transfection reactions. Expression appeared to peak at 24 hours after transfection, which remained relatively constant thereafter (FIGS. 22B and C). Intracellular steady-state levels of RNA transcripts were found to be less than 100 copies per cell estimated by comparing the intensity of the 24 hour time point signal obtained from the RNA extracts to known amounts of in vitro RNA transcripts of same species assayed by RNA dot-blot analysis. Calculations were based on an estimated total cellular RNA content of 10 pg per cell (Seyhan et al., *Nucleic Acids Research*, 26(15):3494–3504 (1998); Lee & Costlow, *Methods Enzymol.*, 152:633–648 (1987); and Sambrook et al, *Molecular Cloning: A Laboratory Manual*, Cold Spring Harbor Laboratory Press (1989)).

In addition, the results demonstrated that the level of ribozyme transcripts were essentially identical at 48 hours after transfection when cells were transfected with varied amounts of DNA circles (FIGS. 22B and C). Specificity of these products was confirmed by control reactions including a sequencing ladder performed on the in vitro transcribed same species of RNAs. No transcripts were detected in control cells when either DNA or lipofectin was omitted or in control cells not expressing T7 RNA polymerase (FIGS. 22B, C and data not shown). Absence of signals at the early stages of transfection indicates that signals detected on RNA extracts are specific. The results obtained from both RNA dot-blot and cycle-poisoned-primer extension assay are in complete agreement, both suggesting a progressive intracellular accumulation of ribozyme transcripts.

Results obtained from a cycled-primer extension assay carried out on the above RNA extracts, where the chain termination step was omitted, demonstrated the accumulation of long RNA transcripts consistent with intracellular synthesis of long RNA concatemers and/or generation of circular RNA transcripts that resulted in run around primer extension products. The product accumulation appeared to peak at 24 hours after transfection, but not at the early stages of transfection.

All patents, patent documents and publications cited above are incorporated by reference herein. The foregoing detailed description has been given for clarity of understanding only and no unnecessary limitations are to be understood therefrom. The invention is not limited to the exact details shown and described, for obvious modifications will occur to those skilled in the art.

What is claimed is:

1. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide wherein the circular oligonucleotide has about 15–1500 nucleotides wherein the cell is not located inside a living whole organism.

2. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide wherein the cell is a plant cell or an animal cell that is not located inside a living whole organism.

3. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide wherein the cell is a bacterial cell.

4. The method of claim 2 wherein the cell is a mammalian cell.

5. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide the method further comprising cleaving the RNA oligonucleotide multimer to yield multiple copies of the RNA oligonucleotide wherein the cell is not located inside a living whole organism.

6. The method of claim 5 wherein the cleavage is autolytic.

7. The method of claim 5 wherein the RNA oligonucleotide is linear.

8. The method of claim 5 wherein the RNA oligonucleotide is biologically active.

9. The method of claim 8 wherein the biologically active RNA oligonucleotide comprises a catalytic RNA, an antisense RNA, or a decoy RNA.

10. The method of claim 8 wherein the biologically active oligonucleotide comprises a ribozyme.

11. The method of claim 10 wherein the ribozyme is a hairpin, hammerhead-motif, or hepatitis delta catalytic ribozyme.

12. The method of claim 10 wherein the ribozyme is capable of trans cleavage.

13. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide, wherein a gene encoding an effective RNA polymerase operably linked to a promoter is co-introduced into the cell wherein the cell is not located inside a living whole organism.

14. The method of claim 13 wherein the RNA polymerase is T7 or *E. coli* polymerase.

15. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide wherein the circular oligonucleotide template is introduced into the cell using direct injection, electroporation, beat shock, calcium phosphate treatment, lipid-mediated delivery, or cation-mediated delivery wherein the cell is not located inside a living whole organism.

16. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide, wherein the method is performed in a cell explanted from a plant or animal.

17. The method of claim 16 wherein the animal is a mammal.

18. A method for synthesizing an RNA oligonucleotide inside a cell comprising introducing into a cell a single-stranded circular oligonucleotide template comprising at least one copy of a nucleotide sequence complementary to the sequence of the RNA oligonucleotide, such that the circular oligonucleotide is processed intracellularly to yield an RNA oligonucleotide multimer comprising multiple copies of the RNA oligonucleotide, wherein the method is performed in cell culture.

* * * * *

UNITED STATES PATENT AND TRADEMARK OFFICE
CERTIFICATE OF CORRECTION

| | | |
|---|---|---|
| PATENT NO. | : 7,135,312 B2 | Page 1 of 1 |
| APPLICATION NO. | : 09/997931 | |
| DATED | : November 16, 2006 | |
| INVENTOR(S) | : Eric T. Kool | |

It is certified that error appears in the above-identified patent and that said Letters Patent is hereby corrected as shown below:

Column 102, line 27, Claim 12, delete "trans" and insert --*trans*--

Column 102, line 51, Claim 15, delete "beat" and insert --heat--.

Signed and Sealed this

Fifteenth Day of May, 2007

JON W. DUDAS
*Director of the United States Patent and Trademark Office*

UNITED STATES PATENT AND TRADEMARK OFFICE
CERTIFICATE OF CORRECTION

PATENT NO.         : 7,135,312 B2
APPLICATION NO. : 09/997931
DATED                : November 14, 2006
INVENTOR(S)       : Eric T. Kool Page 1 of 1

It is certified that error appears in the above-identified patent and that said Letters Patent is hereby corrected as shown below:

Column 102, line 27, Claim 12, delete "trans" and insert --*trans*--

Column 102, line 51, Claim 15, delete "beat" and insert --heat--.

This certificate supersedes Certificate of Correction issued May 15, 2007.

Signed and Sealed this

Fifth Day of June, 2007

JON W. DUDAS
*Director of the United States Patent and Trademark Office*

SEQUENCE LISTING

```
<160> NUMBER OF SEQ ID NOS: 129

<210> SEQ ID NO 1
<211> LENGTH: 34
<212> TYPE: DNA
<213> ORGANISM: Artificial Sequence
<220> FEATURE:
<223> OTHER INFORMATION: linear precircle oligonucleotide

<400> SEQUENCE: 1
aaagaagagg gaagaaagaa aagggtgga aaag                              34

<210> SEQ ID NO 2
<211> LENGTH: 34
<212> TYPE: DNA
<213> ORGANISM: Artificial Sequence
<220> FEATURE:
<223> OTHER INFORMATION: oligonucleotide product which has an MnlI
      enzyme cleavage site at its end

<400> SEQUENCE: 2
ttttccaccc cttttctttc ttccctcttc tttc                             34

<210> SEQ ID NO 3
<211> LENGTH: 34
<212> TYPE: DNA
<213> ORGANISM: Artificial Sequence
<220> FEATURE:
<223> OTHER INFORMATION: template circle

<400> SEQUENCE: 3
gaaagaagag ggaagaaaga aaagggtgg aaaa                              34

<210> SEQ ID NO 4
<211> LENGTH: 204
<212> TYPE: DNA
```

```
<213> ORGANISM: Artificial Sequence
<220> FEATURE:
<223> OTHER INFORMATION: multimer

<400> SEQUENCE: 4
ttttccaccc cttttctttc ttccctcttc tttcttttcc acccctttttc tttcttccct    60 cttctttctt ttccacccct ttctttcttt ccctcttctt tcttttccac cccttttctt   120
tcttccctct tcttttctttt ccaccccttt tcttttcttc ctcttcttttc ttttccaccc   180 cttttctttc ttccctcttc tttc                                          204

<210> SEQ ID NO 5
<211> LENGTH: 26
<212> TYPE: DNA
<213> ORGANISM: Artificial Sequence
<220> FEATURE:
<223> OTHER INFORMATION: circular template

<400> SEQUENCE: 5
caaaaaaaaa aaacaaaaaa aaaaaa                                         26

<210> SEQ ID NO 6
<211> LENGTH: 29
<212> TYPE: DNA
<213> ORGANISM: Artificial Sequence
<220> FEATURE:
<223> OTHER INFORMATION: multimer

<400> SEQUENCE: 6 tttgttttttt tttttgttt ttttttttt                                      29

<210> SEQ ID NO 7
<211> LENGTH: 12
<212> TYPE: DNA
<213> ORGANISM: Artificial Sequence
<220> FEATURE:
<223> OTHER INFORMATION: resultant desired oligomer

<400> SEQUENCE: 7
tttttttttt tt                                                        12

<210> SEQ ID NO 8
<211> LENGTH: 12
<212> TYPE: DNA
<213> ORGANISM: Artificial Sequence
<220> FEATURE:
<223> OTHER INFORMATION: linear sequence

<400> SEQUENCE: 8
aagaaagaaa ag                                                        12

<210> SEQ ID NO 9
<211> LENGTH: 39
<212> TYPE: DNA
<213> ORGANISM: Artificial Sequence
<220> FEATURE:
<223> OTHER INFORMATION: circular template

<400> SEQUENCE: 9
cttagagacg aagatcaaac gtctctaaga cttttcttt                           39

<210> SEQ ID NO 10
<211> LENGTH: 117
<212> TYPE: DNA
<213> ORGANISM: Artificial Sequence
```

```
<220> FEATURE:
<223> OTHER INFORMATION: multimer product

<400> SEQUENCE: 10
tcttagagac gtttgatctt cgtctctaag aaagaaaagt cttagagacg tttgatcttc    60
gtctctaaga aagaaaagtc ttagagacgt ttgatcttcg tctctaagaa agaaaag      117

<210> SEQ ID NO 11
<211> LENGTH: 12
<212> TYPE: DNA
<213> ORGANISM: Artificial Sequence
<220> FEATURE:
<223> OTHER INFORMATION: desired oligomer

<400> SEQUENCE: 11
aagaaagaaa ag                                                        12

<210> SEQ ID NO 12
<211> LENGTH: 27
<212> TYPE: DNA
<213> ORGANISM: Artificial Sequence
<220> FEATURE:
<223> OTHER INFORMATION: product oligomer

<400> SEQUENCE: 12
tcttagagac gtttgatctt cgtctct                                        27

<210> SEQ ID NO 13
<211> LENGTH: 34
<212> TYPE: DNA
<213> ORGANISM: Artificial Sequence
<220> FEATURE:
<223> OTHER INFORMATION: precircle

<400> SEQUENCE: 13
gatcagaaaa gaaagaagga ggaagaaaga aaag                                34

<210> SEQ ID NO 14
<211> LENGTH: 34
<212> TYPE: DNA
<213> ORGANISM: Artificial Sequence
<220> FEATURE:
<223> OTHER INFORMATION: circular template

<400> SEQUENCE: 14
gaaaagaaag aaggaggaag aaagaaaagg atca                                34

<210> SEQ ID NO 15
<211> LENGTH: 44
<212> TYPE: DNA
<213> ORGANISM: Artificial Sequence
<220> FEATURE:
<223> OTHER INFORMATION: multimer product

<400> SEQUENCE: 15
gatccttttc tttcttcctc cttctttctt ttctgatcct tttc                     44

<210> SEQ ID NO 16
<211> LENGTH: 34
<212> TYPE: DNA
<213> ORGANISM: Artificial Sequence
<220> FEATURE:
<223> OTHER INFORMATION: desired circular oligomer

<400> SEQUENCE: 16
```

```
ttctttcttt tctgatcctt ttctttcttc ctcc                                     34

<210> SEQ ID NO 17
<211> LENGTH: 39
<212> TYPE: DNA
<213> ORGANISM: Artificial Sequence
<220> FEATURE:
<223> OTHER INFORMATION: multimer product

<400> SEQUENCE: 17
gatcagaaaa gaaagaagga ggaagaaaga aaaggatca                                39

<210> SEQ ID NO 18
<211> LENGTH: 34
<212> TYPE: DNA
<213> ORGANISM: Artificial Sequence
<220> FEATURE:
<223> OTHER INFORMATION: oligomer

<400> SEQUENCE: 18
aaaagaaaga aggaggaaga aagaaaagga tcag                                     34

<210> SEQ ID NO 19
<211> LENGTH: 34
<212> TYPE: DNA
<213> ORGANISM: Artificial Sequence
<220> FEATURE:
<223> OTHER INFORMATION: oligomer

<400> SEQUENCE: 19 gatcctttc tttcttcctc cttctttctt ttct                                      34

<210> SEQ ID NO 20
<211> LENGTH: 33
<212> TYPE: DNA
<213> ORGANISM: Artificial Sequence
<220> FEATURE:
<223> OTHER INFORMATION: product oligomer

<400> SEQUENCE: 20
cgagaaaaga agaaggagg aagaaagaaa aga                                       33

<210> SEQ ID NO 21
<211> LENGTH: 34
<212> TYPE: DNA
<213> ORGANISM: Artificial Sequence
<220> FEATURE:
<223> OTHER INFORMATION: circular template

<400> SEQUENCE: 21
gatcttttct tcttcctcc ttctttcttt tctc                                      34

<210> SEQ ID NO 22
<211> LENGTH: 39
<212> TYPE: DNA
<213> ORGANISM: Artificial Sequence
<220> FEATURE:
<223> OTHER INFORMATION: precircle

<400> SEQUENCE: 22
agacgaagat caaacgtctc taagactttt ctttcttag                                39

<210> SEQ ID NO 23
<211> LENGTH: 31
<212> TYPE: DNA
<213> ORGANISM: Artificial Sequence
```

```
<220> FEATURE:
<223> OTHER INFORMATION: circular oligomer
<221> NAME/KEY: misc_feature
<222> LOCATION: (4)..(23)
<223> OTHER INFORMATION: a, g, c, or t

<400> SEQUENCE: 23
aggnnnnnnn nnnnnnnnnn nnnaaaaaac c                              31

<210> SEQ ID NO 24
<211> LENGTH: 31
<212> TYPE: DNA
<213> ORGANISM: Artificial Sequence
<220> FEATURE:
<223> OTHER INFORMATION: circular oligomer
<221> NAME/KEY: misc_feature
<222> LOCATION: (12)..(31)
<223> OTHER INFORMATION: a, g, c, or t

<400> SEQUENCE: 24
aaaaaaccag gnnnnnnnnn nnnnnnnnnn n                              31

<210> SEQ ID NO 25
<211> LENGTH: 31
<212> TYPE: DNA
<213> ORGANISM: Artificial Sequence
<220> FEATURE:
<223> OTHER INFORMATION: circular oligomer
<221> NAME/KEY: misc_feature
<222> LOCATION: (10)..(29)
<223> OTHER INFORMATION: a, g, c, or t

<400> SEQUENCE: 25
tggttttttn nnnnnnnnn nnnnnnnnnc c                               31

<210> SEQ ID NO 26
<211> LENGTH: 31
<212> TYPE: DNA
<213> ORGANISM: Artificial Sequence
<220> FEATURE:
<223> OTHER INFORMATION: circular oligomer
<221> NAME/KEY: misc_feature
<222> LOCATION: (7)..(26)
<223> OTHER INFORMATION: a, g, c, or t

<400> SEQUENCE: 26
tttttnnnnn nnnnnnnnn nnnnnncctg g                               31

<210> SEQ ID NO 27
<211> LENGTH: 11
<212> TYPE: DNA
<213> ORGANISM: Artificial Sequence
<220> FEATURE:
<223> OTHER INFORMATION: ligation adaptor

<400> SEQUENCE: 27
ttttctttct t                                                    11

<210> SEQ ID NO 28
<211> LENGTH: 42
<212> TYPE: DNA
<213> ORGANISM: Artificial Sequence
<220> FEATURE:
<223> OTHER INFORMATION: circular template

<400> SEQUENCE: 28
ctttcttctt tccttcgatt cctttcttct ttccttcgat tc                  42
```

```
<210> SEQ ID NO 29
<211> LENGTH: 58
<212> TYPE: DNA
<213> ORGANISM: Artificial Sequence
<220> FEATURE:
<223> OTHER INFORMATION: circular template

<400> SEQUENCE: 29
ctttcttctt tccttttctc gatcttttcc tttcttcttt ccttttctcg atcttttc        58

<210> SEQ ID NO 30
<211> LENGTH: 74
<212> TYPE: DNA
<213> ORGANISM: Artificial Sequence
<220> FEATURE:
<223> OTHER INFORMATION: circular template

<400> SEQUENCE: 30
ctttcttctt tccttttctt tttcgatttt tcttttcctt tcttcttttcc ttttcttttt      60 cgattttttct tttc                                                       74

<210> SEQ ID NO 31
<211> LENGTH: 16
<212> TYPE: DNA
<213> ORGANISM: Artificial Sequence
<220> FEATURE:
<223> OTHER INFORMATION: primer

<400> SEQUENCE: 31
aggaaagaag aaagga                                                      16

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
tgttaacttc tgcgtcat                                                    18

<210> SEQ ID NO 33
<211> LENGTH: 41
<212> TYPE: DNA
<213> ORGANISM: Artificial Sequence
<220> FEATURE:
<223> OTHER INFORMATION: template
<221> NAME/KEY: misc_feature
<222> LOCATION: (18)..(37)
<223> OTHER INFORMATION: a, g, c, or t

<400> SEQUENCE: 33
tctcttcgac tctctctnnn nnnnnnnnnn nnnnnnntct c                          41

<210> SEQ ID NO 34
<211> LENGTH: 41
<212> TYPE: DNA
<213> ORGANISM: Artificial Sequence
<220> FEATURE:
<223> OTHER INFORMATION: circle library
<221> NAME/KEY: misc_feature
<222> LOCATION: (18)..(37)
<223> OTHER INFORMATION: a, g, c, or t

<400> SEQUENCE: 34
tctcttcgac tctctctnnn nnnnnnnnnn nnnnnnntct c                          41
```

<210> SEQ ID NO 35
<211> LENGTH: 34
<212> TYPE: DNA
<213> ORGANISM: Artificial Sequence
<220> FEATURE:
<223> OTHER INFORMATION: circular template

<400> SEQUENCE: 35
tcttttcccc accttttctt tcttcctcct tctt         34

<210> SEQ ID NO 36
<211> LENGTH: 12
<212> TYPE: DNA
<213> ORGANISM: Artificial Sequence
<220> FEATURE:
<223> OTHER INFORMATION: primer

<400> SEQUENCE: 36
aagaaagaaa ag                                 12

<210> SEQ ID NO 37
<211> LENGTH: 34
<212> TYPE: DNA
<213> ORGANISM: Artificial Sequence
<220> FEATURE:
<223> OTHER INFORMATION: primer

<400> SEQUENCE: 37
tttcttcctc cttctttctt ttccccacct tttc         34

<210> SEQ ID NO 38
<211> LENGTH: 34
<212> TYPE: DNA
<213> ORGANISM: Artificial Sequence
<220> FEATURE:
<223> OTHER INFORMATION: circle template
<221> NAME/KEY: misc_feature
<222> LOCATION: (4)..(4)
<223> OTHER INFORMATION: m5c
<221> NAME/KEY: misc_feature
<222> LOCATION: (9)..(9)
<223> OTHER INFORMATION: m5c
<221> NAME/KEY: misc_feature
<222> LOCATION: (15)..(15)
<223> OTHER INFORMATION: m5c
<221> NAME/KEY: misc_feature
<222> LOCATION: (20)..(20)
<223> OTHER INFORMATION: m5c
<221> NAME/KEY: misc_feature
<222> LOCATION: (24)..(24)
<223> OTHER INFORMATION: m5c
<221> NAME/KEY: misc_feature
<222> LOCATION: (34)..(34)
<223> OTHER INFORMATION: m5c

<400> SEQUENCE: 38
tttnttttnt cgatnttttn tttnttttt tttn          34

<210> SEQ ID NO 39
<211> LENGTH: 20
<212> TYPE: DNA
<213> ORGANISM: Artificial Sequence
<220> FEATURE:
<223> OTHER INFORMATION: optimized T7 RNA polymerase promoter site

<400> SEQUENCE: 39
ccctatagtg agtcgtatta                         20

<210> SEQ ID NO 40
<211> LENGTH: 53
<212> TYPE: DNA
<213> ORGANISM: Artificial Sequence
<220> FEATURE:
<223> OTHER INFORMATION: 53mer circle

<400> SEQUENCE: 40
tttcttcccc cgaagaaaag agaaggagag agatccctag agagaggaag act        53

<210> SEQ ID NO 41
<211> LENGTH: 53
<212> TYPE: RNA
<213> ORGANISM: Artificial Sequence
<220> FEATURE:
<223> OTHER INFORMATION: stem-loop multimer which binds HIV-1 gag RNA

<400> SEQUENCE: 41
gggaagaaaa gucuuccucu cucuagggau cucucuccuu cucuuucuu cgg         53

<210> SEQ ID NO 42
<211> LENGTH: 53
<212> TYPE: DNA
<213> ORGANISM: Artificial Sequence
<220> FEATURE:
<223> OTHER INFORMATION: 53 circle

<400> SEQUENCE: 42
tttcttcccc cgaagaaaag aataaggaag aagcctccga agaaggaaca act        53

<210> SEQ ID NO 43
<211> LENGTH: 53
<212> TYPE: RNA
<213> ORGANISM: Artificial Sequence
<220> FEATURE:
<223> OTHER INFORMATION: stem-loop multimer which binds to bcr-abl mRNA

<400> SEQUENCE: 43
gggaagaaaa guuguuccuu cuucggaggc uucuuccuua uucuuucuu cgg         53

<210> SEQ ID NO 44
<211> LENGTH: 45
<212> TYPE: DNA
<213> ORGANISM: Artificial Sequence
<220> FEATURE:
<223> OTHER INFORMATION: 45 circle

<400> SEQUENCE: 44
ttatttagac ttaaataagt tcctcaacat ccttcgatgg agccc                 45

<210> SEQ ID NO 45
<211> LENGTH: 45
<212> TYPE: RNA
<213> ORGANISM: Artificial Sequence
<220> FEATURE:
<223> OTHER INFORMATION: hairpin multimer which binds HIV-1 rev protein

<400> SEQUENCE: 45
ucuaaauaag ggcuccaucg aaggauguug aggaacuuau uuaag                 45

<210> SEQ ID NO 46
<211> LENGTH: 49
<212> TYPE: DNA
<213> ORGANISM: Artificial Sequence
<220> FEATURE:
<223> OTHER INFORMATION: circle

<400> SEQUENCE: 46
ttttgaacta gagttttcgg ctttcgcctc ttcagaaaag ccctctctc             49

<210> SEQ ID NO 47
<211> LENGTH: 49
<212> TYPE: RNA
<213> ORGANISM: Artificial Sequence
<220> FEATURE:
<223> OTHER INFORMATION: multimer RNA transcript

<400> SEQUENCE: 47
gagggcuuuu cugaagaggc gaaagccgaa aacucuaguu caaaagaga             49

<210> SEQ ID NO 48
<211> LENGTH: 49
<212> TYPE: RNA
<213> ORGANISM: Artificial Sequence
<220> FEATURE:
<223> OTHER INFORMATION: monomeric ribozyme complementary to K28
      junction in chronic myelo id leukemia (Philadelphia Chromosome
      mutation)

<400> SEQUENCE: 48
aaaagagaga gggcuuuucu gaagaggcga agccgaaaaa cucuaguuc             49

<210> SEQ ID NO 49
<211> LENGTH: 15
<212> TYPE: RNA
<213> ORGANISM: Artificial Sequence
<220> FEATURE:
<223> OTHER INFORMATION: Philadelphia chromosome mRNA

<400> SEQUENCE: 49
agaguucaaa agccc                                                 15

<210> SEQ ID NO 50
<211> LENGTH: 49
<212> TYPE: RNA
<213> ORGANISM: Artificial Sequence
<220> FEATURE:
<223> OTHER INFORMATION: monomeric ribozyme

<400> SEQUENCE: 50
aaaagagaga gggcuuuucu gaagaggcga agccgaaaaa cucuaguuc             49

<210> SEQ ID NO 51
<211> LENGTH: 83
<212> TYPE: DNA
<213> ORGANISM: Artificial Sequence
<220> FEATURE:
<223> OTHER INFORMATION: AS83 nanocircle

<400> SEQUENCE: 51
gttccgactt tccgactctg agtttcgact tgtgagagaa ggatctcttg atcacttcgt   60
ctcttcaggg aaagatggga gat                                          83

<210> SEQ ID NO 52
<211> LENGTH: 83
<212> TYPE: DNA
<213> ORGANISM: Artificial Sequence
<220> FEATURE:
<223> OTHER INFORMATION: H83 nanocircle

<400> SEQUENCE: 52

```
gttccgagtt ttggaccgtt ggtttcgact tgtgagagaa ggatctcttg atcacttcgt      60
ctcttcagca aaatatggga gat                                              83

<210> SEQ ID NO 53
<211> LENGTH: 10
<212> TYPE: RNA
<213> ORGANISM: Artificial Sequence
<220> FEATURE:
<223> OTHER INFORMATION: catalytic H83 transcription product

<400> SEQUENCE: 53
cgguccaaaa                                                             10

<210> SEQ ID NO 54
<211> LENGTH: 25
<212> TYPE: RNA
<213> ORGANISM: Artificial Sequence
<220> FEATURE:
<223> OTHER INFORMATION: catalytic H83 transcription product

<400> SEQUENCE: 54
uuuugcugaa gagacgucga aacaa                                            25

<210> SEQ ID NO 55
<211> LENGTH: 83
<212> TYPE: DNA
<213> ORGANISM: Artificial Sequence
<220> FEATURE:
<223> OTHER INFORMATION: non-autolytic AH83 chimera

<400> SEQUENCE: 55
gttccgactt tccgactgtt ggtttcgact tgtgagagaa ggatctcttg atcacttcgt      60
ctcttcagca aaatatggga gat                                              83

<210> SEQ ID NO 56
<211> LENGTH: 10
<212> TYPE: RNA
<213> ORGANISM: Artificial Sequence
<220> FEATURE:
<223> OTHER INFORMATION: catalytic AH83 transcription product

<400> SEQUENCE: 56
cagucggaaa                                                             10

<210> SEQ ID NO 57
<211> LENGTH: 25
<212> TYPE: RNA
<213> ORGANISM: Artificial Sequence
<220> FEATURE:
<223> OTHER INFORMATION: catalytic AH83 transcription product

<400> SEQUENCE: 57
uuuugcugaa gagacgucga aacca                                            25

<210> SEQ ID NO 58
<211> LENGTH: 83
<212> TYPE: RNA
<213> ORGANISM: Artificial Sequence
<220> FEATURE:
<223> OTHER INFORMATION: string of hammerhead-motif RNAs

<400> SEQUENCE: 58
cuucucucac aagucgaaac ucagagucgg aaagucggaa caucucccau cuucccuga       60 agagacgaag ugaucaagag auc                                              83
```

<210> SEQ ID NO 59
<211> LENGTH: 83
<212> TYPE: RNA
<213> ORGANISM: Artificial Sequence
<220> FEATURE:
<223> OTHER INFORMATION: monomeric hammerhead-motif RNA

<400> SEQUENCE: 59
ggaaagucgg aacaucuccc aucuuuccca gaagagacga agugaucaag agauccuucu    60
cucacaaguc gaaacucaga guc    83

<210> SEQ ID NO 60
<211> LENGTH: 73
<212> TYPE: DNA
<213> ORGANISM: Artificial Sequence
<220> FEATURE:
<223> OTHER INFORMATION: nanocircle vector

<400> SEQUENCE: 60
gaaaactgga ctacagggag gtaccaggta atgtaccaca acgtgtgttt ctctggtctg    60
cttctcagga atc    73

<210> SEQ ID NO 61
<211> LENGTH: 73
<212> TYPE: RNA
<213> ORGANISM: Artificial Sequence
<220> FEATURE:
<223> OTHER INFORMATION: circular monomer

<400> SEQUENCE: 61
gauuccugag aagcagacca gagaaacaca cguugguggua cauuaccugg uaccucccug    60
uaguccaguu uuc    73

<210> SEQ ID NO 62
<211> LENGTH: 41
<212> TYPE: DNA
<213> ORGANISM: Artificial Sequence
<220> FEATURE:
<223> OTHER INFORMATION: oligomer

<400> SEQUENCE: 62
gagatgttcc gactttccga ctctgagttt cgacttgtga g    41

<210> SEQ ID NO 63
<211> LENGTH: 42
<212> TYPE: DNA
<213> ORGANISM: Artificial Sequence
<220> FEATURE:
<223> OTHER INFORMATION: oligomer

<400> SEQUENCE: 63
agaaggatct cttgatcact tcgtctcttc agggaaagat gg    42

<210> SEQ ID NO 64
<211> LENGTH: 30
<212> TYPE: DNA
<213> ORGANISM: Artificial Sequence
<220> FEATURE:
<223> OTHER INFORMATION: splint oligonucleotide

<400> SEQUENCE: 64
aagtcggaac atctcccatc tttccctgaa    30

<210> SEQ ID NO 65
<211> LENGTH: 30
<212> TYPE: DNA
<213> ORGANISM: Artificial Sequence
<220> FEATURE:
<223> OTHER INFORMATION: splint oligonucleotide

<400> SEQUENCE: 65
tcaagagatc cttctctcac aagtcgaaac                                      30

<210> SEQ ID NO 66
<211> LENGTH: 83
<212> TYPE: RNA
<213> ORGANISM: Artificial Sequence
<220> FEATURE:
<223> OTHER INFORMATION: AS83 vector monomer

<400> SEQUENCE: 66
ggaaagucgg aacaucuccc aucuuucccu gaagagacga agugaucaag agauccuucu      60
cucacaaguc gaaacucaga guc                                             83

<210> SEQ ID NO 67
<211> LENGTH: 83
<212> TYPE: RNA
<213> ORGANISM: Artificial Sequence
<220> FEATURE:
<223> OTHER INFORMATION: H83 vector monomer

<400> SEQUENCE: 67
caaaacucgg aacaucuccc auauuuugcu gaagagacga agugaucaag agauccuucu      60
cucacaaguc gaaaccaacg guc                                             83

<210> SEQ ID NO 68
<211> LENGTH: 16
<212> TYPE: RNA
<213> ORGANISM: Artificial Sequence
<220> FEATURE:
<223> OTHER INFORMATION: nucleotides 1752-1767 from HIV-1 gag

<400> SEQUENCE: 68
uuguuggucc aaaaug                                                     16

<210> SEQ ID NO 69
<211> LENGTH: 15
<212> TYPE: RNA
<213> ORGANISM: Artificial Sequence
<220> FEATURE:
<223> OTHER INFORMATION: target for the AS83 ribozyme which includes
      sequences 64-73 of avocado sunblotch viroid RNA

<400> SEQUENCE: 69
ucugagucgg aaagg                                                      15

<210> SEQ ID NO 70
<211> LENGTH: 38
<212> TYPE: DNA
<213> ORGANISM: Artificial Sequence
<220> FEATURE:
<223> OTHER INFORMATION: half-length oligonucleotide

<400> SEQUENCE: 70
cgaaaactgg actacaggga ggtaccaggt aatgtacc                             38

<210> SEQ ID NO 71

```
<211> LENGTH: 35
<212> TYPE: DNA
<213> ORGANISM: Artificial Sequence
<220> FEATURE:
<223> OTHER INFORMATION: half-length oligonucleotide

<400> SEQUENCE: 71
acaacgtgtg tttctctggt ctgcttctca ggaat                       35

<210> SEQ ID NO 72
<211> LENGTH: 14
<212> TYPE: RNA
<213> ORGANISM: Artificial Sequence
<220> FEATURE:
<223> OTHER INFORMATION: sequences of HIV-1 pol gene

<400> SEQUENCE: 72
cuguagucca ggaa                                              14

<210> SEQ ID NO 73
<211> LENGTH: 56
<212> TYPE: DNA
<213> ORGANISM: Artificial Sequence
<220> FEATURE:
<223> OTHER INFORMATION: circular ssDNA library constituent
      oligonucleotide
<221> NAME/KEY: misc_feature
<222> LOCATION: (9)..(48)
<223> OTHER INFORMATION: a, g, c, or t

<400> SEQUENCE: 73
ttcgtctgnn nnnnnnnnnn nnnnnnnnnn nnnnnnnntc tttcag           56

<210> SEQ ID NO 74
<211> LENGTH: 47
<212> TYPE: DNA
<213> ORGANISM: Artificial Sequence
<220> FEATURE:
<223> OTHER INFORMATION: circular ssDNA library constituent
      oligonucleotide

<400> SEQUENCE: 74
tttcgtcctc acggactcat cagaatggca acacattgac tgaggag          47

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
gactgaggag ttcgtctg                                          18

<210> SEQ ID NO 76
<211> LENGTH: 18
<212> TYPE: DNA
<213> ORGANISM: Artificial Sequence
<220> FEATURE:
<223> OTHER INFORMATION: primer
<221> NAME/KEY: misc_feature
<222> LOCATION: (1)..(1)
<223> OTHER INFORMATION: deoxyadenosine with 1-Dimethoxytrityloxy-2-
      (N-biotinyl-4-aminobutyl)-propyl-3-O-(2-cyanoethyl)-
      (N,N-diisopropyl)-phosphoramidite on its 5' phosphate group

<400> SEQUENCE: 76
natgtgttgc cattctga                                          18
```

<210> SEQ ID NO 77
<211> LENGTH: 24
<212> TYPE: DNA
<213> ORGANISM: Artificial Sequence
<220> FEATURE:
<223> OTHER INFORMATION: splint

<400> SEQUENCE: 77
aactcctcag tcaatgtgtt gcca                                    24

<210> SEQ ID NO 78
<211> LENGTH: 58
<212> TYPE: DNA
<213> ORGANISM: Artificial Sequence
<220> FEATURE:
<223> OTHER INFORMATION: circular ssDNA

<400> SEQUENCE: 78
gactgaggag ttcgtctggc aacgaatcag actctttcgg tgacattgcc cagtttat    58

<210> SEQ ID NO 79
<211> LENGTH: 45
<212> TYPE: DNA
<213> ORGANISM: Artificial Sequence
<220> FEATURE:
<223> OTHER INFORMATION: circular ssDNA

<400> SEQUENCE: 79
tctttcagtt tcgtcctcac ggactcatca gaatggcaac acatt              45

<210> SEQ ID NO 80
<211> LENGTH: 58
<212> TYPE: DNA
<213> ORGANISM: Artificial Sequence
<220> FEATURE:
<223> OTHER INFORMATION: circular ssDNA

<400> SEQUENCE: 80
gactgaggag ttcgtctggc cacgatctga atagtcgttc atcctcagcg gtagcgaa    58

<210> SEQ ID NO 81
<211> LENGTH: 45
<212> TYPE: DNA
<213> ORGANISM: Artificial Sequence
<220> FEATURE:
<223> OTHER INFORMATION: circular ssDNA

<400> SEQUENCE: 81
tctttcagtt tcgtcctcac ggactcatca gaatggcaac acatt              45

<210> SEQ ID NO 82
<211> LENGTH: 58
<212> TYPE: DNA
<213> ORGANISM: Artificial Sequence
<220> FEATURE:
<223> OTHER INFORMATION: circular ssDNA

<400> SEQUENCE: 82
gactgaggag ttcgtctggt aaagtatgtt gctacgactt ctttatttac cacgatgc    58

<210> SEQ ID NO 83
<211> LENGTH: 45
<212> TYPE: DNA
<213> ORGANISM: Artificial Sequence
<220> FEATURE:

-continued

<223> OTHER INFORMATION: circular ssDNA

<400> SEQUENCE: 83
tctttcagtt tcgtcctcac ggactcatca gaatggcaac acatt     45

<210> SEQ ID NO 84
<211> LENGTH: 35
<212> TYPE: DNA
<213> ORGANISM: Artificial Sequence
<220> FEATURE:
<223> OTHER INFORMATION: circular ssDNA

<400> SEQUENCE: 84
gactgaggag ttcgtctgtc tttcagtttc gtcct     35

<210> SEQ ID NO 85
<211> LENGTH: 28
<212> TYPE: DNA
<213> ORGANISM: Artificial Sequence
<220> FEATURE:
<223> OTHER INFORMATION: circular ssDNA

<400> SEQUENCE: 85
cacggactca tcagaatggc aacacatt     28

<210> SEQ ID NO 86
<211> LENGTH: 58
<212> TYPE: DNA
<213> ORGANISM: Artificial Sequence
<220> FEATURE:
<223> OTHER INFORMATION: circular ssDNA

<400> SEQUENCE: 86
gacactggag ttcgtctggt aaagtatgtt gctacgactt ctttatttac cacgatgc     58

<210> SEQ ID NO 87
<211> LENGTH: 45
<212> TYPE: DNA
<213> ORGANISM: Artificial Sequence
<220> FEATURE:
<223> OTHER INFORMATION: circular ssDNA

<400> SEQUENCE: 87
agaaagtgtt tcgtcctcac ggactcatca gagagcgttc actct     45

<210> SEQ ID NO 88
<211> LENGTH:
<212> TYPE:
<213> ORGANISM:

<400> SEQUENCE: 88

000

<210> SEQ ID NO 89
<211> LENGTH: 44
<212> TYPE: DNA
<213> ORGANISM: Artificial Sequence
<220> FEATURE:
<223> OTHER INFORMATION: circular ssDNA

<400> SEQUENCE: 89
agaaagtgtg tcgtcctcac ggactcatca gagagcgttc actc     44

<210> SEQ ID NO 90
<211> LENGTH: 60

<212> TYPE: DNA
<213> ORGANISM: Artificial Sequence
<220> FEATURE:
<223> OTHER INFORMATION: circular ssDNA
<221> NAME/KEY: misc_feature
<222> LOCATION: (11)..(50)
<223> OTHER INFORMATION: a, g, c, or t

<400> SEQUENCE: 90
agttcgtctg nnnnnnnnnn nnnnnnnnnn nnnnnnnnnn nnnnnnnnnn agaaagtgtt        60

<210> SEQ ID NO 91
<211> LENGTH: 43
<212> TYPE: DNA
<213> ORGANISM: Artificial Sequence
<220> FEATURE:
<223> OTHER INFORMATION: circular ssDNA

<400> SEQUENCE: 91
tcgtcctcac ggactcatca gagagcgttc actctgacac tgg        43

<210> SEQ ID NO 92
<211> LENGTH: 35
<212> TYPE: DNA
<213> ORGANISM: Artificial Sequence
<220> FEATURE:
<223> OTHER INFORMATION: circular ssDNA

<400> SEQUENCE: 92
gacactggag ttcgtctgag aaagtgtttc gtcct        35

<210> SEQ ID NO 93
<211> LENGTH: 28
<212> TYPE: DNA
<213> ORGANISM: Artificial Sequence
<220> FEATURE:
<223> OTHER INFORMATION: circular ssDNA

<400> SEQUENCE: 93
cacggactca tcagagagcg ttcactct        28

<210> SEQ ID NO 94
<211> LENGTH: 29
<212> TYPE: DNA
<213> ORGANISM: Artificial Sequence
<220> FEATURE:
<223> OTHER INFORMATION: primer

<400> SEQUENCE: 94
aggtcgacta tggagaaaaa aatcactgg        29

<210> SEQ ID NO 95
<211> LENGTH: 27
<212> TYPE: DNA
<213> ORGANISM: Artificial Sequence
<220> FEATURE:
<223> OTHER INFORMATION: primer

<400> SEQUENCE: 95
ggtacccaaa aggccatccg tcaggat        27

<210> SEQ ID NO 96
<211> LENGTH: 81
<212> TYPE: DNA
<213> ORGANISM: Artificial Sequence
<220> FEATURE:
<223> OTHER INFORMATION: primer

<400> SEQUENCE: 96
cccaagcttg tcactggaga aagtgtcaga gcgttcgggt tactccaaat ggcacctgca    60
aatggagaaa aaaatcactg g                                             81

<210> SEQ ID NO 97
<211> LENGTH: 29
<212> TYPE: DNA
<213> ORGANISM: Artificial Sequence
<220> FEATURE:
<223> OTHER INFORMATION: primer

<400> SEQUENCE: 97
ggggtaccca aaaggccatc cgtcaggat                                     29

<210> SEQ ID NO 98
<211> LENGTH: 22
<212> TYPE: DNA
<213> ORGANISM: Artificial Sequence
<220> FEATURE:
<223> OTHER INFORMATION: primer

<400> SEQUENCE: 98
gtatatccag tgattttttt ct                                            22

<210> SEQ ID NO 99
<211> LENGTH: 17
<212> TYPE: DNA
<213> ORGANISM: Artificial Sequence
<220> FEATURE:
<223> OTHER INFORMATION: primer

<400> SEQUENCE: 99
atgaccatga ttacgcc                                                  17

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
agagcgttcg ggttactcca                                               20

<210> SEQ ID NO 101
<211> LENGTH: 103
<212> TYPE: DNA
<213> ORGANISM: Artificial Sequence
<220> FEATURE:
<223> OTHER INFORMATION: single-stranded nanocircle containing 40nt of
      randomized sequence, and 63nt fixed sequence encoding a
      hammerhead ribozyme
<221> NAME/KEY: misc_feature
<222> LOCATION: (19)..(58)
<223> OTHER INFORMATION: a, g, c, or t

<400> SEQUENCE: 101
gactgaggag ttcgtctgnn nnnnnnnnnn nnnnnnnnnn nnnnnnnnnn nnnnnnnntc    60
tttcagtttc gtcctcacgg actcatcaga atggcaacac att                     103

<210> SEQ ID NO 102
<211> LENGTH:
<212> TYPE:
<213> ORGANISM:

<400> SEQUENCE: 102

000

<210> SEQ ID NO 103
<211> LENGTH:
<212> TYPE:
<213> ORGANISM:

<400> SEQUENCE: 103

000

<210> SEQ ID NO 104
<211> LENGTH: 40
<212> TYPE: DNA
<213> ORGANISM: Artificial Sequence
<220> FEATURE:
<223> OTHER INFORMATION: E1 motif I

<400> SEQUENCE: 104
gcaacgaatc agactctttc ggtgacattg cccagtttat                              40

<210> SEQ ID NO 105
<211> LENGTH: 40
<212> TYPE: DNA
<213> ORGANISM: Artificial Sequence
<220> FEATURE:
<223> OTHER INFORMATION: E38 motif II

<400> SEQUENCE: 105
gycacgatct gaatagtcgt tcatcctyag cggtagcgaa                              40

<210> SEQ ID NO 106

<400> SEQUENCE: 106

000                                                                      3

<210> SEQ ID NO 107

<400> SEQUENCE: 107

000                                                                      3

<210> SEQ ID NO 108
<211> LENGTH: 40
<212> TYPE: DNA
<213> ORGANISM: Artificial Sequence
<220> FEATURE:
<223> OTHER INFORMATION: nucleotide sequence containing E15 motif III

<400> SEQUENCE: 108
gcttaaggat taattgcatg ttattcttta ggagcctcga                              40

<210> SEQ ID NO 109
<211> LENGTH: 40
<212> TYPE: DNA
<213> ORGANISM: Artificial Sequence
<220> FEATURE:
<223> OTHER INFORMATION: nucleotide sequence containing E15 motif III

<400> SEQUENCE: 109
gtaaagtatg ttgctacgac ttctttattt accacgatgc                              40

<210> SEQ ID NO 110

```
<211> LENGTH:
<212> TYPE:
<213> ORGANISM:

<400> SEQUENCE: 110

000

<210> SEQ ID NO 111
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 111
gagcagtggt caactgacgg cttcgaaatg atatgcagcg                              40

<210> SEQ ID NO 112
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 112
tatgacgata ggattagacg tgtgggggta ttttcactac                              40

<210> SEQ ID NO 113
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 113
gtctcactcg gaggaggagt ctgacaagat gggatgctgc                              40

<210> SEQ ID NO 114
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 114
ggtattgcag actatttagc ctctgagagc cagaacggtc                              40

<210> SEQ ID NO 115
<211> LENGTH: 39
<212> TYPE: DNA
<213> ORGANISM: Artificial Sequence
<220> FEATURE:
<223> OTHER INFORMATION: selected nucleotide sequence

<400> SEQUENCE: 115
gagtggtaag tactgggagc cactcacgac aacgaacaa                               39

<210> SEQ ID NO 116
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 116
gtgctattcg tggctatact gttaatgtgt cgcaccattc                              40
```

```
<210> SEQ ID NO 117
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 117
ggccccgttt aggtacaatc acatgtacta gcgttgtggt                              40

<210> SEQ ID NO 118
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 118
gtagggttaa tatccttctc gtatgaccgt ggaagacgtc                              40

<210> SEQ ID NO 119
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 119
ggatgcgtag cgtaaagcgt tcgtatctcg aggtaagctt                              40

<210> SEQ ID NO 120
<211> LENGTH: 40
<212> TYPE: DNA
<213> ORGANISM: Artificial Sequence
<220> FEATURE:
<223> OTHER INFORMATION: selected nucleotide sequence

<400> SEQUENCE: 120
gagccatgga gcatactagt tgaactctag cttctagtcc                              40

<210> SEQ ID NO 121
<211> LENGTH: 103
<212> TYPE: DNA
<213> ORGANISM: Artificial Sequence
<220> FEATURE:
<223> OTHER INFORMATION: E1

<400> SEQUENCE: 121
gactgaggag ttcgtctggc aacgaatcag actctttcgt ttacattgcc cagtttattc        60
tttcagtttc gtcctcacgg actcatcaga atggcaacac att                         103

<210> SEQ ID NO 122
<211> LENGTH: 103
<212> TYPE: DNA
<213> ORGANISM: Artificial Sequence
<220> FEATURE:
<223> OTHER INFORMATION: E15

<400> SEQUENCE: 122
gactgaggag ttcgtctggt aaagtatgtt gctacgactt ctttatttac cacgatgctc        60
tttcagtttc gtcctcacgg actcatcaga atggcaacac att                         103

<210> SEQ ID NO 123
```

```
<211> LENGTH: 103
<212> TYPE: DNA
<213> ORGANISM: Artificial Sequence
<220> FEATURE:
<223> OTHER INFORMATION: E38

<400> SEQUENCE: 123
gactgaggag ttcgtctggc cacgatctga atagtcgttc atcctcagcg gtagcgaatc      60
tttcagtttc gtcctcacgg actcatcaga atggcaacac att                      103

<210> SEQ ID NO 124
<211> LENGTH: 13
<212> TYPE: RNA
<213> ORGANISM: Artificial Sequence
<220> FEATURE:
<223> OTHER INFORMATION: marA cleavage site

<400> SEQUENCE: 124
aagugucaga gcg                                                        13

<210> SEQ ID NO 125
<211> LENGTH: 103
<212> TYPE: RNA
<213> ORGANISM: Artificial Sequence
<220> FEATURE:
<223> OTHER INFORMATION: active marA

<400> SEQUENCE: 125
agagugaacg cucucugaug aguccgugag gacgaaacac uuucugcauc gugguaaaua      60
aagaagucgu agcaacauac uuuaccagac gaacuccagu guc                      103

<210> SEQ ID NO 126
<211> LENGTH: 103
<212> TYPE: RNA
<213> ORGANISM: Artificial Sequence
<220> FEATURE:
<223> OTHER INFORMATION: inactive marA

<400> SEQUENCE: 126
agagugaacg cucucugaug aguccgugag gacgacacac uuucugcauc gugguaaaua      60
aagaagucgu agcaacauac uuuaccagac gaacuccagu guc                      103

<210> SEQ ID NO 127
<211> LENGTH: 63
<212> TYPE: RNA
<213> ORGANISM: Artificial Sequence
<220> FEATURE:
<223> OTHER INFORMATION: short marA

<400> SEQUENCE: 127
agagugaacg cucucugaug aguccgugag gacgaaacac uuucucagac gaacuccagu      60
guc                                                                   63

<210> SEQ ID NO 128
<211> LENGTH: 21
<212> TYPE: DNA
<213> ORGANISM: Artificial Sequence
<220> FEATURE:
<223> OTHER INFORMATION: probe

<400> SEQUENCE: 128
ctccctgtag tccagttttc g                                               21
```

```
<210> SEQ ID NO 129
<211> LENGTH: 73
<212> TYPE: DNA
<213> ORGANISM: Artificial Sequence
<220> FEATURE:
<223> OTHER INFORMATION: DNA template encoding self-processing haripin
      ribozyme

<400> SEQUENCE: 129
ttcctgagaa gtcaaccaga gaaacacacg ttgtggtaca ttacctggta cctccctgta      60
gtccagtttt cga                                                        73
```